Figure 1:
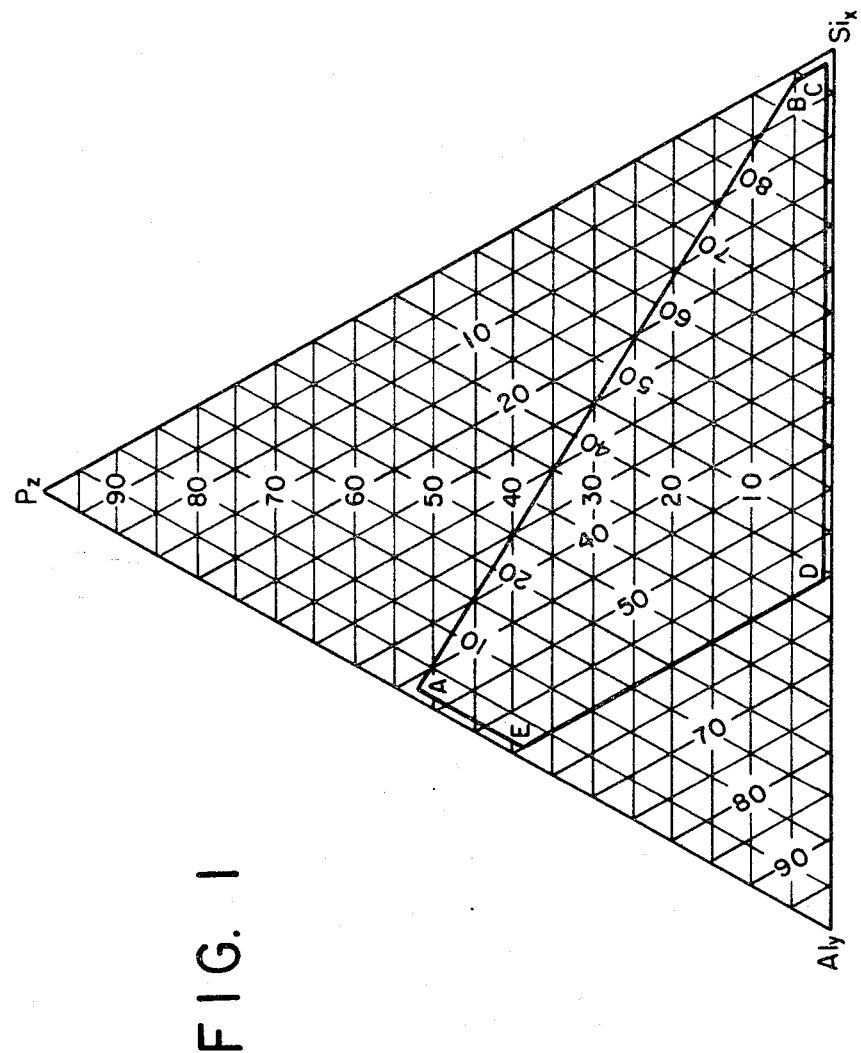

United States Patent [19]
Kaiser

[11] Patent Number: 4,499,327
[45] Date of Patent: Feb. 12, 1985

[54] PRODUCTION OF LIGHT OLEFINS
[75] Inventor: Steven W. Kaiser, South Charleston, W. Va.
[73] Assignee: Union Carbide Corporation, Danbury, Conn.
[21] Appl. No.: 426,213
[22] Filed: Oct. 4, 1982
[51] Int. Cl.³ .......................... C07C 1/00; B01J 27/14
[52] U.S. Cl. .................................. 585/640; 502/60; 423/303
[58] Field of Search ................ 585/640; 252/435, 437; 423/305; 502/60

[56] References Cited
U.S. PATENT DOCUMENTS
4,049,573  9/1977  Kaeding .............................. 585/640

FOREIGN PATENT DOCUMENTS
911410  10/1972  Canada .............................. 252/437
6122318  9/1981  Japan ................................ 585/640

Primary Examiner—Delbert E. Gantz
Assistant Examiner—Chung K. Pak
Attorney, Agent, or Firm—Gary L. Warner

[57] ABSTRACT

The process for the production of light olefins from a feedstock comprising methanol, ethanol, dimethyl ether, diethyl ether or mixtures thereof comprising contacting said feedstock with a silicoaluminophosphate molecular sieve at effective process conditions to produce light olefins.

58 Claims, 2 Drawing Figures

PRODUCTION OF LIGHT OLEFINS

FIELD OF THE INVENTION

The present invention relates to a new catalytic process for the production of light olefins, i.e., olefins having not more than four carbon atoms, from a feedstock comprising methanol, ethanol, dimethyl ether, diethyl ether or mixtures thereof in the presence of a silicoaluminophosphate molecular sieve catalyst.

BACKGROUND OF THE INVENTION

As a result of the limited availability and high cost of petroleum sources the cost of producing chemicals from such petroleum sources has been steadily increasing. Further, many in the chemical industry, as well as elsewhere, have raised the dire prediction of significant oil shortages in the not too distant future. As a result, the search for an alternative, low cost and more readily available raw material for chemical synthesis has been intense with the ultimate goal being the derivation of valuable chemical products from non-petroleum sources.

Such readily available sources are methanol, ethanol and their derivatives which may be manufactured from non-petroleum sources such as by fermentation or from synthesis gas, i.e. a mixture of oxides of carbon and hydrogen. Synthesis gas may be derived by the combustion of any carbonaceous material including coal, or any organic material, such as hydrocarbons, carbohydrates and the like. Thus, the use of methanol and its derivatives to form chemical products is particularly desirable in providing such a non-petroleum based route. The manufacture of methanol from synthesis gas by a heterogeneous catalytic reaction is presently an efficient commercial process.

Although methanol and its derivatives have for some time been considered as desirable starting materials for the manufacture of chemicals (which it is, e.g., in the manufacture of formaldehyde), the use of such as a replacement for petroleum or natural gas in commercial chemical syntheses has not been vast. If processes can be developed for the use of methanol and its derivatives for the commercial manufacture in large volume of chemical products or intermediates then the present dependence on petroleum sources as the basic raw material for chemical synthesis may be substantially lessened.

One proposed way to use methanol and its derivatives to manufacture chemical products is by catalytically converting them with crystalline aluminosilicate zeolites. Representative of the various contemplated processes using such crystalline aluminosilicate zeolites, and as more completely discussed hereinafter, are those processes disclosed in U.S. Pat. Nos. 4,062,905; 4,079,095; 4,079,096; 3,911,041; and 4,049,573. What appears to be evident from the above patents, as well as other patents, is that the process is tied to the particular catalyst employed yielding differences in: product ratios (as well as by-product formation); catalyst life; conversion to product; selectivity to product; catalyst attrition; and the effects from additives to the catalytic process. The significance of these differences is readily apparent by reviewing the divergent results of the published art wherein various catalysts have been employed for the conversion of methanol to light olefin products. Representative of this art are: European Application No. 6,501 (catalyst is HZSM-5); European Application No. 2,492 (catalyst is Mn exchanged 13X zeolite); German Offen. No. 2,909,928 (catalyst is Fe exchanged Silicalite); Angew. Chem. Int. Ed., 19, 2 (1980), 126-7 (catalyst is Mn exchanged Chabazite and erionite); South African No. 78/2527 (catalyst is CaH-Fu-1 zeolite); and European Application No. 11,900 (catalyst is boron modified silica).

For example, German Offen. No. 2,909,928 discloses a 95-100 percent conversion with 5.2 weight percent of the product as ethylene, whereas the publication Agnew. Chem. Int. Ed., 19, 2 (1980), 126-7 discloses a conversion of about 82 percent with 35.7 weight percent of the product as ethylene.

A brief discussion of selected patents and publications will further serve to point out differences involved in the conversion of methanol and derivatives thereof to light olefin products.

U.S. Pat. No. 4,062,905 discloses a process for the conversion of methanol, dimethyl ether or mixtures thereof to hydrocarbon products rich in ethylene and propylene using a catalyst comprising a crystalline aluminosilicate zeolite characterized by pores, the major dimension of which, are less than 6 Angstroms, the pores being further characterized by pore windows of about a size as would be provided by 8-membered rings of oxygen atoms. The process is alleged to have the capability under certain conditions of producing less than 20 weight percent methane by weight of the hydrocarbon product. The claimed correlation in the patent between pore size, process conditions and the level of methane production is admittedly specifically limited to the crystalline aluminosilicate zeolites, see the quote below.

The passage beginning at column 3, line 5 (also see Example 17) of U.S. Pat. No. 4,062,905 demonstrates this view:

"In addition to having the hereinabove described pore size characteristics, the crystalline aluminosilicate zeolite utilized as catalyst in the present process should have the capability of producing a hydrocarbon product containing less than 20 percent and preferably not more than 10 percent by weight of methane. Thus, the calcium form of zeolite A, having pores of approximately 5 Angstroms and commonly referred to as zeolite 5A, while satisfying the pore size requirements for zeolites useful as catalysts in the process described herein, is nevertheless, not a particularly feasible catalyst since under the conversion conditions utilized in such process, this zeolite produces considerable amounts of methane, i.e. far in excess of the specified maximum of 20 weight percent characterizing the crystalline aluminosilicate zeolites which have been found to be effective in selectively converting methanol and/or dimethyl ether to ethylene and propylene."

Even when a crystalline aluminosilicate zeolite having the desired physical and chemical properties is employed it may not be useful as a catalyst according to the patent's process. Thus, this patent discloses that the chemical composition of an aluminosilicate which has a desirable pore size may or may not be determinative as to whether it will produce methane at a given rate such that less than 20 percent by weight methane is produced.

The specificity of the catalysts in this field is demonstrated by U.S. Pat. Nos. 4,079,096 and 4,079,095 which disclose processes for the conversion of methanol, dimethyl ether or mixtures thereof to hydrocarbon products, such as ethylene and propylene, by contacting them with a catalyst comprising, respectively, a crystalline aluminosilicate zeolite of the erionite-offretite family and, the particular erionite-offretite of the crystalline aluminosilicate zeolite ZSM-34. The processes are limited to the use of crystalline aluminosilicates having substantially the same diffraction pattern as the erionite-offretite family.

U.S. Pat. No. 3,911,041 describes the conversion of methanol or dimethyl ether by contacting them with a crystalline aluminosilicate zeolite having a silica to alumina ratio of at least about 12, a constraint index of about 1 to 12, and containing phosphorous deposited on the crystal structure thereof in an amount of at least about 0.78 percent by weight. The phosphorous is disclosed as not in the framework of the crystalline aluminosilicate, as can be determined from the preparation procedure beginning at column 7, line 56 of the patent. The procedure set forth in the patent details that the crystalline aluminosilicate zeolite is formed prior to the addition of the phosphorus-containing compound, after which the phosphorous-containing compound is "reacted" with the surface sites of the zeolite to provide a surface treated material. Further, X-ray diffraction analyses of the zeolite before and after treatment with a phosphorus-containing compound showed substantially identical interplanar spacings (see Column 8, lines 54 to 64) indicating that no phosphorus was present in the framework. The surface treatment of the crystalline aluminosilicates is predicated on the patentees' belief that the number and strength of the aluminosilicates acid sites is related to the activity.

U.S. Pat. No. 4,049,573 describes a crystalline aluminosilicate zeolite having a silica to alumina ratio of at least 12 and a constraint index within the approximate range of 1 to 12, and having deposited thereon (as one of several possibilities) between about 0.25 and about 10 percent by weight of phosphorus oxide in combination with between about 0.25 and about 5 percent by weight of boron oxide and between about 2 and about 15 percent by weight of magnesium oxide. As was the case in the above-discussed U.S. Pat. No. 3,911,041, the phosphorous oxide, boron oxide and magnesium oxide are not incorporated into the zeolite framework but, instead, are added to the zeolite after the framework of the aluminosilicate zeolite has been formed, i.e. are provided as a post treatment of the aluminosilicate zeolite, apparently for the same reason.

As is evident from the above, the interest in selective catalysts for the manufacture of light olefins from methanol has been achieved from a special aluminosilicate structure or by achieving modifications of aluminosilicates by deposition with special additives. As above-noted, one of these was to deposit a phosphorous-containing compound (termed "doping" herein) in combination with a number of other compounds on an aluminosilicate zeolite.

U.S. Pat. Nos. 3,911,041 and 4,049,573, reports the sorption of phosphate ions onto amorphous metal oxides and combinations of metal oxides. Such sorptions of phosphate ions has been intensively studied in such areas as in the chemistry of soil, although such studies have not heretofore reported a crystalline microporous phosphate-containing material. For example, see: S. S. Rajan and K. W. Perrott, J. Soil Sci., 26, 257 (1975); J. A. Veith and G. Sposito, Soil. Sci., Soc. Am. J., 41, 870 (1977); E. A. Ferreiro and S. G. DeBussetto, Agrochimica, 24,184 (1980).

It has been reported (D. McConnell, Ameri. Min., 37, 609 (1952)) that certain natural aluminosilicate zeolites may have $PO_2^+$ substitution into the tetrahedral framework with such a substitution being reported in viseite which is considered to be isostructural with analcime. D. McConnell reported an elemental composition of:

$$5CaO:5Al_2O_3:3SiO_2:3P_2O_5:nH_2O.$$

This report should be viewed cautiously, if not with skepticism, in view of the considerable question of agreement on the X-ray powder diffraction patterns of such a substituted viseite and analcime owing to the highly defective structure (with dangling—OH groups wherever tetrahedral cation vacancies occur) resorted to in order to substantiate such structures as being isostructural.

R. M. Barrer and D. J. Marshall (J. Chem. Soc., 1965, 6616 and 6621) reported the attempted substitution of phosphorus in aluminosilicates during hydrothermal crystallizations in the system, in respect to the following:

$$Al_2O_3—SiO_2—P_2O_5\text{-base-}H_2O$$

Although phosphate was observed to co-precipitate with the aluminosilicates in this system there was no evidence that an aluminosilicophosphate framework had formed.

R. M. Barrer and M. Liquornick (J. Chem. Soc., Dalton Trans., 2126 (1974)) reported that by use of metakaolinite and phosphoric acid, and in some instances by further addition of silica, that zeolites were formed having an extremely low content of phosphorous with a maximum of 0.0117 atoms of phosphorus present per atom of aluminium. The authors explanation for this very low phosphorous content is that phosphate anions were trapped in cavities within the zeolite framework rather than actually being in the framework.

U.S. Pat. No. 3,443,892 discloses a process for making Zeolite X by mixing aluminum phosphate with hot sodium silicate to give an as-synthesized product having the general formula:

$$(0.5–1.1)Na_2O_3:Al_2O_3:(0–0.2)P_2O_5:(2.3–3.3)SiO_2:(0–7.2)H_2O$$

No chemical data is disclosed by the patentee for determining the framework structure and the patent requires that the ratio of $SiO_2$ to $Na_2O$ in the reaction mixture must be less than 1.

The synthesis of aluminosilicophosphate zeolite analogues having phosphorus incorporated into the tetrahedral sites of the zeolite-type framework during hydrothermal synthesis employing substantial amounts of alkali metal cations has been reported by E. M. Flanigen and R. W. Grose at Advances in Chem., Series No. 101 pages 76–101 (1971). (Also see: Canadian Pat. No. 911,410, issued Oct. 3, 1972 to Robert W. Grose and Edith M. Flanigen). In this report the authors reported compositions with the following types of zeolite-type frameworks: analcime, chabazite, phillipsite-harmotome, Type A zeolite, Type L zeolite, and Type B (P) zeolite. These compositions were reported to contain between 5 and 25 percent by weight $P_2O_5$ incorporated into the zeolite-type frameworks. The substitution of phosphorus for silicon did not appear to impart beneficial properties to the compositions not possessed by analogous aluminosilicate compositions, although differences were reported in some of the compositions, e.g. reduced adsorption capacity and reduced thermal stability on thermal activation. Many of the physical and chemical properties of the phosphorus-substituted analogues were inferior to those of the unsubstituted species.

DISCLOSURE OF THE INVENTION

This invention comprises a process for the catalytic conversion of a feedstock comprising one or more of methanol, ethanol, dimethyl ether, diethyl ether or mixtures thereof to a hydrocarbon product containing light olefinic products, i.e., $C_2$, $C_3$ and/or $C_4$ olefins. The feedstock is contacted with a silicoaluminophosphate molecular sieve at effective process conditions to produce light olefins. Silicoaluminophosphate molecular sieves which produce light olefins are generally employable in the instant process. Illustrative of preferred silicoaluminophosphates are those described in copending application U.S. Ser. No. 400,438, filed July 26, 1982, and commonly assigned. Silicoaluminophosphate molecular sieves employable in the instant process are more fully described hereinafter.

It has been found that silicoaluminophosphate molecular sieves are extremely efficient catalysts for the conversion of a feedstock comprising methanol, ethanol, dimethyl ether, diethyl ether or mixtures thereof to light olefins and that the two carbon, three carbon, and four carbon ($C_2$–$C_4$) light olefin product content of the hydrocarbon reaction products generally comprises a major portion of the hydrocarbon products while methane and aromatics typically comprise a minor portion thereof.

DESCRIPTION OF THE INVENTION

The instant process relates to making light olefins containing 2 to 4 carbon atoms wherein said process comprises contacting a feedstock with a silicoaluminophosphate molecular sieve comprising a molecular framework of [$AlO_2$], [$PO_2$] and [$SiO_2$] tetrahedral units, at effective process conditions to produce such light olefin products. It should be noted that the [$AlO_2$] tetrahedral unit has a net negative charge and the [$PO_2$] tetrahedral unit has a net positive charge, although such are not designated herein as such.

The term "light olefins" will be used hereinafter to refer to olefins having two to four carbon atoms, inclusive. Although other hydrocarbon products are formed, the products of particular interest herein are the light olefins and they are preferably produced as the major hydrocarbon products i.e., over 50 mole percent of the hydrocarbon product is light olefins. The ability of silicoaluminophosphate molecular sieves to catalytically provide for the formation of light olefins, preferably as the major portion of the hydrocarbon product, has not heretofore been reported or suggested. Silicoaluminophosphate molecular sieves employable in the instant process will be more fully discussed hereinafter.

It has been discovered that by use of silicoaluminophosphate molecular sieves as the catalyst(s) for the conversion of such a feedstock that, in general, higher feedstock conversions and selectivities (sometimes referred to as the "Molar Efficiency") to light olefin products may be obtained as compared to that obtained by use of the prior art aluminosilicate zeolites as catalysts. It has also been discovered that by use of specific silicoaluminophosphate molecular sieves that the selectivity to $C_2$ to $C_4$ olefin products (i.e., ethylene, propylene, and butenes) of at least about 25 molar percent, based on the total hydrocarbon products formed, may be obtained, preferably in excess of 50 mole percent. Further, the selectivity to such olefin products may be in excess of 75 mole percent when specific silicoaluminophosphate molecular sieves are employed. Further, high molar conversions i.e., perferably at least about 70 percent and most preferably at least about 90 percent, based on the moles of feedstock to products, may be obtained while forming a minimum molar amount of methane (less than about ten (10) molar percent and preferably less than about five (5) molar percent) and while forming only minor amounts of saturated hydrocarbons and $C_5$ and higher hydrocarbons (typically less than about 10 molar percent). In addition, it has been observed that the formation, if any, of aromatic hydrocarbons is below that which is detectable by standard vapor phase chromatographic techniques. An additional bonus is that certain silicoaluminophosphate molecular sieves as employed in the instant process are believed to have increased catalyst life with respect to the conversion of the instant feedstock to light olefin products as compared with the crystalline aluminosilicates (e.g. the ZSM-type). (For example, see example 2 of U.S. Pat. No. 4,079,095).

The process is preferably carried out in the vapor phase such that the feedstock is contacted in a vapor phase in a reaction zone with a silicoaluminophosphate molecular sieve at effective process conditions such as to produce light olefins, i.e., an effective temperature, pressure, WHSV (Weight Hourly Space Velocity) and, optionally, an effective amount of diluent, correlated to produce light olefins. Alternatively, the process may be carried out in a liquid phase. When the process is carried out in the liquid phase the process necessarily involves the separation of products formed in a liquid reaction media and can result in different conversions and selectivities of feedstock to product with respect to the relative ratios of the light olefin products as compared to that formed by the vapor phase process.

The temperature which may be employed in the process may vary over a wide range depending, at least in part, on the selected silicoaluminophosphate catalyst. In general, the process can be conducted at an effective temperature between about 200° C. and about 700° C., preferably between about 250° C. and about 600° C., and most preferably between about 300° C. and about 500° C. Temperatures outside the stated range are not excluded from the scope of this invention, although such do not fall within certain desirable embodiments of the invention. At the lower end of the temperature range and, thus, generally at the lower rate of reaction, the formation of the desired light olefin products may become markedly slow. At the upper end of the temperature range and beyond, the process may not form an optimum amount of light olefin products. Notwithstanding these factors, the reaction will still occur and the feedstock, at least in part, can be converted to the desired light olefin products at temperatures outside the range between about 200° C. and about 700° C.

The process is effectively carried out over a wide range of pressures including autogenous pressures. At pressures between about 0.001 atmospheres and about 1000 atmospheres, the formation of light olefin products will be effected although the optimum amount of product will not necessarily form at all pressures. The preferred pressure is between about 0.01 atmospheres and about 100 atmospheres. The pressures referred to herein for the process are exclusive of the inert diluent, if any is present, and refer to the partial pressure of the feedstock as it relates to methanol, ethanol, dimethylether, diethyl ether or mixtures thereof. Pressures outside the stated range are not excluded from the scope of this invention, although such do not fall within certain desirable embodiments of the invention. At the lower and upper end of the pressure range, and beyond, the selectivities, conversions and/or rates to light olefin products may not occur at the optimum although light olefin products can be formed.

The process is effected for a period of time sufficient to produce the desired light olefin products. In general, the residence time employed to produce the desired product can vary from seconds to a number of hours. It will be readily appreciated by one skilled in the art that the residence time will be determined to a significant extent by the reaction temperature, the silicoaluminophosphate molecular sieve selected, the WHSV, the phase (liquid or vapor) selected, and, perhaps, selected process design characteristics.

The process is effectively carried out over a wide range of WHSV for the feedstock and is generally between about 0.01 hr$^{-1}$ and about 100 hr$^{-1}$ and preferably between about 0.1 hr$^{-1}$ and about 40 hr$^{-1}$. Values above 100 hr$^{-1}$ may be employed and are intended to be covered by the instant process, although such are not preferred.

The instant process is most preferably carried out under process conditions comprising a temperature between about 300° C. and about 500° C., a pressure between about 0.1 atmosphere (one atmosphere equals 14.7 psia) to about 100 atmospheres, utilizing a WHSV expressed in hr$^{-1}$ for each component of the feedstock having a value between about 0.1 and about 40. The temperature, pressure, and WHSV are each selected such that the effective process conditions, i.e., the effective temperature, pressure, and WHSV, are employed in conjunction, i.e. correlated, with the selected silicoaluminophosphate molecular sieve and selected feedstock such that light olefin products are produced.

In addition to the presence of methanol, ethanol, dimethyl ether, diethyl ether, or mixtures thereof in the feedstock, a diluent may be present in the feedstock in an amount between about 1 and about 99 molar percent, based on the total number of moles of all feed components fed to the reaction zone (or catalyst). Typical of the diluents which may be employed in the instant process are helium, argon, nitrogen, carbon monoxide, carbon dioxide, hydrogen, water(steam), paraffins, hydrocarbons (such as methane and the like), aromatics (such as benzene, toluene, xylenes and the like), mixtures thereof, and the like.

It has been discovered that the addition of a diluent to the feedstock prior to such being employed in the instant process is generally beneficial, although not required.

The instant process may be carried out in a batch, semi-continuous, or continuous fashion. The process can be conducted in a single reaction zone or a number of reaction zones arranged in series or in parallel, or it may be conducted intermittently or continuously in an elongated tubular zone or a number of such zones. When multiple reaction zones are employed, it may be advantageous to employ one or more of such silicoaluminophosphate molecular sieves in series to provide for a desired product mixture. Owing to the nature of the process, it may be desirous to carry out the instant process by use of the silicoaluminophosphates in a dynamic (e.g. fluidized or moving) bed system or any system of a variety of transport beds rather than in a fixed bed system. Such systems would readily provide for any regeneration (if required) of the silicoaluminophosphate molecular sieve catalyst after a given period of time. If regeneration is required, the silicoaluminophosphate molecular sieve catalyst can be continuously introduced as a moving bed to a regeneration zone where it can be regenerated, such as for example by removing carbonaceous materials by oxidation in an oxygen-containing atmosphere In the preferred practice of the invention, the catalyst will be subject to a regeneration step by burning off carbonaceous deposits accumulated during reactions.

SILICOALUMINOPHOSPHATES

The selection of the silicoaluminophosphate molecular sieve catalysts for the instant process is preferably related, in part, to the desired product mixture sought to be obtained. The selected silicoaluminophosphate molecular sieve desirably has a kinetic pore diameter (average kinetic diameter in Angstroms, Å) such that the selectivity to the light olefin products is greater than 50 molar percent. Accordingly, at least a portion, preferably a major portion, of the pores have an average kinetic diameter characterized such that the adsorption capacity (as measured by the standard McBain-Bakr gravimetric adsorption method using given adsorbate molecules)* shows adsorption of oxygen (average kinetic diameter of about 3.46 Å) and negligible adsorption of isobutane (average kinetic diameter of about 5.0 Å). More preferably the average kinetic diameter is characterized by adsorption of Xenon (average kinetic diameter of about 4.0 Å) and negligible adsorption of isobutane and most preferably by adsorption of n-hexane (average kinetic diameter of about 4.3 Å) and negligible adsorption of isobutane. Negligible adsorption of oxygen or xenon is adsorption of less than four percent by weight of the adsorbate based on the weight of the silicoaluminophosphate and adsorption of oxygen or xenon is adsorption of greater than or equal to four percent by weight of the adsorbate based on the weight of the silicoaluminophosphate. Negligible adsorption of n-hexane or isobutane is adsorption of less than two percent by weight of the adsorbate based on the weight of the silicoaluminophosphate and adsorption of n-hexane or isobutane is adsorption of greater than or equal to two percent by weight of the adsorbate based on the weight of the silicoaluminophosphate. Although it is clear that factors other than just the kinetic pore size will affect the products formed, including any occlusion of the pores, the exact nature of such other factors or their exact effect on the products formed are not understood at present. It is believed that the kinetic diameter of the pores of the siliconaluminophosphate molecular sieve is related to the products formed. Although a specific silicoaluminophosphate may not have a kinetic pore diameter within the desired or preferred range the silicoaluminophosphate may be modified by depositing or impregnating such with cations, anions, salts and/or compounds that occlude or otherwise result in the modification of a silicoaluminophosphates having a large pore size to one having a kinetic pore diameter(s) within the desired or preferred range.

* The McBain-Bakr gravimetric method should be carried out with reference to the following pressure and temperature for a given adsorbate:

|  | Adsorbate Pressure | Temperature |
|---|---|---|
| $O_2$ | about 100 Torr | $-183°$ C. |
| n-hexane | about 45 Torr | ambient[1] |
| Xenon | about 750 Torr | ambient[1] |
| isobutane | about 760 Torr | ambient[1] |

[1] Ambient temperature is from about 20° C. to about 25° C.

Techniques which may be employed to effect the diminution of the pore size of a silicoaluminophosphate molecular sieve are generally known in the art. Such procedures generally involve the introduction to a pore of a pore size restricting material and may involve such procedures as (1) impregnating the silicoaluminophosphate with a solution comprising a solvent or solubilizing agent for such a pore restricting material (one or more) in an amount sufficient to deposit the desired weight of such pore restricting material to the silicoaluminophosphate such that the desired pore size is obtained and/or (2) exchanging the silicoaluminophosphate with a solution containing the pore size restricting material. The impregnation or deposition of the pore restricting materials may be generally accomplished by heating the silicoaluminophosphate at an elevated temperature to evaporate any liquid present to effect deposition or impregnation of the pore restricting material into the interior and/or onto the exterior surface of the silicoaluminophosphate, or by the exchange of cations present in the silicoaluminophosphate with cations that provide for the desired kinetic pore size. Alternatively, the pore restricting material may be formed on the silicoaluminophosphate from an emulsion or slurry containing the pore restricting material by heating the silicoaluminophosphate as described above. Impregnation and exchange procedures are generally the preferred techniques because they utilize and introduce the pore restricting material more efficiently than other procedures such as coating procedures since a coating procedure is generally not able to effect substantial introduction of the pore restricting material onto the interior surfaces of the silicoaluminophosphate. In addition, coated materials are more generally susceptible to the loss of the pore restricting materials by abrasion.

Suitable pore restricting materials include alkali metal, alkaline earth metals, transition metals and the salts thereof including inorganic and organic salts such as: nitrates, halides, hydroxides, sulfates and carboxylates. Other pore restricting materials generally employed in the art for such are also believed to be employable herein.

In carrying out the instant process the silicoaluminophosphate molecular sieves may be admixed (blended) or provided sequential to other materials which may provide some property which is beneficial under process conditions, such as improved temperature resistance or improved catalyst life by minimization of coking or which is simply inert under process conditions. Such materials may include synthetic or naturally occurring substances as well as inorganic material such as clays, silicas, aluminas, crystalline aluminosilicate zeolites, metal oxides and mixtures thereof. In addition, the silicoaluminophosphate molecular sieves may be formed with materials such as silica, alumina, silica-alumina, silica-magnesia, silico-zirconia, silica-thoria, silica-berylia, silica-titania, as well as ternary compositions, such as silica-alumina-thoria, silica-alumina-zirconia and clays present as binders. The relative proportions of the above materials and the silicoaluminophosphate may vary widely with silicoaluminophosphate content ranging between about 1 and about 99 percent by weight of the composite.

The silicoaluminophosphate molecular sieves employed in the instant process and as described in U.S. Pat. No. 4,440,871, issued Apr. 3, 1984, will be referred to hereinafter, solely for point of reference herein, as "SAPO" molecular sieves, or as "SAPOs" if the reference is to the class as a whole as employed herein. This designation is simply made for the sake of convenient reference herein and is not meant to designate a particular structure for any given silicoaluminophosphate (SAPO) molecular sieve. Although, the class of SAPO's employable in the instant process is that class which will produce $C_2$, $C_3$ and/or $C_4$ olefins from the feedstock at a sufficient temperature and related process conditions. The class of SAPO's described in copending U.S. Ser. No. 400,438, filed July 26, 1982, is particularly well suited for use in the present process. The members of the class of SAPO's employed hereinafter in the examples will be characterized simply by referring to such members as SAPO-5, SAPO-11, etc, i.e., a particular species will be referred to as SAPO-n where "n" is a number specific to a given class member as its preparation is reported herein. This designation is an arbitrary one and is not intended to denote structure or relationship to another material(s) which may also be characterized by a numbering system.

SILICOALUMINOPHOSPHATE COMPOSITIONS (SAPOs)

Silicoaluminophosphate molecular sieves (SAPOs) suitable for use in the instant process comprise any molecular sieve having a silicoaluminophosphate molecular framework which comprises a molecular framework of corner-sharing $[SiO_2]$ tetrahedra, $[AlO_2]$ tetrahedra and $[PO_2]$ tetrahedra, (i.e., $(Si_xAl_yP)O_2$ tetrahedral units), and which functions to convert at effective process conditions the aforementioned feedstock to one or more light olefin products and includes those silicoaluminophosphate molecular sieves described in copending U.S. Ser. No. 400,438.

The preferred SAPO's are characterized as comprising a three-dimensional microporous crystal framework structure of $[SiO_2]$, $[AlO_2]$ and $[PO_2]$ tetrahedral units which has a unit empirical formula on an anhydrous basis of:

$$mR: (Si_xAl_yP_z)O_2 \qquad (1)$$

wherein "R" represents at least one organic templating agent (hereinafter also referred to as "template") present in the intracrystalline pore system; "m" represents the moles of "R" present per mole of $(Si_xAl_yP_z)O_2$ and has a value from zero (0) to about 0.3, with the maximum value of m being related, at least in part, to the molecular dimensions of the template and the void volume of the intracrystalline pore system of the particular SAPO; "x", "y" and "z" represent the mole fractions of silicon, aluminum and phosphorus, respectively, present as tetrahedral oxide units, said mole fractions being within the pentagonal compositional area defined by points A, B, C, D and E of the ternary compositional diagram depicted by FIG. 1 of the drawings where the points A, B, C, D and E are represented by the following values for "x", "y" and "z":

| Point | Mole Fraction | | |
|---|---|---|---|
| | x | y | z |
| A | 0.01 | 0.47 | 0.52 |
| B | 0.94 | 0.01 | 0.05 |
| C | 0.98 | 0.01 | 0.01 |
| D | 0.39 | 0.60 | 0.01 |
| E | 0.01 | 0.60 | 0.39 |

Figure 2:
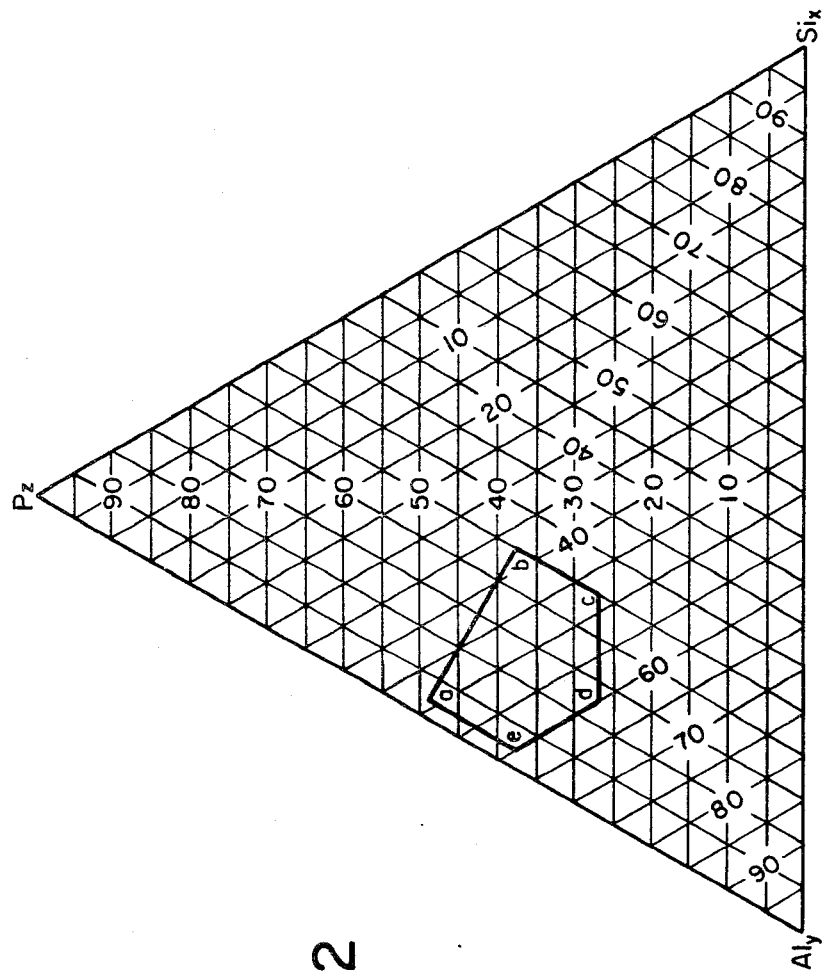

A preferred sub-class of the SAPOs of Formula (1), above, have a minimum value for "m" of 0.02 in the as-synthesized form and have the values for "x", "y" and "z" within the pentagonal compositional area defined by the points a, b, c, d and e of the ternary diagram which is FIG. 2 of the drawings, wherein said points a, b, c, d and e are represented by the following values for "x", "y" and "z":

| Point | Mole Fraction | | |
|---|---|---|---|
| | x | y | z |
| a | 0.02 | 0.49 | 0.49 |
| b | 0.25 | 0.37 | 0.38 |
| c | 0.25 | 0.48 | 0.27 |
| d | 0.13 | 0.60 | 0.27 |
| e | 0.02 | 0.60 | 0.38 |

The term "unit empirical formula" is used herein according to its common meaning to designate the simplest formula which gives the relative number of atoms of silicon, aluminum and phosphorus which form a $[PO_2]$, $[AlO_2]$ and $[SiO_2]$ tetrahedral unit within a silicoaluminophosphate molecular sieve and which forms the molecular framework of the SAPO composition(s). The unit empirical formula is given in terms of silicon, aluminum and phosphorus as shown in Formula (1), above, and does not include other compounds, cations or anions which may be present as a result of the SAPO's preparation or the existence of other impurities or materials in the bulk composition not containing the aforementioned tetrahedral unit as the molecular framework. The amount of template R is reported as part of the composition when the as-synthesized unit empirical formula is given, and water may also be reported unless such is defined as the anhydrous form. For convenience, coefficient "m" for template "R" is reported as a value that is normalized by dividing the number of moles of R by the total number of moles of silicon, phosphorus and aluminum. When moles of water are reported the moles of water relative to the mole fractions of silicon, aluminum and phosphorus is reported as a value that is normalized by dividing the number of moles of water by the total moles of silicon, phosphorus and aluminum. The values for x, y and z are determined by dividing the number of moles of silicon, aluminum, and phosphorus individually by the total number of moles of silicon, aluminum and phosphorus.

The unit empirical formula for a SAPO may be given on an "as-synthesized" basis or may be given after an "as-synthesized" SAPO composition has been subjected to some post treatment process, e.g., calcined. The term "as-synthesized" herein shall be used to refer to the SAPO composition(s) formed as a result of the hydrothermal crystallization but before the SAPO composition has been subjected to post treatment to remove any volatile components present therein. The actual value of "m" for a post-treated SAPO will depend on several factors (including: the particular SAPO, template, severity of the post-treatment in terms of its ability to remove the template from the SAPO, the proposed application of the SAPO composition, and etc.) and the value for "m" can be within the range of values as defined for the as-synthesized SAPO compositions although such is generally less than the as-synthesized SAPO unless such post-treatment process adds template to the SAPO so treated. A SAPO composition which is in the calcined or other post-treated form generally has an empirical formula represented by Formula (1), except that the value of "m" is generally less than about 0.02. Under sufficiently severe post-treatment conditions, e.g. roasting in air at high temperature for long periods (over 1 hr.), the value of "m" may be zero (0) or, in any event, the template, R, is undetectable by normal analytical procedures.

The above silicoaluminophosphates are generally synthesized by hydrothermal crystallization from a reaction mixture comprising reactive sources of silicon, aluminum and phosphorus, and one or more organic templating agents. Optionally, alkali metal(s) may be present in the reaction mixture. The reaction mixture is placed in a sealed pressure vessel, preferably lined with an inert plastic material, such as polytetrafluoroethylene, and heated, preferably under autogenous pressure at a temperature of at least about 100° C., and preferably between 100° C. and 250° C., until crystals of the silicoaluminophosphate product are obtained, usually for a period of from 2 hours to 2 weeks. While not essential to the synthesis of SAPO compositions, it has been found that in general stirring or other moderate agitation of the reaction mixture and/or seeding the reaction mixture with seed crystals of either the SAPO to be produced, or a topologically similar composition, facilitates the crystallization procedure. The product is recovered by any convenient method such as centrifugation or filtration.

After crystallization the SAPO may be isolated and washed with water and dried in air. As a result of the hydrothermal crystallization, the as-synthesized SAPO contains within its intracrystalline pore system at least one form of the template employed in its formation. Generally, the template is a molecular species, but it is possible, steric considerations permitting, that at least some of the template is present as a charge-balancing cation. Generally the template is too large to move freely through the intracrystalline pore system of the formed SAPO and may be removed by a post-treatment process, such as by calcining the SAPO at temperatures of between about 200° C. and to about 700° C. so as to thermally degrade the template or by employing some other post-treatment process for removal of at least part of the template from the SAPO. In some instances the pores of the SAPO are sufficiently large to permit transport of the template, and, accordingly, complete or partial removal thereof can be accomplished by conventional desorption procedures such as carried out in the case of zeolites.

The SAPOs are preferably formed from a reaction mixture having a mole fraction of alkali metal cation which is sufficiently low that it does not interefere with the formation of the SAPO composition. Although the SAPO compositions will form if alkali metal cation are present, such reaction mixtures are not generally preferred. A reaction mixture, expressed in terms of molar oxide ratios, having the following bulk composition is preferred:

$$aR_2O:(Si_xAl_yP_z)O_2:bH_2O$$

wherein "R" is a template; "a" has a value great enough to constitute an effective concentration of "R" and is within the range of from greater than zero (0) to about 3; "b" has a value of from zero to 500; "x", "y" and "z" represent the mole fractions, respectively of silicon, aluminum and phosphorus wherein x, y and z each have a value of at least 0.01. The reaction mixture is preferably formed by combining at least a portion of the reactive aluminum and phosphorus sources in the substantial absence of the silicon source and thereafter combining the resulting reaction mixture comprising the aluminium and phosphorus sources with the silicon source. When the SAPOs are synthesized by this method the value of "m" in Formula (1) is generally above about 0.02.

Though the presence of alkali metal cations are not preferred, when they are present in the reaction mixture it is preferred to first admix at least a portion of each of the aluminum and phosphorus sources in the substantial absence of the silicon source. This procedure avoids adding the phosphorus source to a highly basic reaction mixture containing the silicon and aluminum source, (as was done in most of the published attempts to substitute isomorphously [$PO_2$] tetrahedra for [$SiO_2$] tetrahedra in zeolite structures). Although the reaction mechanism is by no means clear at this time, the function of the template may be to favor the incorporation of [$PO_2$] and [$AlO_2$] tetrahedra in the framework structures of the crystalline products with [$SiO_2$] tetrahedra isomorphously replacing [$PO_2$] tetrahedra.

The reaction mixture from which these SAPOs are formed contain one or more organic templating agents (templates) which can be most any of those heretofore proposed for use in the synthesis of aluminosilicates and aluminophosphates. The template preferably contains at least one element of Group VA of the Periodic Table, particularly nitrogen, phosphorus, arsenic and/or antimony, more preferably nitrogen or phosphorus and most preferably nitrogen. The template contains at least one alkyl, aryl, araalkyl, or alkylaryl group. The template preferably contains from 1 to 8 carbon atoms, although more than eight carbon atoms may be present in the template. Nitrogen-containing templates are preferred, including amines and quaternary ammonium compounds, the latter being represented generally by the formula $R'_4N^+$ wherein each R' is an alkyl, aryl, alklaryl, or araalkyl group; wherein R' preferably contains from 1 to 8 carbon atoms or higher when R' is alkyl and greater than 6 carbon atoms when R' is otherwise, as hereinbefore discussed. Polymeric quaternary ammonium salts such as $[(C_{14}H_{32}N_2)(OH)_2]_x$ wherein "x" has a value of at least 2 may also be employed. The mono-, di- and tri-amines, including mixed amines, may also be employed as templates either alone or in combination with a quaternary ammonium compound or another template. The exact relationship of various templates when concurrently employed is not clearly understood. Mixtures of two or more templating agents can produce either mixtures of SAPOs or in the instance where one template is more strongly directing than another template the more strongly directing template may control the course of the hydrothermal crystallization wherein with the other template serving primarily to establish the pH conditions of the reaction mixture.

Representative templates include tetramethylammonium, tetraethylammonium, tetrapropylammonium or tetrabutylammonium ions; di-n-propylamine; tripropylamine; triethylamine; triethanolamine; piperidine; cyclohexylamine; 2-methylpyridine; N,N-dimethylbenzylamine; N,N-diethylethanolamine; dicyclohexylamine; N,N-dimethylethanolamine; choline; N,N'-dimethylpiperazine; 1,4-diazabicyclo(2,2,2) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo(2,2,2)octane ion; di-n-butylamine, neopentylamine; di-n-pentylamine; isopropylamine; t-butylamine; ethylenediamine; pyrrolidine; and 2-imidazolidone. As will be readily apparent from the illustrative examples set forth hereinafter, not every template will produce every SAPO composition although a single template can, with proper selection of the reaction conditions, cause the formation of different SAPO compositions, and a given SAPO composition can be produced using different templates.

In those instances where an aluminum alkoxide is the reactive aluminum source, the corresponding alcohol is necessarily present in the reaction mixture since it is a hydrolysis product of the alkoxide. It has not as yet been determined whether this alcohol participates in the synthesis process as a templating agent, or in some other function and, accordingly, is not reported as a template in the unit formula of the SAPOs, although such may be acting as templates.

Alkali metal cations in the reaction mixture may facilitate the crystallization of certain SAPO phases, although the exact function of such cations in crystallization, if any, is not presently known. Alkali cations present in the reaction mixture generally appear in the formed SAPO composition, either as occluded (extraneous) cations and/or as structural cations balancing net negative charges at various sites in the crystal lattice. It should be understood that although the unit formula for the SAPOs does not specifically recite the presence of alkali cations they are not excluded in the same sense that hydrogen cations and/or hydroxyl groups are not specifically provided for in the traditional formulae for zeolitic aluminosilicates.

Most any reactive phosphorus source may be employed herein such that [$PO_2$] tetrahedra are provided for in the SAPO framework. Phosphoric acid is the most suitable phosphorus source employed to date. Accordingly, other acids of phosphorus are generally believed to be suitable phosphorus sources for use herein. Organic phosphates such as triethyl phosphate have been found satisfactory, and so also have crystalline or amorphous aluminophospates such as the $AlPO_4$ compositions of U.S. Pat. No. 4,310,440. Organo-phosphorus compounds, such as tetrabutylphosphonium bromide have not, apparently, served as reactive sources of phosphorus, but these compounds do function as templating agents and may also be capable of being suitable phosphorus sources under proper process conditions (yet to be ascertained). Organic phosphorus compounds, e.g. esters, are believed to be generally suitable since they can generate acids of phosphorus in situ. Conventional phosphorus salts, such as sodium metaphosphate, may be used, at least in part as the phosphorus source, but they are not preferred.

Most any reactive aluminum source may be employed herein such that [AlO$_2$] tetrahedra are provided for incorporation in the SAPO framework. The preferred reactive aluminum sources include aluminum alkoxides, such as aluminum isoproproxide, and pseudoboehmite. Crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are generally not preferred.

Most any reactive silicon source may be employed herein such that [SiO$_2$] tetrahedra are provided for incorporation in the SAPO framework. Silicon is preferably introduced into the reaction system as either a silica sol or as fumed silica, but other conventional sources of silicon used in zeolite synthesis procedures can be employed. For example, a reactive solid amorphous precipitated silica, silica gel, silicic acid or alkali metal silicate may be employed as the silicon source with the last two named not being preferred. The silicon source material is preferably not an alkali metal silicate owing to the high pH conditions necessarily imparted to reaction mixtures by such alkali metal silicates where high molar SiO$_2$/Al$_2$O$_3$ ratios are desired, since such result in a marked tendency to produce extraneous aluminophosphates compositions. While the high pH conditions can be avoided by in situ neutralization with an acid and the consequent formation of a precipitated silica, this is, in effect, the use of silica as the reactive silicon source rather than an alkali metal silicate. Accordingly, if alkali metal silicate is employed as a reagent, it is preferably used in conjunction with another source of reactive silicon and the alkali metal silicate comprises a minor proportion (less than 50 percent by weight) of the overall reactive silicon source with the reaction mixture having the same composition, expressed in terms of mole ratios of oxides, as set forth hereinabove for the process wherein such alkali metals are present in the reaction mixture.

SILICOALUMINOPHOSPHATE COMPOSITIONS: PREPARATIVE EXAMPLES

SAPO compositions employable in present invention were prepared as follows and as set forth in Examples 1 to 24:

SAPO-5

SAPO-5, as referred to herein, comprises a silicoaluminophosphate material having a three-dimensional microporous crystal framework structure of [PO$_2$], [AlO$_2$] and [SiO$_2$] tetrahedral units whose unit empirical formula on an anhydrous basis is:

wherein "R" represents at least one organic templating agent present in the intracrystalline pore system; "m" represents the moles of "R" present per mole of (Si$_x$Al$_y$P$_z$)O$_2$ and has a value from zero to 0.3; "x", "y" and "z" represent, respectively, the mole fractions of silicon, aluminum and phosphorus, said mole fractions being within the compositional area bounded by points A, B, C, D and E on the ternary diagram which is FIG. 1, or more preferably within the area bounded by points a, b, c, d and e on the ternary diagram which is FIG. 2, and having a characteristic X-ray powder diffraction pattern which contains at least the d-spacings (both as-synthesized and calcined) set forth below in Table I. In the as-synthesized form "m" preferably has a value of from 0.02 to 0.3.

TABLE I

| 2θ | d | Relative Intensity |
|---|---|---|
| 7.35–7.65 | 12.0–11.56 | m–vs |
| 19.6–19.95 | 4.53–4.46 | m |
| 20.9–21.3 | 4.25–4.17 | m–vs |
| 22.3–22.6 | 3.99–3.93 | m–vs |
| 25.85–26.15 | 3.46–3.40 | w–m |

All of the as-synthesized SAPO-5 compositions for which X-ray powder diffraction data have presently been obtained have patterns which are within the generalized pattern of Table II below:

TABLE II

| 2θ | d | 100 × I/I$_o$ |
|---|---|---|
| 7.35–7.65 | 12.0–11.56 | 52–100 |
| 12.75–13.1 | 6.94–6.76 | 7–18 |
| 14.8–15.1 | 5.99–5.91 | 13–25 |
| 19.6–19.95 | 4.53–4.47 | 31–56 |
| 20.9–21.3 | 4.25–4.17 | 30–100 |
| 22.3–22.6 | 3.99–3.93 | 44–100 |
| 24.6–24.8 | 3.62–3.59 | 2–5 |
| 25.8–26.15 | 3.453–3.408 | 19–37 |
| 28.9–29.25 | 3.089–3.053 | 8–21 |
| 29.9–30.25 | 2.998–2.954 | 11–22 |
| 33.3–33.85 | 2.691–2.648 | 2–5 |
| 34.4–34.8 | 2.607–2.578 | 9–16 |
| 36.8–37.2 | 2.442–2.417 | 2–3 |
| 37.5–37.9 | 2.398–2.374 | 6–13 |
| 40.6–41.0 | 2.222–2.201 | 0–1 |
| 41.4–41.8 | 2.181–2.161 | 1–3 |
| 42.1–42.4 | 2.146–2.132 | 2–5 |
| 42.6–42.9 | 2.122–2.108 | 1–4 |
| 43.5–43.6 | 2.080–2.076 | 1–3 |
| 44.9–45.0 | 2.019–2.014 | 0–3 |
| 47.55–48.1 | 1.912–1.892 | 3–8 |
| 51.4–51.65 | 1.778–1.773 | 0–2 |
| 51.8–52.1 | 1.765–1.755 | 0–2 |
| 55.4–55.8 | 1.658–1.647 | 1–4 |

It has been noted in the case of SAPO-5 that the d-spacings of Table I are common to the X-ray patterns of all of the as-synthesized forms, i.e., template-containing, and calcined forms of SAPO-5 which have presently been obtained. It has been found, however, that in the case of the X-ray patterns of several other SAPO species, there can be an apparent substantial difference in the position and intensities of certain d-spacings between the as-synthesized and the calcined form. These differences are not believed to be indicative of a fundamental structure change as a consequence of calcination, but rather indicate a relaxation of lattice distortion caused by the presence of organic templating agents in the intracrystalline pore system which are too large to be accommodated without some bond-stretching within the SAPO crystal lattice. Upon calcination, removal of the organic species by thermal destruction permits the structure to relax to its normal condition. Thus, it may be possible to utilize a templating agent in the preparation of SAPO-5, or any SAPO species, which is large enough to change the position of one or more d-spacings with respect to the X-ray patterns presented for such species while not creating a distinct silicoaluminophosphate crystal structure.

EXAMPLE 1 (SAPO-5)

SAPO-5 was prepared by combining 7.69 grams of 85 wt.% orthophosphoric acid ($H_3PO_4$) with 33.29 grams of water. To this mixture 4.58 grams of a hydrated aluminum oxide was added, (a psuedo-boehmite phase, 74.2 wt.% $Al_2O_3$ and 25.8 wt.% $H_2O$) and the resulting mixture was stirred until homogeneous. To this mixture was added, sequentially, 1.08 gram of 37 wt.% HCl, and 2.16 grams of a fumed silica (92.8 wt.% $SiO_2$ and 7.2 wt.% $H_2O$) and the resulting mixture was stirred until homogeneous. To this mixture there was added 16.30 grams of an aqueous solution of 40 wt.% tetraethylammonium hydroxide (TEAOH)* and the mixture stirred until homogeneous. The composition of the resulting reaction mixture expressed in terms of molar ratios was:

$Al_2O_3:P_2O_5:0.665(TEA)_2O:SiO_2:0.33HCl:80H_2O$

*The template is reported here and may be reported in the remaining examples as the cation as associated in the oxide form or as the cation. Thus, in the formula $(TEA)_2O$ the TEA corresponds to the tetraethylammonium cation. Similar designations are employed in the other preparative examples.

The relative molar proportion in the reaction mixture of silicon, aluminum and phosphorus expressed in accordance with Formula (1) but on a hydrous basis was:

$0.27(TEA):(Si_{0.20}Al_{0.40}P_{0.40})O_2:16H_2O$

A portion of this reaction mixture was sealed in a stainless steel pressure vessel lined with polytetrafluoroethylene (inert liner) and heated in an oven at 150° C. at the autogenous pressure for 168 hours. The solid reaction product was recovered by filtration, washed with water, and dried in air overnight at ambient temperature. The composition of the as-synthesized solid product was determined in accordance with the law of mass balance using data derived from the chemical analysis of the mother liquor and was calculated to be as follows:

| | |
|---|---|
| $Al_2O_3$ | 0.94 mgs./ml |
| $P_2O_5$ | 24.6 mgs./ml |
| $SiO_2$ | 1.11 mgs./ml |
| $Na_2O$ | 0.15 mgs./ml |
| Carbon(C) | 65 mgs./ml |
| Nitrogen(N) | 9.3 mgs./ml |
| Chlorine(Cl) | 7.2 mgs./ml |

The $(TEA)_2O$ content was calculated from the carbon analysis, and the $H_2O$ content was determined by difference. The as-synthesized SAPO composition, referred to as SAPO-5, had the unit empirical formula (anhydrous basis):

$0.05(TEA):(Si_{0.22}Al_{0.45}P_{0.33})O_2;$ based on the mole ratios of oxides of:

$0.985Al_2O_3:0.716P_2O_5:0.97SiO_2:0.109(TEA)_2O.$

A portion of the SAPO-5 composition was analyzed chemically and found to contain: 6.9 wt.% C; 1.0 wt.% N; 16.3 wt.% $SiO_2$; 28.9 wt.% $Al_2O_3$; 38.3 wt.% $P_2O_5$; and 14.4 wt.% LOI (Loss on Ignition). This gave a product, expressed in molar ratios of:

$1.0Al_2O_3:0.95P_2O_5:0.96SiO_2:0.13(TEA)_2O:0.8H_2O$ which corresponds to the unit empirical formula (anhydrous basis):

$0.053(TEA):(Si_{0.2}Al_{0.41}P_{0.39})O_2$

The X-ray powder diffraction pattern of this SAPO-5 was characterized by the following data:

TABLE A

| $2\theta$ | d | $100 \times I/I_o$ |
|---|---|---|
| 7.5 | 11.8 | 100 |
| 12.9 | 6.86 | 12 |
| 15.0 | 5.91 | 26 |
| 19.9 | 4.46 | 61 |
| 21.1 | 4.21 | 53 |
| 22.45 | 3.96 | 77 |
| 24.8 | 3.59 | 5 |
| 26.0 | 3.43 | 30 |
| 29.1 | 3.07 | 17 |
| 30.15 | 2.96 | 19 |
| 33.65 | 2.66 | 5 |
| 34.65 | 2.59 | 16 |

This X-ray pattern and all other X-ray patterns appearing hereinafter were obtained using standard X-ray powder diffraction techniques. The radiation source was a high-intensity, copper target, X-ray tube operated at 50 Kv and 40 ma. The diffraction pattern from the copper K$\alpha$ radiation and graphite monochromator is suitably recorded by an X-ray spectrometer scintillation counter, pulse height analyzer and strip chart recorder. Flat compressed powder samples are scanned at $2\theta$(2 theta) per minute, using a two second time constant. Interplanar spacings (d) in Angstrom units are obtained from the position of the diffraction peaks expressed as $2\theta$ (theta) where theta is the Bragg angle as observed on the strip chart. Intensities were determined from the heights of diffraction peaks after subtracting background, "$I_o$" being the intensity of the strongest line or peak, and "I" being the intensity of each of the other peaks.

As will be understood by those skilled in the art the determination of the parameter 2 theta is subject to both human and mechanical error, which in combination, can impose an uncertainty of about ±0.4° on each reported value of 2 theta. This uncertainty is, of course, also manifested in the reported values of the d-spacings, which are calulated from the 2 theta values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m, w and vw which represent very strong, strong, medium, weak and very weak, respectively.

EXAMPLE 2 (SAPO-5)

(a) SAPO-5 was prepared by combining 18.44 grams of 85 wt. % orthophosphoric acid ($H_3PO_4$) and 11.56 grams of water, to which was added 11.04 grams of hydrated aluminum oxide (a pseudo-boehmite phase, 74.2 wt. % $Al_2O_3$ and 25.8 wt. % $H_2O$), and stirred until homogeneous. To this mixture was added a dispersion of 2.08 grams of a fumed silica (92.8 wt. % $SiO_2$ and 7.2 wt. % $H_2O$), in 81.64 grams of an aqueous solution of 40% tetra-n-propylammonium hydroxide (TPAOH), and the mixture stirred until homogeneous. The composition of the final reaction mixture in molar oxide ratios was:

$Al_2O_3:P_2O_5:0.4SiO_2:(TPA)_2O:50H_2O$

A portion of the reaction mixture was sealed in a stainless steel pressure vessel lined with an inert plastic material and heated in an oven at 225° C. at autogeneous pressure for 24 hours. The solid reaction product was recovered by centrifuging and washing with water, and dried in air at room temperature. The above product has an X-ray powder diffraction pattern characterized by the following data:

TABLE B

| 2θ | d | 100 × I/I₀ |
|---|---|---|
| 7.4 | 11.95 | 100 |
| 12.9 | 6.86 | 11 |
| 14.9 | 5.95 | 25 |
| 19.7 | 4.51 | 51 |
| 21.1 | 4.21 | 67 |
| 22.3 | 3.99 | 92 |
| 24.8 | 3.59 | 5 |
| 25.8 | 3.453 | 37 |
| 28.9 | 3.089 | 21 |
| 29.9 | 2.988 | 22 |
| 33.6 | 2.667 | 5 |
| 34.4 | 2.607 | 16 |
| 36.8 | 2.442 | 3 |
| 37.6 | 2.392 | 9 |
| 41.5 | 2.176 | 3 |
| 42.2 | 2.141 | 5 |
| 42.8 | 2.113 | 3 |
| 43.5 | 2.080 | 3 |
| 44.9 | 2.019 | 3 |
| 47.6 | 1.910 | 8 |

Chemical analysis established that the solids (product) comprised: 8.0 wt. % C; 0.97 wt. % N; 7.22 wt. % $SiO_2$; 33.5 wt. % $Al_2O_3$; 44.5 wt. % $P_2O_5$; and 12.8 wt. % LOI. This gave a product composition in terms of molar oxide ratios of:

$0.085(TPA)_2O:0.37SiO_2:1.0Al_2O_3:0.96P_2O_5:0.26H_2O$

In terms of moles of template per average mole of tetrahedral units (sometimes referred to as $TO_2$, i.e., $(Si_xAl_yP_z)O_2$ units), the composition was (anhydrous basis):

$0.040(TPA):(Si_{0.08}Al_{0.47}P_{0.45})O_2$ (b) A portion of solid crystalline product was calcined in air at about 600° C. for 1 hour. The calcined product had an X-ray powder diffraction pattern characterized by the following data:

TABLE C

| 2θ | d | 100 × I/I₀ |
|---|---|---|
| 7.5 | 11.79 | 100 |
| 13.0 | 6.81 | 27 |
| 15.0 | 5.91 | 11 |
| 19.9 | 4.46 | 42 |
| 21.3 | 4.17 | 62 |
| 22.6 | 3.93 | 96 |
| 25.0 | 3.56 | 4 |
| 26.0 | 3.427 | 44 |
| 29.2 | 3.058 | 23 |
| 30.2 | 2.959 | 23 |
| 33.8 | 2.652 | 6 |
| 34.6 | 2.592 | 17 |

(c) Adsorption capacities were measured on the calcined product of part (b), above, using a standard McBain-Bakr gravimetric adsorption apparatus. The following data were obtained on a sample activated at 350° C.

| | Kinetic Diameter, A | Pressure, Torr | Temp., °C. | Wt. % Adsorbed |
|---|---|---|---|---|
| O₂ | 3.46 | 100 | −183 | 14.5 |
| O₂ | 3.46 | 750 | −183 | 19.8 |
| Cyclohexane | 6.0 | 60 | 24 | 10.9 |
| Neopentane | 6.2 | 743 | 24 | 7.6 |
| H₂O | 2.65 | 4.6 | 24 | 14.7 |
| H₂O | 2.65 | 20.0 | 24 | 31.3 |

The pore size of the calcined product was thus determined to be greater than about 6.2A, as shown by adsorption of neopentane which has a kinetic diameter of 6.2A.

(d) Ion-exchange studies were carried out on 1.0 gram of the product of part (a) calcined in air for 2 hours at 600° C. The sample was stirred at room temperature for 10 minutes with 25 cubic centimeters (cc) of a saturated NaCl solution containing 1.0 gram of NaHCO₃. After being washed with 1 liter of hot water and then 1 liter of cold water, the product was dried in air at 100° C. for 2 hours. Chemical analysis of the product showed: 29.5 wt. % $Al_2O_3$; 39.0 wt. % $P_2O_5$; 7.6 wt. % $SiO_2$ and 3.3 wt. % $Na_2O$. This corresponds to a product composition in molar oxide ratios of $1.0Al_2O_3:0.95P_2O_5:0.44SiO_2:0.18Na_2O$

SAPO-11

SAPO-11, as referred to herein, comprises a silicoaluminophosphate material having a three-dimensional microporous crystal framework structure of $[PO_2]$, $[AlO_2]$ and $[SiO_2]$ tetrahedral units whose unit empirical formula on an anhydrous basis is:

$mR:(Si_xAl_yP_z)O_2$ wherein "R" represents at least one organic templating agent present in the intracrystalline pore system; "m" represents the moles of "R" present per mole of $(Si_xAl_yP_z)O_2$ and has a value from zero to about 0.3, "x", "y" and "z" represent respectively, the mole fractions of silicon, aluminum and phosphorus, said mole fractions being within the compositional area bounded by points A, B, C, D and E on the ternary diagram which is FIG. 1 or preferably within the area bounded by points a, b, c, d and e on the ternary diagram which is FIG. 2, and said silicoaluminophosphate having a characteristic X-ray powder diffraction pattern which contains at least the d-spacings (as-synthesized and calcined) set forth below in Table III. When SAPO-11 is in the as-synthesized form "m" preferably has a value of from 0.02 to 0.3.

TABLE III

| 2θ | d | Relative Intensity |
|---|---|---|
| 9.4–9.65 | 9.41–9.17 | m |
| 20.3–20.6 | 4.37–4.31 | m |
| 21.0–21.3 | 4.23–4.17 | vs |
| 22.1–22.35 | 4.02–3.99 | m |
| 22.5–22.9 (doublet) | 3.95–3.92 | m |
| 23.15–23.35 | 3.84–3.81 | m–s |

All of the as-synthesized SAPO-11 compositions for which X-ray powder diffraction data which have been obtained to data have patterns which are within the generalized pattern of the Table IV below.

TABLE IV

| 2θ | | d | 100 × I/I₀ |
|---|---|---|---|
| 8.05–8.3 | | 10.98–10.65 | 20–42 |
| 9.4–9.65 | | 9.41–9.17 | 36–58 |
| 13.1–13.4 | | 6.76–6.61 | 12–16 |
| 15.6–15.85 | | 5.68–5.59 | 23–38 |
| 16.2–16.4 | | 5.47–5.40 | 3–5 |
| 18.95–19.2 | | 4.68–4.62 | 5–6 |
| 20.3–20.6 | | 4.37–4.31 | 36–49 |
| 21.0–21.3 | | 4.23–4.17 | 100 |
| 22.1–22.35 | | 4.02–3.99 | 47–59 |
| 22.5–22.9 | (doublet) | 3.95–3.92 | 55–60 |
| 23.15–23.35 | | 3.84–3.81 | 64–74 |
| 24.5–24.9 | (doublet) | 3.63–3.58 | 7–10 |
| 26.4–26.8 | (doublet) | 3.38–3.33 | 11–19 |
| 27.2–27.3 | | 3.28–3.27 | 0–1 |
| 28.3–28.5 | (shoulder) | 3.15–3.13 | 11–17 |
| 28.6–28.85 | | 3.121–3.094 | |
| 29.0–29.2 | | 3.079–3.058 | 0–3 |
| 29.45–29.65 | | 3.033–3.013 | 5–7 |
| 31.45–31.7 | | 2.846–2.823 | 7–9 |
| 32.8–33.1 | | 2.730–2.706 | 11–14 |
| 34.1–34.4 | | 2.629–2.607 | 7–9 |
| 35.7–36.0 | | 2.515–2.495 | 0–3 |
| 36.3–36.7 | | 2.475–2.449 | 3–4 |
| 37.5–38.0 | (doublet) | 2.398–2.368 | 10–13 |
| 39.3–39.55 | | 2.292–2.279 | 2–3 |
| 40.3 | | 2.238 | 0–2 |
| 42.2–42.4 | | 2.141–2.132 | 0–2 |
| 42.8–43.1 | | 2.113–2.099 | 3–6 |
| 44.8–45.2 | (doublet) | 2.023–2.006 | 3–5 |
| 45.9–46.1 | | 1.977–1.969 | 0–2 |
| 46.8–47.1 | | 1.941–1.929 | 0–1 |
| 48.7–49.0 | | 1.870–1.859 | 2–3 |
| 50.5–50.8 | | 1.807–1.797 | 3–4 |
| 54.6–54.8 | | 1.681–1.675 | 2–3 |
| 55.4–55.7 | | 1.658–1.650 | 0–2 |

EXAMPLE 3 (SAPO-11)

(a) SAPO 11 was prepared by forming a reaction mixture by combining 160 grams of water and 90.7 grams of aluminum isopropoxide (Al(i-OC$_3$H$_7$)$_3$) to which was added 51.3 grams of 85 wt. % orthophosphoric acid (H$_3$PO$_4$) with stirring. To this mixture was added 1.4 grams of a fumed silica (95 wt. % SiO$_2$ and 5 wt. % H$_2$O) and then, after stirring, 7.4 grams of di-n-propylamine (Pr$_2$NH) was added to one-third by weight of the above mixture. The final mixture was stirred until homogeneous. The composition of the final reaction mixture in molar oxide ratios was:

1.0Pr$_2$NH:0.1SiO$_2$:Al$_2$O$_3$:P$_2$O$_5$:42H$_2$O

In terms of molar proportions, in which the silicon, aluminum and phosphorus sources are expressed as TO$_2$, i.e., (Si$_x$Al$_y$P$_z$)O$_2$, units, the reaction mixture can be expressed as:

0.24(Pr$_2$NH):(Si$_{0.02}$Al$_{0.49}$Si$_{0.49}$)O$_2$:10.2H$_2$O

The reaction mixture was sealed in a stainless steel pressure vessel lined with polytetrafluoroethylene and heated in an oven at 150° C. at the autogenous pressure for 133 hours. The solid reaction product was recovered by centrifugation, washed with water, and dried in air at room temperature. Chemical analysis established the composition comprised: 3.5 wt.% C; 0.65 wt.% N; 38.2 wt.% Al$_2$O$_3$; 35.9 wt.% P$_2$O$_5$; 2.9 wt.% SiO$_2$; 17.7 wt.% LOI; and this gave a product composition (anhydrous basis) for the SAPO-11 as follows:

0.037Pr$_2$NH:(Si$_{0.04}$Al$_{0.57}$P$_{0.39}$)O$_2$ or, in terms of mole ratios of oxides:

0.13Pr$_2$NH:Al$_2$O$_3$:0.68P$_2$O$_5$:0.13SiO$_2$:2.1H$_2$O

The as-synthesized composition had an X-ray powder diffraction pattern characterized by the following data:

TABLE D

| 2θ | d | 100 × I/I₀ |
|---|---|---|
| 8.05 | 10.98 | 20 |
| 9.4 | 9.41 | 36 |
| 13.1 | 6.76 | 13 |
| 15.65 | 5.66 | 23 |
| 16.3 | 5.44 | 3 |
| 18.95 | 4.68 | 5 |
| 20.4 | 4.35 | 36 |
| 21.0 | 4.23 | 100 |
| 22.1 | 4.02 | 54 |
| 22.5 | 3.95 | } 56 |
| 22.7 sh* | 3.92 | |
| 23.15 | 3.84 | 66 |
| 24.5 | 3.63 | } 8 |
| 24.7 | 3.60 | |
| 26.4 | 3.38 | 19 |
| 27.2 | 3.28 | 1 |
| 28.6 | 3.121 | 14 |
| 29.0 | 3.079 | 3 |
| 29.45 | 3.033 | 6 |
| 31.5 | 2.840 | 8 |
| 32.8 | 2.730 | 13 |
| 34.1 | 2.629 | 8 |
| 35.75 | 2.512 | 3 |
| 36.3 | 2.475 | 3 |
| 37.5 | 2.398 | } 10 |
| 37.8 | 2.380 | |
| 39.3 | 2.292 | 3 |
| 40.3 | 2.238 | 2 |
| 42.8 | 2.113 | 6 |
| 44.9 | 2.019 | 4 |
| 46.8 | 1.941 | 1 |
| 48.7 | 1.870 | 2 |
| 50.5 | 1.807 | 3 |
| 54.6 | 1.684 | 4 |

*sh = shoulder (b) A portion of the product of part (a) was calcined in air at 500° C. for 1 hour, then at 600° C. for 1 hour. The calcined product has an X-ray powder diffraction pattern characterized by the following data:

TABLE E

| 2θ | d | 100 × I/I₀ |
|---|---|---|
| 8.1 | 10.9 | 54 |
| 9.6 | 9.2 | 53 |
| 12.8 | 6.92 | } 18 |
| 13.05 | 6.78 | |
| 15.85 | 5.59 | } 46 |
| 16.1 (sh) | 5.50 | |
| 19.4 (sh) | 4.58 | } 30 |
| 20.3 | 4.37 | |
| 21.3 | 4.17 | 100 |
| 21.9 (sh) | 4.06 | 39 |
| 22.3 | 3.99 | 75 |
| 22.9 (sh) | 3.88 | 41 |
| 23.3 | 3.82 | 60 |
| 24.1 | 3.69 | 9 |
| 24.9 | 3.58 | 5 |
| 26.35 | 3.38 | 20 |
| 28.9 | 3.089 | 12 |
| 29.5 | 3.028 | 11 |

TABLE E-continued

| 2θ | d | 100 × I/I₀ |
|---|---|---|
| 30.3 | 2.950 | 5 |
| 31.7 | 2.823 | 9 |
| 32.75 | 2.734 | 14 |
| 34.0 | 2.637 | 4 |
| 34.55 | 2.596 | 5 |
| 36.2 | 2.481 | 7 |
| 37.1 | 2.423 | 2 |
| 37.8 | 2.380 | 10 |
| 39.4 | 2.287 | 2 |
| 41.0 | 2.201 | 1 |
| 43.2 | 2.094 | 3 |
| 44.7 | 2.027 | 3 |
| 48.3 | 1.884 | 1 |
| 51.2 | 1.784 | 2 | sh = shoulder (c) Adsorption capacities were measured on the calcined product of (b) using a standard McBain-Bakr gravimetric adsorption apparatus. The following data were obtained on a sample activated at 350° C.

| | Kinetic Diameter, Å | Pressure, Torr | Temp, °C. | Wt. % Adsorbed |
|---|---|---|---|---|
| $O_2$ | 3.46 | 102 | −183 | 7.3 |
| $O_2$ | 3.46 | 743 | −183 | 15.3 |
| Cyclohexane | 6.0 | 52 | 24.6 | 6.9 |
| Neopentane | 6.2 | 300 | 24.8 | 1.7 |
| $H_2O$ | 2.65 | 4.6 | 23.9 | 11.4 |
| $H_2O$ | 2.65 | 20.2 | 23.2 | 18.0 |

The pore size of the calcined product was determined to be between about 6.0 Å and about 6.2 Å, as shown by adsorption of cyclohexane, kinetic diameter of 6.0 Å, and negligible adsorption of neopentane, kinetic diameter of 6.2 Å.

SAPO-16

SAPO-16, as referred to herein, comprises a silicoaluminophosphate material having a three-dimensional microporous crystal framework structure of $[PO_2]$, $[AlO_2]$ and $[SiO_2]$ tetrahedral units whose unit empirical formula on an anhydrous basis is:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to about 0.3, "x", "y" and "z" represent respectively, the mole fractions of silicon, aluminum and phosphorus, said mole fractions being within the compositional area bounded by points A, B, C, D and E on the ternary diagram which is FIG. 1, or preferably within the area bounded by points a, b, c, d and e on the ternary diagram which is FIG. 2, said SAPO having a characteristic X-ray powder diffraction pattern (as-synthesized and calcined) which contains at least the d-spacings set forth below in Table V. When SAPO-16 is in the as-synthesized form "m" preferably has a value of from 0.02 to 0.3.

TABLE V

| 2θ | d | Relative Intensity |
|---|---|---|
| 11.3–11.5 | 7.83–7.69 | m |
| 18.7–18.9 | 4.75–4.70 | m |
| 21.9–22.3 | 4.06–3.99 | vs |
| 26.5–27.0 | 3.363–3.302 | w–m |

TABLE V-continued

| 2θ | d | Relative Intensity |
|---|---|---|
| 29.7–30.05 | 3.008–2.974 | w–m |

All of the as-synthesized SAPO-16 compositions for which X-ray powder diffraction data have presently been obtained have patterns which are within the generalized pattern of Table VI, below.

TABLE VI

| 2θ | d | 100 × I/I₀ |
|---|---|---|
| 11.3–11.5 | 7.83–7.69 | 52–66 |
| 17.0–17.5 | 5.22–5.07 | 0–4 |
| 18.7–18.9 | 4.75–4.70 | 50–58 |
| 21.9–22.3 | 4.06–3.99 | 100 |
| 26.5–27.0 | 3.363–3.302 | 15–23 |
| 29.1–29.4 | 3.069–3.038 | 5–13 |
| 29.7–30.05 | 3.008–2.974 | 23–26 |
| 32.7–32.9 | 2.739–2.722 | 0–3 |
| 34.4–34.8 | 2.607–2.578 | 2–4 |
| 38.0–38.3 | 2.368–2.350 | 7–9 |
| 39.9–40.3 | 2.259–2.238 | 0–7 |
| 44.3–44.45 | 2.045–2.038 | 0–4 |
| 48.5–48.7 | 1.877–1.870 | 6–8 |
| 49.0–49.4 | 1.859–1.845 | 0–2 |
| 52.3–52.5 | 1.749–1.743 | 0–2 |
| 54.8–54.9 | 1.675–1.672 | 0–2 |

EXAMPLE 4 (SAPO-16)

SAPO-16 was prepared by combining 46.0 grams of 85 wt. % orthophosphoric acid and 100 grams of water which was added to 81.7 grams of aluminum isopropoxide ($Al(i-OC_3H_7)_3$) and 5.0 grams of water and the mixture stirred well. To the above mixture were added 12.0 grams of an aqueous sol containing 30 wt. % $SiO_2$, and 5.0 additional grams of water, and the mixture stirred until homogeneous. To one-half (by weight) of this mixture were added 11.1 grams of quinuclidine, $C_7H_{13}N$,(QN) and 21.9 grams of water, and the mixture stirred until homogeneous. The composition of the final reaction mixture in molar oxide ratios was:

$$1.0QN:Al_2O_3:P_2O_5:0.3SiO_2:50H_2O$$

Part of the reaction mixture was sealed in a stainless steel pressure vessel having an inert plastic liner and heated in an oven at 200° C. at autogenous pressure for 48 hours. The solid reaction product, denominated SAPO-16, was recovered by centrifugation, washed with water, and dried in air at 100° C. X-ray analysis was performed on a portion of the solids which passed through a 100 mesh sieve. The SAPO-16 product had an X-ray powder diffraction pattern characterized by the following data:

TABLE F

| 2θ | d | 100 × I/I₀ |
|---|---|---|
| 11.45 | 7.73 | 54 |
| 17.35 | 5.11 | 4 |
| 18.8 | 4.72 | 51 |
| 22.05 | 4.03 | 100 |
| 26.65 | 3.345 | 20 |
| 29.2 | 3.058 | 6 |
| 29.85 | 2.993 | 25 |
| 32.7 | 2.739 | 3 |
| 34.8 | 2.578 | 4 |
| 38.05 | 2.365 | 8 |
| 39.9 | 2.259 | 3 |
| 44.4 | 2.040 | 2 |
| 48.5 | 1.877 | 6 |

TABLE F-continued

| 2θ | d | 100 × I/I₀ |
|---|---|---|
| 49.0 | 1.859 | 1 |
| 52.4 | 1.746 | 2 |
| 54.8 | 1.675 | 2 |

EXAMPLE 5 (SAPO-16)

A silicoaluminophosphate molecular sieve was prepared by forming a mixture of combining 132.8 grams of aluminum isopropoxide [Al(i-C₃H₇O)₃], 177.1 grams of water and Ludox LS (30.1 grams). To this mixture was added 57.7 grams of 85 wt.% orthophosphoric acid (H₃PO₄). The mixture was stirred until a homogeneous mixture was observed. To this mixture was added 27.8 grams of quinuclidine (QN) in 50.0 grams of water. The resulting mixture was stirred until a homogenous mixture was observed. The composition of the final reaction mixture, expressed in terms of molar ratios was:

$$1.0(QN):0.6SiO_2:1.3Al_2O_3:P_2O_5:60H_2O$$

A portion of the reaction mixture was sealed in a stainless steel pressure vessel lined with polytetrafluoroethylene. The mixture was then heated in an oven at 200° C. at the autogenous pressure for about 48 hours. The silicoaluminophosphate product (i.e., the solid reaction product) was recovered by centrifugal filtration, washed with water, and dried in air at a temperature of about 100° C. This product was then calcined in air at 550° C. for a period of about 12 hours. The as-synthesized and calcined product had an X-ray powder diffraction pattern characterized by the general diffraction X-ray pattern set forth in Table VII.

TABLE VII

| 2θ | d | 100 × I/I₀ |
|---|---|---|
| 11.6 | 7.6 | 60 |
| 19.0 | 4.67 | 56 |
| 22.3 | 3.99 | 100 |
| 27.0 | 3.302 | 20 |
| 29.5 | 3.028 | 8 |
| 30.1 | 2.969 | 26 |
| 32.9 | 2.722 | 4 |
| 34.8 | 2.578 | 3 |
| 38.2 | 2.356 | 8 |
| 40.3 | 2.238 | 5 |
| 46.7 | 1.870 | 7 |

SAPO-17

SAPO-17, as referred to herein, comprises a silicoaluminophosphate material having a three-dimensional microporous crystal framework structure of [PO₂], [AlO₂] and [SiO₂] tetrahedral units, and whose unit emprirical formula on an anhydrous basis is:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3, "x", "y" and "z" represent respectively, the mole fractions of silicon, aluminum and phosphorous said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern (as-synthesized ad calcined) which contains at least the d-spacings set forth below in Table VIII. When SAPO-17 is in the as-synthesized form "m" preferably has a value of from 0.02 to 0.30.

TABLE VIII

| 2θ | d | Relative Intensity |
|---|---|---|
| 7.70–7.75 | 11.5–11.4 | vs |
| 13.4 | 6.61 | s–vs |
| 15.5–15.55 | 5.72–5.70 | s |
| 19.65–19.7 | 4.52–4.51 | w–m |
| 20.5–20.6 | 4.33–4.31 | vs |
| 31.85–32 | 2.810–2.797 | w–m |

All of the as-synthesized SAPO-17 compositions for which X-ray powder diffraction data have presently been obtained have patterns which are within the generalized pattern of Table IX below.

TABLE IX

| 2θ | d | 100 × I/I₀ |
|---|---|---|
| 7.70 | 11.5–11.45 | 100 |
| 9.8 | 9.03 | 5–36 |
| 11.8 | 7.50 | 1 |
| 13.4 | 6.61 | 60–95 |
| 14.2 | 6.24 | 6 |
| 15.5 | 5.72–5.70 | 37–65 |
| 16.6 | 5.34 | 19 |
| 18.0 | 4.93 | 18–25 |
| 19.65–19.7 | 4.52–4.51 | 10–39 |
| 20.5–20.6 | 4.33–4.31 | 80–100 |
| 21.4 (sh) | 4.15 | |
| 22.5 | 3.95 | 7 |
| 23.3–23.4 | 3.82–3.80 | 20–38 |
| 23.8 | 3.74 | 32 |
| 25.4 | 3.507 | 15–38 |
| 27.0 | 3.302 | 25–49 |
| 27.4 | 3.255 | 5–9 |
| 28.7 | 3.110 | 5–18 |
| 30.6 (sh) | 2.921 | sh–5 |
| 31.3–31.35 | 2.858–2.853 | 10–20 |
| 31.85–32.0 | 2.810–2.797 | 20–48 |
| 33.4–33.55 | 2.683–2.671 | 5–19 |
| 35.9–36.05 | 2.501–2.491 | 8–10 |
| 36.4–36.45 | 2.468–2.465 | 4–10 |
| 40.3 | 2.238 | 1 |
| 43.7 | 2.071 | 11 |
| 45.9 | 1.977 | 5 |
| 49.6–49.7 | 1.838–1.834 | 5–15 |
| 52.0–52.3 | 1.704–1.749 | 10–15 |
| 53.8–53.9 | 1.704–1.701 | 2–5 |
| 55.45–55.5 | 1.657–1.656 | 5–11 |

EXAMPLE 6 (SAPO-17)

SAPO-17 was formed from a reaction mixture formed by combining 57.7 grams of 85 wt. % orthophosphoric acid and 130.0 grams of water with 132.8 grams of aluminum isopropoxide (Al(i-OC₃H₇)₃) and mixing well. To this mixture were added 47.0 grams of water and 30.1 grams of an aqueous sol containing 30 wt. % SiO₂, and the mixture stirred until homogeneous.

To this mixture was added a solution of 27.8 grams of quinuclidine, $C_7H_{13}N$, (QN) in 50.0 grams of water, and the mixture stirred until homogeneous. The composition of the final reaction mixture in molar oxide ratios was:

$$QN:0.6SiO_2:1.3Al_2O_3:P_2O_5:60H_2O$$

Part of the reaction mixture was placed in a stainless steel pressure vessel lined with an inert material and heated in an oven at 200° C. at autogenous pressure for 338 hours. The solid reaction product was recovered by centrifugation, washed with water, and dried in air at 100° C. The SAPO-17 product had an X-ray powder diffraction pattern characterized by the following data:

TABLE G

| 2θ | | d | 100 × I/I$_o$ |
|---|---|---|---|
| 7.75* | | 11.4 | 100 |
| 9.8 | | 9.03 | 5 |
| 13.4* | | 6.61 | 60 |
| 15.55* | | 5.70 | 65 |
| 16.7 | | 5.31 | 5 |
| 18.0 | | 4.93 | 25 |
| 19.7 | | 4.51 | 10 |
| 20.6* | | 4.31 | 100 |
| 21.4 | (sh) | 4.15 | |
| 23.4 | | 3.80 | 20 |
| 25.4 | | 3.507 | 15 |
| 27.0 | | 3.302 | 24 |
| 27.4 | | 3.255 | 5 |
| 28.7 | | 3.110 | 5 |
| 30.6 | (sh) | 2.921 | |
| 31.35 | | 2.853 | 10 |
| 32.0 | | 2.797 | 20 |
| 33.4 | | 2.683 | 5 |
| 36.05 | | 2.491 | 10 |
| 36.45 | | 2.465 | 10 |
| 40.0** | | 2.254 | 40 |
| 40.3** | | 2.238 | |
| 45.9 | | 1.977 | 5 |
| 49.7 | | 1.834 | 5 |
| 52.3** | | 1.749 | 15 |
| 53.9 | | 1.701 | 5 |
| 55.5 | | 1.656 | 5 |

*probably contains peak from another composition
**contains peak from another composition

EXAMPLE 7 (SAPO-17)

(a) SAPO-17 was prepared using cyclohexylamine (instead of the quinuclidine of Ex. 6) as the templating agent and decreasing the relative proportion of silica in the gel. SAPO-17 was prepared by combining 81.7 grams of aluminum isopropoxide [Al(i-OC$_3$H$_7$)$_3$] with a solution of 46.1 grams of 85 wt. % orthophosphoric acid (H$_3$PO$_4$) in 159.6 grams of H$_2$O, stirring until homogeneous, and then adding 4.0 grams of an aqueous silica sol containing 30 wt.% SiO$_2$. The resulting mixture was stirred until it was homogeneous. To this mixture was added 19.8 grams of cyclohexylamine (CHA), and the mixture stirred until homogeneous. The composition of the final reaction mixture in molar oxide ratios was:

$$1.0CHA:0.1SiO_2:Al_2O_3:P_2O_5:50H_2O$$

A portion of the reaction mixture was sealed in a stainless steel pressure vessel lined with polytetrafluoroethylene and heated in an oven at 200° C. at the autogenous pressure for 50 hours. The solid reaction product was recovered by filtration, washed with water, and dried in air at 100° C. The composition of the product was found to be: 9.5 wt.% C; 1.6 wt.% SiO$_2$; 37.8 wt.% Al$_2$O$_3$; 39.9 wt.% P$_2$O$_5$; and 19.8 wt.% LOI; corresponding to the formula (anhydrous basis):

$$0.103CHA:(Si_{0.02}Al_{0.56}P_{0.42})O_2,$$

or in terms of molar oxide ratios:

$$0.18(CHA)_2O:Al_2O_3:0.76P_2O_5:0.07SiO_2$$

The SAPO-17 product contained impurities and had an X-ray powder diffraction pattern characterized by the following data:

TABLE H

| 2θ | d | 100 × I/I$_o$ |
|---|---|---|
| 7.7 | 11.5 | 100 |
| 9.8 | 9.03 | 36 |
| 10.9* | 8.12 | 9 |
| 11.8 | 7.50 | 1 |
| 13.4** | 6.61 | 95 |
| 14.2 | 6.24 | 6 |
| 15.5 | 5.72 | 37 |
| 16.6 | 5.34 | 19 |
| 17.4* | 5.10 | 8 |
| 18.0 | 4.93 | 18 |
| 19.65 | 4.52 | 39 |
| 20.5 | 4.33 | 80 |
| 21.4** | 4.15 | 35 |
| 22.0* | 4.04 | 16 |
| 22.5 | 3.95 | 7 |
| 23.3** | 3.82 | 38 |
| 23.8 | 3.74 | 32 |
| 25.4 | 3.507 | 38 |
| 27.0** | 3.302 | 49 |
| 27.4 | 3.255 | 9 |
| 28.7** | 3.110 | 18 |
| 30.6 | 2.921 | 5 |
| 31.3 | 2.858 | 20 |
| 31.85 | 2.810 | 48 |
| 32.2* | 2.780 | sh |
| 33.55 | 2.671 | 19 |
| 34.6* | 2.592 | 1 |
| 35.9** | 2.501 | 8 |
| 36.4 | 2.468 | 4 |
| 37.4 | 2.404 | 2 |
| 37.9 | 2.374 | 2 |
| 39.8 | 2.265 | 3 |
| 40.3 | 2.238 | 1 |
| 40.9 | 2.206 | 1 |
| 42.1 | 2.146 | 2 |
| 42.6 | 2.122 | 1 |
| 43.7 | 2.071 | 11 |
| 45.6 | 1.989 | 1 |
| 46.5 | 1.953 | 2 |
| 47.8 | 1.903 | 1 |
| 48.7 | 1.870 | 1 |
| 49.3 | 1.848 | sh |
| 49.6 | 1.838 | 15 |
| 52.0 | 1.759 | 10 |
| 53.8 | 1.704 | 2 |
| 55.45 | 1.657 | 11 |

*peak from another composition
**contains peak from another composition (b) The product of (a) was calcined for 4 hours at 550° C. in air. The calcined product had an X-ray powder diffraction pattern characterized by the following data (known impurity peaks have been omitted):

TABLE K

| 2θ | d | 100 × I/I$_o$ |
|---|---|---|
| 7.7 | 11.5 | 92 |
| 9.65 | 9.17 | 32 |
| 11.0* | 8.04 | 3 |
| 11.5 | 7.69 | 10 |
| 13.5** | 6.56 | 100 |
| 13.9 | 6.37 | 21 |

TABLE K-continued

| 2θ | d | 100 × I/I₀ |
|---|---|---|
| 15.6 | 5.68 | 11 |
| 16.65 | 5.32 | 22 |
| 17.5* | 5.07 | 1 |
| 19.0 | 4.67 | 7 |
| 19.4 | 4.58 | 6 |
| 20.7 | 4.29 | 22 |
| 21.45** | 4.14 | 13 |
| 22.1* | 4.02 | 4 |
| 23.5 | 3.79 | 19 |
| 23.7 | 3.75 | sh |
| 24.5 | 3.63 | 19 |
| 27.15 | 3.285 | 17 |
| 28.0 | 3.187 | 5 |
| 30.1 | 2.969 | 1 |
| 30.6 | 2.921 | 3 |
| 31.25 | 2.862 | 14 |
| 32.0 | 2.797 | 9 |
| 33.55 | 2.671 | 6 |
| 35.0 | 2.564 | 2 |
| 36.2 | 2.481 | 3 |
| 39.4 | 2.287 | 2 |
| 40.2 | 2.243 | 1 |
| 41.3 | 2.186 | 2 |
| 41.9 | 2.156 | 1 |
| 42.6 | 2.122 | 3 |
| 43.5 | 2.080 | 1 |
| 46.0 | 1.973 | 1 |
| 46.4 | 1.957 | 1 |
| 47.1 | 1.929 | 2 |
| 47.9 | 1.899 | 2 |
| 50.1 | 1.821 | 5 |
| 51.2 | 1.784 | 5 |
| 52.7 | 1.737 | 1 |
| 55.2 | 1.664 | 2 |

*peak from another composition
**contains peak from another composition (c) Adsorption capacities were measured on the calcined product of part (b) supra using standard McBain-Bakr gravimetric adsorption apparatus. The following data were obtained on a sample activated at 350° C.:

| | Kinetic Diameter, Å | Pressure, Torr | Temp., °C. | Wt. % Adsorbed |
|---|---|---|---|---|
| O₂ | 3.46 | 98.5 | −183 | 21.5 |
| O₂ | 3.46 | 740 | −183 | 29.4 |
| n-hexane | 4.3 | 53.5 | 24 | 10.3 |
| H₂O | 2.65 | 4.6 | 23 | 25.2 |
| H₂O | 2.65 | 19.4 | 24 | 35.0 |
| isobutane | 5.0 | 400 | 24 | 1.1 |

The pore size of the calcined product was determined to be above about 4.3 Å as indicated by adsorption of n-hexane and below about 5.0 Å° as shown by neglible adsorption of isobutane.

SAPO-20

SAPO-20, as referred to herein, comprises a silicoaluminophosphate material having a three-dimensional microporous crystal framework structure of [PO₂], [AlO₂] and [SiO₂] tetrahedral units whose unit empirical formula on an anhydrous basis is:

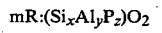

$$mR:(Si_xAl_yP_z)O_2$$

wherein "R" represents at least one organic templating agent present in the intracrystalline pore system; "m" represents the moles of "R" present per mole of (Si$_x$Al$_y$P$_z$)O₂ and has a value of from zero to 0.3, "x", "y" and "z" represent respectively, the mole fractions of silicon, aluminum and phosphorus present as tetrahedral units, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern (as synthesized and calcined) which contains at least the d-spacings set forth below in Table X. In the form as synthesized "m" preferably has a value of from 0.02 to 0.3.

TABLE X

| 2θ | d | Relative Intensity |
|---|---|---|
| 13.7–14.25 | 6.46–6.22 | m |
| 19.55–20.0 | 4.54–4.44 | w-m |
| 24.05–24.45 | 3.700–3.641 | vs |
| 34.35–35.0 | 2.611–2.564 | w |
| 42.5–43.0 | 2.127–2.103 | vw-w |

All of the as-synthesized SAPO-20 compositions for which X-ray powder diffraction data have presently been obtained have patterns which are within the generalized pattern of Table XI.

TABLE XI

| 2θ | d | 100 × I/I₀ |
|---|---|---|
| 13.7–14.25 | 6.46–6.22 | 38–63 |
| 19.55–20.0 | 4.54–4.44 | 25–58 |
| 21.9–22.35 | 4.06–3.98 | 0–9 |
| 24.05–24.45 | 3.700–3.641 | 100 |
| 27.85–28.55 | 3.203–3.126 | 8–17 |
| 31.25–31.8 | 2.862–2.814 | 5–16 |
| 34.35–35.0 | 2.611–2.564 | 12–22 |
| 37.3–37.5 | 2.411–2.398 | 0–3 |
| 39.9–40.4 | 2.259–2.233 | 2–6 |
| 42.5–43.0 | 2.127–2.103 | 3–24 |
| 47.25–47.8 | 1.924–1.903 | 2–8 |
| 51.6–52.2 | 1.771–1.752 | 2–17 |

EXAMPLE 8 (SAPO-20)

(a) SAPO-20 was prepared by adding 1.09 grams of a reactive amorphous precipitated silica (91.4 wt.% SiO₂ and 8.6 wt.% H₂O) to a solution of 14.50 grams of tetramethylammonium hydroxide pentahydrate (TMAOH.5H₂O) in 20.0 grams of water. The mixture was mixed until homogeneous. To this mixture were added 6.12 grams of a hydrated aluminum oxide (a pseudoboehmite phase, 74.2 wt.% Al₂O₃ and 25.8 wt.% H₂O) and 9.55 grams of 85% orthophosphoric acid (H₃PO₄) and 6.21 grams of water and the mixture stirred until homogeneous. The composition of the final reaction mixture in molar oxide ratios was:

1.1Al₂O₃:1.0P₂O₅:1.0(TMA)₂O:0.4SiO₂:50.0H₂O

Part of the reaction mixture was placed in a stainless steel pressure vessel with an inert plastic liner and heated in an oven at 200° C. at autogeneous pressure for 24 hours. The solid reaction product was recovered by filtering, washed with water, and dried in air at room temperature. The SAPO-20 product had an x-ray powder diffraction pattern characterized by the following data:

TABLE XII

| 2θ | d | 100 × I/I₀ |
|---|---|---|
| 14.1 | 6.28 | 39 |
| 19.8 | 4.48 | 49 |
| 22.2 | 4.00 | 6 |
| 24.3 | 3.66 | 100 |
| 28.1 | 3.175 | 11 |

TABLE XII-continued

| 2θ | d | 100 × I/I₀ |
|---|---|---|
| 31.7 | 2.822 | 12 |
| 34.7 | 2.585 | 16 |
| 37.5 | 2.398 | 1 |
| 40.2 | 2.243 | 5 |
| 42.7 | 2.117 | 6 |
| 47.5 | 1.914 | 6 |
| 51.9 | 1.762 | 12 |

(b) Adsorption capacities were measured on the calcined (500° C. for one hour) product using a standard McBain-Bakr gravimetric adsorption apparatus. The following data were obtained on a sample activated at 350° C. in vacuum.

| | Kinetic Diameter, Å | Pressure, Torr | Temp., °C. | Wt. % Adsorbed |
|---|---|---|---|---|
| $O_2$ | 3.46 | 100 | −183 | 0 |
| $O_2$ | 3.46 | 750 | −183 | 0 |
| $H_2O$ | 2.65 | 4.6 | 24 | 32.1 |
| $H_2O$ | 2.65 | 20 | 24 | 39.8 |

The pore size of the calcined product is greater than 2.65 Å as shown by adsorption of $H_2O$, kinetic diameter 2.65 Å, and less than 3.46 Å, as shown by no adsorption of $O_2$, kinetic diameter 3.46 Å.

(c) The above product, after calcination and McBain adsorption studies, had an X-ray powder diffraction pattern characteristic of SAPO-20 (short scan):

TABLE M

| 2θ | d | 100 × I/I₀ |
|---|---|---|
| 14.0 | 6.33 | 100 |
| 19.8 | 4.48 | 38 |
| 22.2 | 4.00 | 8 |
| 24.3 | 3.663 | 95 |
| 28.2 | 3.164 | 23 |
| 31.5 | 2.840 | 18 |
| 34.6 | 2.592 | 20 |

(d) EDAX (energy dispersive analysis by X-ray) microprobe analysis performed in conjunction with SEM (scanning electron microscope) study, on clean crystals having a crystal morphology characteristic of SAPO-20 gives the following analysis, based on relative peak heights:

| | Area Scan | Average of Spot Probes | Range |
|---|---|---|---|
| Si | 0.42 | 0.40 | 0.36–0.43 |
| Al | 1.0 | 1.0 | 1.0 |
| P | 0.77 | 0.79 | 0.76–0.85 |

SAPO-34

SAPO-34, as referred to herein, comprises a silicoaluminophosphate material having a three-dimensional microporous crystal framework structure of $[PO_2]$, $[AlO_2]$ and $[SiO_2]$ tetrahedral units, and whose unit empirical formula on an anhydrous basis is:

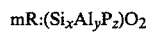

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3, preferably from 0.02 to 0.3, "x", "y" and "z" represent respectively, the mole fractions of silicon, aluminum and phosphorus, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern (as-synthesized and calcined) which contains at least the d-spacings set forth below in Table XIII.

TABLE XIII

| 2θ | d | Relative Intensity |
|---|---|---|
| 9.45–9.65 | 9.36–9.17 | s–vs |
| 16.0–16.2 | 5.54–5.47 | w–m |
| 17.85–18.15 | 4.97–4.89 | w–s |
| 20.55–20.9 | 4.32–4.25 | m–vs |
| 24.95–25.4 | 3.57–3.51 | w–s |
| 30.5–30.7 | 2.931–2.912 | w–s |

All of the as-synthesized SAPO-34 compositions for which X-ray powder diffraction data have presently been obtained have patterns which are within the generalized pattern of Table XIV, below.

TABLE XIV

| 2θ | d | 100 × I/I₀ |
|---|---|---|
| 9.45–9.65 | 9.36–9.17 | 81–100 |
| 12.8–13.05 | 6.92–6.78 | 8–20 |
| 13.95–14.2 | 6.35–6.24 | 8–23 |
| 16.0–16.2 | 5.54–5.47 | 25–54 |
| 17.85–18.15 | 4.97–4.89 | 11–76 |
| 19.0 | 4.67 | 0–2 |
| 20.55–20.9 | 4.32–4.25 | 44–100 |
| 22.05–22.5 | 4.03–3.95 | 0–5 |
| 23.0–23.15 | 3.87–3.84 | 2–10 |
| 24.95–25.4 | 3.57–3.51 | 12–87 |
| 25.8–26.0 | 3.45–3.43 | 14–26 |
| 27.5–27.7 | 3.243–3.220 | 1–4 |
| 28.05–28.4 | 3.181–3.143 | 1–12 |
| 29.2–29.6 | 3.058–3.018 | 3–9 |
| 30.5–30.7 | 2.931–2.912 | 19–75 |
| 31.05–31.4 | 2.880–2.849 | 15–28 |
| 32.2–32.4 | 2.780–2.763 | 1–5 |
| 33.4–33.85 | 2.683–2.648 | 0–6 |
| 34.35–34.65 | 2.611–2.589 | 4–15 |
| 36.0–36.5 | 2.495–2.462 | 2–11 |
| 38.8–38.9 | 2.321–2.315 | 0–2 |
| 39.6–39.7 | 2.276–2.270 | 2–4 |
| 43.1–43.5 | 2.099–2.080 | 3–6 |
| 47.4–47.7 | 1.918–1.907 | 2–6 |
| 48.8–49.2 | 1.866–1.852 | 4–7 |
| 49.9–50.45 | 1.828–1.809 | 0–2 |
| 50.65–51.3 | 1.802–1.781 | 1–8 |
| 53.0–53.25 | 1.728–1.720 | 2–7 |
| 54.25–54.7 | 1.691–1.678 | 0–4 |
| 55.7–55.9 | 1.650–1.645 | 2–5 |

EXAMPLE 9 (SAPO-34)

SAPO-34 was prepared by forming a reaction mixture by combining 28.8 grams of 85 wt.% orthophosphoric acid ($H_3PO_4$) with a mixture of 17.2 grams of a hydrated aluminum oxide (a pseudo-boehmite phase, 74.2 wt.% $Al_2O_3$, 25.8 wt.% $H_2O$) in 18.4 grams of water. To this mixture was added 151.7 grams of an aqueous solution of 40.7 wt.% tetraethylammonium hydroxide (TEAOH) and the mixture stirred until homogeneous. To 81.9 grams of this mixture was added a solution of 11.7 grams of sodium aluminate ($Al_2O_3$:1.2-1$Na_2O$:3.2$H_2O$) in 23.0 grams of water and 40.0 grams of an aqueous sol of 30 wt.% $SiO_2$, and the mixture stirred until homogeneous. The composition of the final reaction mixture in molar oxide ratios was:

1.6(TEA)$_2$O:1.2Na$_2$O:4SiO$_2$:2Al$_2$O$_3$:P$_2$O$_5$:112H$_2$O

Part of the reaction mixture was sealed in a stainless steel pressure vessel having an inert plastic liner, and heated in an oven at 200° C. at autogeneous pressure for 168 hours. The solid reaction product was recovered by filtration, washed with water, and dried in air at 110° C. The crystalline product was impure but the major product, SAPO-34, had an X-ray powder diffraction pattern characterized by the following data:

TABLE N

| 2θ | d | 100 × I/I$_o$ |
| --- | --- | --- |
| 9.6 | 9.21 | 100 |
| 13.0 | 6.81 | 17 |
| 14.05 | 6.30 | 23 |
| 16.1 | 5.50 | 33 |
| 17.85 | 4.97 | 75 |
| 19.0 | 4.67 | 2 |
| 20.7 | 4.29 | 99 |
| 22.05 | 4.03 | 4 |
| 23.1 | 3.85 | 10 |
| 24.95 | 3.57 | 76 |
| 26.0 | 3.43 | 19 |
| 27.7 | 3.220 | 3 |
| 28.15 | 3.170 | 12* |
| 29.4 | 3.038 | 4 |
| 30.7 | 2.912 | 67 |
| 31.05 | 2.880 | 28 |
| 32.4 | 2.763 | 2 |
| 33.4 | 2.683 | 6 |
| 34.55 | 2.596 | 14 |
| 36.0 | 2.495 | 11 |
| 39.7 | 2.270 | 4 |
| 43.4 | 2.085 | 3 |
| 47.6 | 1.910 | 6 |
| 48.8 | 1.866 | 7 |
| 49.2 | 1.852 | 5 |
| 50.65 | 1.802 | 8 |
| 53.2 | 1.722 | 6 |
| 54.25 | 1.691 | 4 |
| 55.9 | 1.645 | 4 |

*contains peak from an impurity.

By chemical analysis, the composition of the solids product was established to be 2.8 wt.% C; 0.5 wt.% N; 37.0 wt.% SiO$_2$; 27.6 wt.% Al$_2$O$_3$; 12.2 wt.% P$_2$O$_5$; 7.4 wt.% Na$_2$O; and 15.9 wt.% LOI; which gave an overall product composition in molar oxide ratios of:

0.05(TEA)$_2$O:2.3SiO$_2$:0.4Na$_2$O:Al$_2$O$_3$:0.3P$_2$O$_5$:2.4-H$_2$O.

EXAMPLE 10 (SAPO-34)

(a) SAPO-34 was prepared by combining 81.7 grams of aluminum isopropoxide (Al(i-OC$_3$H$_7$)$_3$) with a solution of 46.1 grams of 85 wt.% orthophosphoric acid in 104.9 grams of water, while stirring. To this mixture were added 12 grams of an aqueous sol of 30 wt.% SiO$_2$ and 5 grams of water, and the mixture stirred until homogeneous. To this mixture was added 73.7 grams of an aqueous solution of 40 wt.% tetraethylammonium hydroxide (TEAOH). One half by weight of this mixture was combined with 36.8 grams of 40% TEAOH, and the mixture stirred until homogeneous. The composition of the final reaction mixture in molar oxide ratios was:

(TEA)$_2$O:0.3SiO$_2$:Al$_2$O$_3$:P$_2$O$_5$:50.0H$_2$O

The reaction mixture was placed in a stainless steel pressure vessel lined with an inert plastic material (polytetrafluoroethylene) and heated in an oven at 200° C. at autogeneous pressure for 120 hours. The solid reaction product (SAPO-34) was recovered by centrifugation, washed with water, and dried in air at 100° C. By chemical analysis, the product was established to comprise 10.5 wt.% C; 1.6 wt.% N; 34.1 wt.% Al$_2$O$_3$; 39.2 wt.% P$_2$O$_5$; 6.8 wt.% SiO$_2$; and 19.2 wt.% LOI; which gave a product composition in molar oxide ratios of:

0.17(TEA)$_2$O:0.33SiO$_2$:Al$_2$O$_3$:0.82P$_2$O$_5$0.40H$_2$O, which corresponds to the formula (anhydrous basis):

0.09(TEA).(Si$_{0.08}$Al$_{0.51}$P$_{0.41}$)O$_2$.

The above product had an X-ray powder diffraction pattern which identified it as SAPO-34.

(b) A portion of the SAPO-34 of part (a) was calcined in air at 550° C. for 2 hours. Adsorption capacities were measured on this calcined product using a standard McBain-Bakr gravimetric adsorption apparatus. The following data were obtained on a sample activated at 350° C.

| | Kinetic Diameter, A | Pressure, Torr | Temp., °C. | Wt. % Adsorbed |
| --- | --- | --- | --- | --- |
| O$_2$ | 3.46 | 104 | −183 | 25.1 |
| O$_2$ | 3.46 | 746 | −183 | 36.6 |
| n-Hexane | 4.3 | 46 | 23.4 | 11.0 |
| H$_2$O | 2.65 | 4.6 | 23.0 | 30.1 |
| H$_2$O | 2.65 | 19.5 | 22.8 | 42.3 |

The pore size of the calcined product was determined to be greater than 4.3 A, as shown by adsorption of n-hexane which has a kinetic diameter of 4.3 A.

(c) The product of part (b), after the McBain adsorption studies, had an X-ray powder diffraction pattern characterized by the following data:

TABLE O

| 2θ | d | 100 × I/I$_o$ |
| --- | --- | --- |
| 9.45 | 9.36 | 100 |
| 12.95 | 6.84 | 25 |
| 14.0 | 6.33 | 5 |
| 16.1 | 5.50 | 27 |
| 16.9 | 5.25 | 3 |
| 17.7 | 5.01 | 9 |
| 19.05 | 4.66 | 3 |
| 20.75 | 4.28 | 55 |
| 21.25 | 4.18 | 1 |
| 22.0 | 4.04 | 3 |
| 22.55 | 3.94 | 2 |
| 23.15 | 3.84 | 4 |
| 24.8 | 3.59 | 21 |
| 25.05 | 3.555 | 11 |
| 27.8 | 3.209 | } 4 |
| 28.1 (sh) | 3.175 | |
| 29.6 | 3.018 | 3 |
| 30.8 | 2.903 | 26 |
| 31.6 | 2.831 | 2 |
| 32.3 | 2.772 | 2 |
| 33.3 | 2.691 | 2 |
| 34.7 | 2.585 | 4 |
| 35.85 | 2.505 | 4 |
| 38.6 | 2.332 | 1 |
| 39.85 | 2.262 | 2 |
| 42.7 | 2.118 | 2 |
| 43.5 | 2.080 | 2 |
| 47.05 | 1.932 | 1 |
| 47.9 | 1.899 | 2 |
| 48.8 | 1.866 | 4 |
| 50.5 | 1.807 | 3 |
| 51.9 | 1.762 | 1 |

TABLE O-continued

| 2θ | d | 100 × I/I₀ |
|---|---|---|
| 53.4 | 1.716 | 2 |
| 54.15 | 1.694 | 2 |
| 54.6 | 1.681 | 1 |

EXAMPLE 11 (SAPO-34)

(a) Isopropylamine (i-PrNH$_2$) was successfully employed to template the formation of SAPO-34 in a reaction mixture having the composition:

i-PrNH$_2$:0.6 SiO$_2$:Al$_2$O$_3$:P$_2$O$_5$:50H$_2$O and formed from aluminum isopropoxide, an aqueous silica sol, orthophosphoric acid and water. The reaction gel was crystallized at 200° C. for 51 hours at autogeneous pressure. X-ray analysis confirmed the formation of SAPO-34.

(b) A portion of the solid crystalline product of part (a) above was calcined in air for 3.5 hours at about 600° C. The major species of the calcined product had an X-ray powder diffraction pattern characteristic of SAPO-34.

(c) Adsorption capacities were measured on the calcined product of part (b) using a standard McBain-Bakr adsorption apparatus. The following data were obtained on a sample activated at 350° C.

| | Kinetic Diameter, A | Pressure, Torr | Temp., °C. | Wt. % Adsorbed |
|---|---|---|---|---|
| O$_2$ | 3.46 | 98 | −183 | 15.0 |
| O$_2$ | 3.46 | 746 | −183 | 21.7 |
| n-hexane | 4.3 | 97 | 24 | 3.7 |
| isobutane | 5.0 | 402 | 26 | 0.2 |
| H$_2$O | 2.65 | 4.6 | 22 | 18.7 |
| H$_2$O | 2.65 | 19.4 | 24 | 23.7 |

The pore side of the calcined product is greater than about 4.3 and less than about 5.0 A as shown by the adsorption of n-hexane, kinetic diameter of 4.3 A, and negligible adsorption of isobutane, kinetic diameter of 5.0 A.

EXAMPLE 12 (SAPO-34)

SAPO-34 was prepared by forming a mixture by combining a mixture of 68.1 grams of aluminum isopropoxide [Al(i-C$_3$H$_7$O)$_3$] in 120.1 grams of water with 38.4 grams of orthophosphoric acid (85 weight percent H$_3$PO$_4$). Cab-O-Sil EH5 (Trademark of Cabot Corporation, Boston, Mass., for a pyrogenic silica having 92.8 weight percent SiO$_2$ in water) was added (1.0 gram) to this mixture and the mixture was stirred until homogeneous mixture was observed. To one-half by weight of this mixture there was added 30.7 grams of the templating agent tetraethylammonium hydroxide (TEAOH) as a 40 percent by weight aqueous solution. The resulting mixture was stirred until a homogeneous mixture was observed. The composition of the final reaction mixture in terms of molar ratios, was:

0.5(TEA)$_2$O:0.1SiO$_2$:Al$_2$O$_3$:P$_2$O$_5$:45H$_2$O

The reaction mixture was sealed in a stainless steel pressure vessel lined with polytetrafluoroethylene. The mixture was then heated in an oven at a temperature of 150° C. at the autogeneous pressure for a period of about 89 hours. The silicoaluminophosphate product (i.e., the solid reaction product) was recovered by centrifugal filtration, washed with water, and dried in air at room temperature. This product was then calcined in air at 500° C. for a period of about 2 hours. The calcined product had X-ray pattern characterized by the general X-ray diffraction pattern set forth in Table XV.

TABLE XV

| 2θ | d | 100 × I/I₀ |
|---|---|---|
| 9.45–9.65 | 9.36–9.17 | s–vs |
| 16.0–16.2 | 5.54–5.47 | w–m |
| 17.85–18.15 | 4.97–4.89 | w–s |
| 20.55–20.9 | 4.32–4.25 | m–vs |
| 24.95–25.4 | 3.57–3.51 | w–s |
| 30.5–30.7 | 2.931–2.912 | w–s |

EXAMPLE 13 (SAPO-34)

SAPO-34 was crystallized from a reaction system containing both sodium and TEA ions prepared by combining 66.4 grams of aluminum isopropoxide with a solution of 28.8 grams of 85 wt-% orthophosphoric acid in 70.1 grams of H$_2$O. To this mixture was added a mixture of 15.0 grams of an aqueous silica sol (30 wt.-% SiO$_2$) and a solution of 3.0 grams of NaOH in 10.0 grams H$_2$O. Thereafter 46.0 grams of an aqueous solution of 40 wt.-% tetraethylammonium hydroxide was added and the mixture stirred until homogeneous. The composition of the final mixture was:

0.5(TEA)$_2$O:0.3Na$_2$O:1.3Al$_2$O$_3$:0.6SiO$_2$:P$_2$O$_5$:60H$_2$O

After crystallization in a sealed reactor at 200° C. for 187 hours, the SAPO-34 product (identified by X-ray analysis) had a chemical composition: 4.5 wt. % C; 37.7 wt. % Al$_2$O$_3$; 22.9 wt. % LOI; 29.5 wt. % P$_2$O$_5$; 4.9 wt % Na$_2$O; and 4.5 wt. % SiO$_2$.

EXAMPLE 14 (SAPO-34)

SAPO-34 was prepared by forming a mixture by adding 204.4 grams of aluminum isopropoxide [Al(i-C$_3$H$_7$O$_3$)] to a solution containing 115.3 grams of orthophosphoric acid (85 weight percent H$_3$PO$_4$) in 225 grams of water. The aluminum isopropoxide container was washed with 25 grams of water and that wash water was added to the mixture. Ludox LS and water (30.05 grams and 10.0 grams, respectively) were added to this mixture and the mixture was stirred until a homogenous mixture was observed. To this mixture there was added 368.3 grams of the templating agent tetraethylammonium hydroxide (TEAOH) as a 40 percent by weight aqueous solution, with 14.8 grams of additional water. The resulting mixture was stirred until a homogeneous mixture was observed. The composition of the final reaction mixture in terms of molar ratios was:

2(TEA)$_2$O:0.3SiO$_2$:Al$_2$O$_3$:P$_2$O$_5$:50H$_2$O

The reaction mixture was sealed in a stainless steel pressure vessel lined with polytetrafluoroethylene. The mixture was then heated in an oven at 200° C. at the autogenous pressure for about 120 hours. The silicoaluminophosphate product (i.e., the solid reaction product) was recovered by centrifugal filtration, washed with water, and dried in air at a temperature of 110° C. A portion of this product was then calcined in air at 550° C. for a period of about 2 hours. The calcined product had an X-ray powder diffraction pattern characterized by the general X-ray powder diffraction pattern set forth in Table XVI.

TABLE XVI

| 2θ | d | 100 × I/I$_o$ |
|---|---|---|
| 9.45–9.65 | 9.36–9.17 | s–vs |
| 16.09–16.2 | 5.54–5.47 | w–m |
| 17.85–18.15 | 4.97–4.89 | w–s |
| 20.55–20.9 | 4.32–4.25 | m–vs |
| 24.95–25.4 | 3.57–3.51 | w–s |
| 30.5–30.7 | 2.931–2.912 | w–s |

EXAMPLE 15 (SAPO-34)

Example 14 was repeated and the SAPO prepared was identified as SAPO-34.

SAPO-35

SAPO-35, as referred to herein, comprises a silicoaluminophosphate material having a three-dimensional microporous crystal framework structure of [PO$_2$], [AlO$_2$] and [SiO$_2$] tetrahedral units, and whose unit empirical formula of an anhydrous basis is:

$$mR:(Si_xAl_yP_z)O_2$$

wherein "R" represents at least one organic templating agent present in the intracrystalline pore system; "m" represents the moles of "R" present per mole of (Si$_x$Al$_y$P$_z$)O$_2$ and has a value of from zero to 0.3, "x", "y" and "z" represent respectively, the mole fractions of silicon, aluminum and phosphorus, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern (as-synthesized and calcined) which contains at least the d-spacings set forth below in Table XVII. When SAPO-35 is in the as-synthesized form "m" preferably has a value of from 0.02 to 0.3.

TABLE XVII

| 2θ | | d | Relative Intensity |
|---|---|---|---|
| 10.9–11.05 | | 8.12–8.01 | m |
| 17.2–17.4 | | 5.16–5.10 | |
| | | | s |
| 17.4–17.7 | (sh) | 5.10–5.01 | |
| 21.0–21.25 | | 4.23–4.18 | m |
| 21.8–22.0 | | 4.08–4.04 | vs |
| 32.0–32.15 | | 2.797–2.784 | m |

All of the as-synthesized SAPO-35 compositions for which X-ray powder diffraction data have presently been obtained have patterns which are within the generalized pattern of Table XVIII, below.

TABLE XVIII

| 2θ | | d | 100 × I/I$_o$ |
|---|---|---|---|
| 8.5–8.7 | | 10.4–10.1 | 13–18 |
| 10.9–11.05 | | 8.12–8.01 | 38–48 |
| 11.6–11.9 | | 7.63–7.44 | 1–3 |
| 13.2–13.4 | | 6.71–6.61 | 23–24 |
| 15.75–16.0 | | 5.62–5.54 | 7–12 |
| 17.2–17.4 | | 5.16–5.10 | |
| | | | 66–83 |
| 17.4–17.7 | (sh) | 5.10–5.01 | |
| 17.6–17.9 | | 5.04–4.96 | 9–18 |
| 21.0–21.25 | | 4.23–4.18 | 47–56 |
| 21.8–22.0 | | 4.08–4.04 | 100 |

TABLE XVIII-continued

| 2θ | d | 100 × I/I$_o$ |
|---|---|---|
| 23.0–23.3 | 3.87–3.82 | 14–18 |
| 23.55–23.75 | 3.78–3.75 | 6 |
| 24.9–25.2 | 3.58–3.53 | 3–6 |
| 25.85–26.0 | 3.446–3.427 | 0–2 |
| 26.7–26.9 | 3.339–3.314 | 16–19 |
| 28.4–28.55 | 3.143–3.126 | 22–26 |
| 28.65–28.85 | 3.116–3.095 | 13–20 |
| 29.0–29.1 | 3.079–3.069 | 4–6 |
| 32.0–32.15 | 2.797–2.784 | 33–47 |
| 34.55–34.7 | 2.596–2.585 | 6–9 |
| 35.6–35.8 | 2.522–2.508 | 3–4 |
| 37.7–37.8 | 2.386–2.380 | 2–3 |
| 39.2–39.3 | 2.298–2.292 | 2 |
| 40.7–40.8 | 2.217–2.212 | 0–2 |
| 41.95–42.1 | 2.154–2.146 | 3–5 |
| 42.4–42.55 | 2.132–2.125 | 2–4 |
| 42.95–43.2 | 2.106–2.094 | 2–4 |
| 44.4–44.5 | 2.040–2.036 | 1–2 |
| 48.4–48.55 | 1.881–1.875 | 7–8 |
| 49.3–49.45 | 1.848–1.843 | 6–8 |
| 51.4–51.5 | 1.778–1.774 | 5–8 |
| 55.2–55.25 | 1.664–1.663 | 4–7 |

EXAMPLE 16 (SAPO-35)

(a) SAPO-35 was prepared by combining 132 grams of water with 132.8 grams of aluminum isopropoxide (Al(i-OC$_3$H$_7$)$_3$) and then adding 30.1 grams of an aqueous sol containing 30 wt.% SiO$_2$ and 45 grams of water. To this mixture was added 57.7 grams of 85 wt.% orthophosphoric acid (H$_3$PO$_4$) and the mixture stirred until homogeneous. To this mixture was added a solution of 27.8 grams of quinuclidine, C$_7$H$_{13}$N, (QN) in 50 grams of water, and the mixture stirred until homogeneous. The composition of the final reaction mixture in molar oxide ratios was:

1.0QN:0.6SiO$_2$:1.3Al$_2$O$_3$:P$_2$O$_5$:60H$_2$O

Part of the reaction mixture was placed in a stainless steel pressure vessel lined with polytetrafluorolethylene and heated in an oven at 150° C. at autogenous pressure for 48 hours. The solid reaction product was recovered by centrifugation, washed in water, and dried in air at 100° C. The above product was impure but the major product had an X-ray powder diffraction pattern consistent with that of SAPO-35.

(b) A portion of the solid crystalline product was calcined in air at about 600° C. for 2 hours. The whiter portion of the calcined product had an X-ray powder pattern characterized by the following data:

TABLE P

| 2θ | d | 100 × I/I$_o$ |
|---|---|---|
| 6.8 | 13.0 | 2 |
| 8.2 | 10.78 | 2 |
| 8.7 | 10.16 | 14 |
| 11.0 | 8.04 | 100 |
| 11.4 | 7.76 | 17 |
| 13.55 | 6.53 | 89 |
| 16.1 | 5.50 | 4 |
| 17.4 | 5.10 | 24 |
| 18.7 | 4.75 | 3 |
| 21.0 | 4.23 | 29 |
| 22.2 | 4.00 | 63 |
| 23.0 | 3.87 | 4 |
| 23.6 | 3.77 | 15 |
| 25.05 | 3.555 | 13 |
| 26.0 | 3.427 | 9 |
| 27.3 | 3.267 | 20 |
| 28.6 | 3.121 | 42 |
| 29.5 | 3.028 | 10 |

TABLE P-continued

| 2θ | d | 100 × I/I₀ |
|---|---|---|
| 30.6 | 2.921 | 2 |
| 31.75 | 2.818 | 6 |
| 32.4 sh | 2.763 | 32 |
| 32.6 | 2.747 | |
| 34.6 | 2.592 | 7 |
| 35.4 | 2.536 | 4 |
| 36.3 | 2.475 | 2 |
| 47.9 | 1.899 | 2 |
| 51.7 | 1.768 | 3 |

(c) Adsorption capacities were measured on the calcined product using a standard McBain-Bakr gravimetric adsorption apparatus. The following data were obtained on a sample activated at 350° C.:

| | Kinetic Diameter, A | Pressure, Torr | Temp., °C. | Wt. % Adsorbed |
|---|---|---|---|---|
| O₂ | 3.46 | 98 | −183 | 15.3 |
| O₂ | 3.46 | 746 | −183 | 30.3 |
| isobutane | 5.0 | 101 | 25 | 0.7 |
| n-hexane | 4.3 | 48 | 24 | 10.2 |
| H₂O | 2.65 | 4.6 | 22 | 22.2 |
| H₂O | 2.65 | 19 | 24 | 47.7 |

The pore size of the calcined product was determined to be between about 4.34 A and about 5.0 A as shown by adsorption of n-hexane, kinetic diameter of 4.3 A, and negligible adsorption of isobutane, kinetic diameter of 5.0 A.

EXAMPLE 17 (SAPO-35)

SAPO-35 was prepared by forming a mixture by combining 46.1 grams of orthophosphoric acid (85 weight percent H₃PO₄) with a mixture of 81.7 grams of aluminum isopropoxide [Al(i-C₃H₇O)₃] in 60.9 grams of water. Ludox LS was added (12.0 grams) to this mixture and the mixture was stirred until a homogeneous mixture was observed. To a portion of this mixture (42.5 percent by weight) there was added 37.8 grams of the templating agent quinuclidine (QN) and 75.1 grams of water. The resulting mixture was stirred until a homogeneous mixture was observed. The composition of the final reaction mixture expressed in terms of molar ratios was:

$$4(QN):0.3SiO_2:Al_2O_3:P_2O_5:75H_2O$$

The reaction mixture was sealed in a stainless steel pressure vessel lined with polytetrafluoroethylene. The mixture was then heated in an oven at a temperature of 200° C. at the autogenous pressure for a period of about 168 hours. The silicoaluminophosphate product (i.e., the solid reaction product) was recovered by centrifugal filtration, washed with water, and dried in air at a temperature of 100° C. The molecular sieve product was then calcined in air at 550° C. for a period of about 3 hours. The calcined product had an X-ray powder diffraction pattern characterized by the following general X-ray powder diffraction pattern.

TABLE XIX

| 2θ | d | 100 × I/I₀ |
|---|---|---|
| 10.9–11.05 | 8.12–8.01 | m |
| 17.2–17.4 | 5.16–5.10 | s |
| 17.4–17.7 sh | 5.10–5.01 | — |
| 21.0–21.25 | 4.23–4.18 | m |

TABLE XIX-continued

| 2θ | d | 100 × I/I₀ |
|---|---|---|
| 21.8–22.0 | 4.08–4.04 | vs |
| 32.0–32.15 | 2.797–2.784 | m |

SAPO-37

SAPO-37, as referred to herein, comprises a silicoaluminophosphate having a microporous crystalline framework structure and whose unit empirical formula on an anhydrous basis is:

$$mR:(Si_xAl_yP_z)O_2$$

wherein R represents at least one organic templating agent present in the intracrystalline pore system, "m" has a value of from zero to 0.3, preferably from 0.02 to 0.3, "x", "y" and "z" represent, respectively, the mole fraction of silicon, aluminum and phosphorus, the value of x, y and z being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern (as synthesized and calcined) which contains at least the d-spacings set forth below in Table XX:

TABLE XX

| 2θ | d | Relative Intensity |
|---|---|---|
| 6.1–6.3 | 14.49–14.03 | vs |
| 15.5–15.7 | 5.72–5.64 | w–m |
| 18.5–18.8 | 4.80–4.72 | w–m |
| 23.5–23.7 | 3.79–3.75 | w–m |
| 26.9–27.1 | 3.31–3.29 | w–m |

All of the as-synthesized SAPO-37 compositions for which X-ray powder diffraction data have presently been obtained have patterns which are within the generalized pattern of Table XXI, below.

TABLE XXI

| 2θ | d | 100 × I/I₀ |
|---|---|---|
| 6.1–6.3 | 14.49–14.03 | 100 |
| 10.1–10.3 | 8.76–8.59 | 22–30 |
| 11.8–12.0 | 7.50–7.37 | 4–10 |
| 15.5–15.7 | 5.72–5.64 | 30–60 |
| 18.5–18.8 | 4.80–4.72 | 20–50 |
| 20.2–20.4 | 4.40–4.35 | 12–26 |
| 21.0–21.2 | 4.23–4.19 | 4–10 |
| 22.7–22.9 | 3.92–3.88 | 8–21 |
| 23.5–23.7 | 3.79–3.75 | 24–59 |
| 24.6–24.9 | 3.62–3.58 | 1–3 |
| 25.6–25.8 | 3.48–3.45 | 5–11 |
| 26.9–27.1 | 3.31–3.29 | 14–42 |
| 27.6–27.9 | 3.232–3.198 | 2–4 |
| 29.4–29.7 | 3.038–3.008 | 2–11 |
| 30.6–30.8 | 2.921–2.903 | 5–18 |
| 31.2–31.5 | 2.867–2.840 | 12–32 |
| 32.2–32.5 | 2.780–2.755 | 3–11 |
| 33.0–33.2 | 2.714–2.698 | 1–3 |
| 33.9–34.2 | 2.644–2.622 | 4–14 |
| 34.3–34.5 | 2.614–2.600 | 2–6 |
| 37.7–38.0 | 2.386–2.368 | 3–9 |
| 40.4–40.7 | 2.232–2.217 | 1–5 |
| 41.2–41.5 | 2.191–2.176 | 1–7 |
| 43.1–43.3 | 2.099–2.089 | 1–7 |
| 43.9–44.1 | 2.062–2.053 | 2–8 |

EXAMPLE 18 (SAPO-37)

(a) SAPO-37 was formed by combining 27.7 grams of 85 wt.% orthophosphoric acid ($H_3PO_4$) and 30.5 grams of water, to which was added 16.6 grams of hydrated aluminum oxide (a pseudo-boehmite phase, 74.2 wt.% $Al_2O_3$, 25.8 wt.% $H_2O$), and stirred until homogeneous. To this mixture was added a dispersion of 3.1 grams of a fumed silica (92.8 wt.% $SiO_2$, 7.2 wt.% $H_2O$) and 1.1 gram of tetramethylammonium hydroxide pentahydrate (TMAOH $5.H_2O$) in 115.98 grams of an aqueous solution of 40 wt.% tetra-n-propylammonium hydroxide (TPAOH) and the mixture stirred until homogeneous. The composition of the final reaction mixture in molar oxide ratios was:

$Al_2O_3:P_2O_5:0.4SiO_2:(TPA)_2O:0.025(TMA)_2O:50-H_2O$

A portion of the reaction mixture was placed in a stainless steel pressure vessel lined with polytetrafluoroethylene and heated in an oven at 200° C. at autogenous pressure for 24 hours. The solid reaction product was recovered by centrifuging and washing with water, and dried in air at 100° C. The above product had an X-ray powder diffraction pattern characterized by the following data:

TABLE Q

| $2\theta$ | d | $100 \times I/I_o$ |
|---|---|---|
| 6.2 | 14.25 | 100 |
| 10.1 | 8.74 | 22 |
| 11.9 | 7.44 | 5 |
| 15.6 | 5.68 | 42 |
| 18.5 | 4.80 | 34 |
| 20.2 | 4.40 | 16 |
| 21.2 | 4.19 | 4 |
| 22.7 | 3.92 | 11 |
| 23.5 | 3.79 | 39 |
| 24.8 | 3.59 | 1 |
| 25.7 | 3.47 | 6 |
| 26.9 | 3.314 | 27 |
| 27.6 | 3.232 | 2 |
| 29.4 | 3.038 | 7 |
| 30.6 | 2.921 | 9 |
| 31.2 | 2.867 | 18 |
| 32.2 | 2.780 | 5 |
| 33.0 | 2.714 | 2 |
| 33.9 | 2.644 | 7 |
| 34.4 | 2.607 | 3 |
| 37.8 | 2.380 | 6 |
| 40.4 | 2.233 | 2 |
| 41.2 | 2.191 | 2 |
| 43.1 | 2.099 | 1 |
| 43.9 | 2.062 | 3 |

The chemical composition of the SAPO-37 product was determined to be: 31.8 wt.% $Al_2O_3$; 31.4 wt.% $P_2O_5$; 9.2 wt.% $SiO_2$; 14.2 wt.% C; 1.8 wt.% N; and 26.1 wt.% LOI, which corresponds to a product composition in molar oxide ratios of:

$1.0Al_2O_3:0.71P_2O_5:0.49SiO_2:0.13(TPA)_2O:0.07(TMA)_2O:0.89H_2O$, and, thus, had the unit empirical formula (anhydrous basis):

$0.10(TPA+TMA):(Si_{0.125}Al_{0.51}P_{0.365})O_2$ (b) A portion of the solid crystalline product of (a) was calcined in air at about 600° C. for 1 hour. The calcined product had an X-ray powder diffraction pattern characterized by the data shown in the following table:

TABLE R

| $2\theta$ | d | $100 \times I/I_o$ |
|---|---|---|
| 6.2 | 14.25 | 100 |
| 10.3 | 8.59 | 19 |
| 12.1 | 7.37 | 11 |
| 15.9 | 5.57 | 20 |
| 18.6 | 4.77 | 7 |
| 20.4 | 4.35 | 9 |
| 21.5 | 4.13 | 1 |
| 22.9 | 3.88 | 3 |
| 23.8 | 3.74 | 13 |
| 25.0 | 3.56 | 1 |
| 25.8 | 3.45 | 1 |
| 27.0 | 3.30 | 7 |
| 27.7 | 3.22 | 1 |
| 29.5 | 3.03 | 2 |
| 30.7 | 2.92 | 4 |
| 31.4 | 2.85 | 7 |
| 32.4 | 2.76 | 2 |
| 33.0 | 2.71 | 1 |
| 34.0 | 2.63 | 3 |
| 34.6 | 2.59 | 1 |
| 37.9 | 2.37 | 2 |
| 40.5 | 2.23 | 1 |
| 41.2 | 2.19 | 1 |
| 43.1 | 2.10 | 1 |
| 44.0 | 2.06 | 1 |

(c) Adsorption capacities were measured on this calcined product using a standard McBain-Bakr gravimetric adsorption apparatus. The following data were obtained on a sample activated at 350° C. in vacuum.

| | Kinetic Diameter, A | Pressure, Torr | Temp., °C. | Wt. % Adsorbed |
|---|---|---|---|---|
| $O_2$ | 3.46 | 100 | −183 | 35.0 |
| $O_2$ | 3.46 | 750 | −183 | 42.9 |
| Cyclohexane | 6.0 | 60 | 24 | 23.2 |
| Neopentane | 6.2 | 743 | 24 | 14.8 |
| $H_2O$ | 2.65 | 4.6 | 24 | 35.3 |

The pore size of the calcined product is greater than 6.2 A, as shown by adsorption of neopentane which has a kinetic diameter of about greater than 6.2 A.

(d) EDAX (energy dispersive analysis by X-ray) microprobe analysis, performed in conjunction with SEM (scanning electron microscope) study, on clean crystals having a crystal morphology characteristic of SAPO-37 gives the following analysis based on relative peak heights:

| Si | 1 |
|---|---|
| Al | 3 |
| P | 2 |

(e) Mixtures of tetramethylammonium hydroxide with tri-n-propylamine and with tetra-n-butylammonium hydroxide were also found to provide for the formation of SAPO-37.

SAPO-40

SAPO-40, as referred to herein, comprises a silicoaluminophosphate material having a three-dimensional microporous crystal framework structure of [$PO_2$], [$AlO_2$] and [$SiO_2$] tetrahedral units, and whose unit empirical formula on an anhydrous basis is:

$mR:(Si_xAl_yP_x)O_2$ wherein "R" represents at least one organic templating agent present in the intracrystalline pore system; "m" represents the moles of "R" present per mole of $(Si_xAl_yP_z)O_2$ and has a value of from zero to 0.3, "x", "y" and "z" represent respectively, the mole fractions of silicon, aluminum and phosphorus present said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern (as-synthesized and calcined) which contains at least the d-spacings set forth below in Table XXII. When SAPO-40 is in the as-synthesized form "m" preferably has a value of from 0.02 to 0.3.

TABLE XXII

| 2θ | d | Relative Intensity |
|---|---|---|
| 7.5–7.7 | 11.79–11.48 | vw–m |
| 8.0–8.1 | 11.05–10.94 | s–vs |
| 12.4–12.5 | 7.14–7.08 | w–vs |
| 13.6–13.8 | 6.51–6.42 | m–s |
| 14.0–14.1 | 6.33–6.28 | w–m |
| 27.8–28.0 | 3.209–3.18 | w–m |

All of the as-synthesized SAPO-40 compositions for which X-ray powder diffraction data have presently been obtained have patterns which are within the generalized pattern of Table XXIII, below.

TABLE XXIII

| 2θ | d | 100 × I/I$_o$ |
|---|---|---|
| 7.5–7.71 | 11.79–11.48 | 6–51 |
| 8.0–8.1 | 11.05–10.94 | 85–100 |
| 12.4–12.5 | 7.14–7.08 | 15–100 |
| 13.6–13.8 | 6.51–6.42 | 43–62 |
| 14.0–14.1 | 6.33–6.28 | 12–36 |
| 16.1–16.3 | 5.50–5.44 | 1–2 |
| 17.3–17.7 | 5.13–5.01 | 6–17 |
| 18.5–18.6 | 4.80–4.77 | 14–30 |
| 19.7–20.0 | 4.51–4.44 | 6–22 |
| 20.3–20.5 | 4.37–4.33 | 12–19 |
| 21.3–21.5 | 4.17–4.13 | 10–19 |
| 21.6–21.9 | 4.11–4.06 | 6–22 |
| 22.9–23.2 | 3.88–3.83 | 4–9 |
| 23.7–23.8 | 3.75–3.74 | 19–30 |
| 24.0–24.3 | 3.71–3.66 | 0–5 |
| 24.6–24.7 | 3.62–3.60 | 1–17 |
| 27.3–27.5 | 3.267–3.24 | 22–29 |
| 27.8–28.0 | 3.209–3.18 | 15–33 |
| 28.0–28.2 | 3.187–3.164 | 0–4 |
| 28.5–28.7 | 3.132–3.110 | 0–2 |
| 29.2–29.3 | 3.058–3.048 | 0–9 |
| 30.3–30.4 | 2.950–2.940 | 0–3 |
| 30.6–30.7 | 2.921–2.912 | 0–2 |
| 31.0–31.2 | 2.885–2.867 | 0–3 |
| 31.7–31.9 | 2.823–2.805 | 4–5 |
| 32.3–32.5 | 2.772–2.755 | 3–5 |
| 33.2–33.4 | 2.698–2.683 | 1–2 |
| 33.7–33.8 | 2.660–2.652 | 2–3 |
| 35.0–35.2 | 2.564–2.550 | 2–3 |
| 35.8–35.9 | 2.508–2.501 | 2–3 |

EXAMPLE 19 (SAPO-40)

(a) SAPO-40 was produced by crystallizing at 200° C. for 96 hours under autogenous pressure a reaction mixture containing both sodium hydroxide and TPAOH in addition to phosphoric acid, a hydrated aluminum oxide, water and a fumed silica in proportions such that the reaction mixture had the composition:

$Al_2O_3:P_2O_5:0.4SiO_2:(TPA)_2O:0.01Na_2O:50H_2O$

A portion of the recovered solids gave a x-ray powder diffraction pattern characterized by the following data (peaks resulting solely from a minor SAPO-5 impurity have been omitted):

TABLE S

| 2θ | d | 100 × I/I$_o$ |
|---|---|---|
| 7.60* | 11.63 | 18 |
| 8.03 | 11.01 | 100 |
| 12.43 | 7.12 | 18 |
| 13.68 | 6.47 | 43 |
| 14.02 | 6.32 | 12 |
| 16.12 | 5.50 | 1 |
| 17.36 | 5.11 | 7 |
| 18.50 | 4.80 | 14 |
| 19.72 | 4.50 | 6 |
| 20.39 | 4.36 | 13 |
| 21.40 | 4.15 | 10 |
| 21.68 | 4.10 | 6 |
| 22.93 | 3.88 | 4 |
| 23.74 | 3.75 | 19 |
| 24.21 | 3.68 | 5 |
| 24.62 | 3.61 | 1 |
| 27.32 | 3.264 | 22 |
| 27.84 | 3.204 | 15 |
| 28.10 | 3.176 | 4 |
| 28.59 | 3.123 | 1 |
| 30.34 | 2.946 | 3 |
| 30.61 | 2.920 | 2 |
| 31.07 | 2.878 | 3 |
| 31.76 | 2.817 | 4 |
| 32.33 | 2.769 | 3 |
| 33.28 | 2.692 | 2 |
| 33.77 | 2.654 | 2 |
| 35.07 | 2.559 | 2 |
| 35.82 | 2.507 | 3 |

*Contains peak from impurity

Chemical analysis indicated the product contained: 8.9 wt.% C; 1.0 wt.% N; 34.4 wt.% $Al_2O_3$; 40.4 wt.% $P_2O_5$; 6.9 wt.% $SiO_2$; 0.7 wt.% $Na_2O$; and 17.5 wt.% LOI; which gave a product composition in molar oxide ratios of:

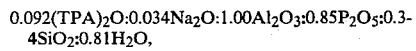

$0.092(TPA)_2O:0.034Na_2O:1.00Al_2O_3:0.85P_2O_5:0.34SiO_2:0.81H_2O$, and a unit empirical formula (anhydrous basis)

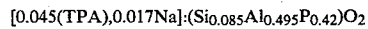

$[0.045(TPA),0.017Na]:(Si_{0.085}Al_{0.495}P_{0.42})O_2$ (b) A portion of the product of part (a) was calcined in air at 700° C. for 1 hour. The X-ray pattern of the calcined material was characterized by the following data after subtraction of peaks contributed by identified impurities:

TABLE T

| 2θ | d | 100 × I/I$_o$ |
|---|---|---|
| 7.60 | 11.63 | 78 |
| 7.95 | 11.19 | 100 |
| 12.55 | 7.08 | 14 |
| 13.60 | 6.51 | 13 |
| 14.20 | 6.24 | 13 |
| 16.00 | 5.54 | 3 |
| 17.40 | 5.10 | 9 |
| 18.60 | 4.77 | 15 |
| 20.40 | 4.35 | 7 |
| 21.65 | 4.11 | 4 |
| 22.75 | 3.92 | 3 |
| 23.70 | 3.75 | 3 |
| 27.15 | 3.290 | 15 |
| 28.00 | 3.186 | 12 |
| 30.65 | 2.921 | 3 |

TABLE T-continued

| 2θ | d | 100 × I/I₀ |
|---|---|---|
| 31.70 | 2.822 | 3 |
| 32.40 | 2.763 | 2 |

(c) Adsorption capacities were measured on this calcined product using a standard McBain-Bakr gravimetric adsorption apparatus. The following data were obtained on a sample activated at 350° C. in vacuum.

| | Kinetic Diameter, A | Pressure, Torr | Temp., °C. | Wt % Adsorbed |
|---|---|---|---|---|
| $O_2$ | 3.46 | 100 | −183 | 21.8 |
| $O_2$ | 3.46 | 750 | −183 | 24.4 |
| Cyclohexane | 6.0 | 60 | 24 | 8.0 |
| Neopentane | 6.2 | 743 | 24 | 5.1 |
| $H_2O$ | 2.65 | 4.6 | 24 | 22.7 |
| $H_2O$ | 2.65 | 20 | 24 | 31.5 |
| Isobutane | 5.0 | 697 | 24 | 7.0 |
| $SF_6$ | 5.5 | 400 | 24 | 11.6 |

The pore size of the calcined product was determined to be greater than 6.2 A, as shown by adsorption of neopentane, kinetic diameter 6.2 A. It should be noted, however, that the sample contained substantial amounts of SAPO-5, which adsorbs molecules as large as neopentane.

(d) EDAX (energy dispersive analysis by X-ray) microprobe analysis, performed in conjunction with SEM (scanning electron microscope) study, on clean crystals having a crystal morphology characteristic of SAPO-40 gives the following analysis based on relative peak heights:

| | Laths |
|---|---|
| Si | 0.14 |
| Al | 1.0 |
| P | 0.95 |

EXAMPLE 20 (SAPO-40)

A reaction mixture was prepared by combining, in a manner to obtain a homogeneous composition, 6.90 grams of a hydrated aluminum oxide (74.2 wt.-% $Al_2O_3$, 25.8 wt.-% $H_2O$) with 11.53 grams of 85% orthophosphoric acid, and a solution of 0.38 gram ammonium acetate ($NH_4Ac$) in 11.16 grams $H_2O$, and finally with a mixture of 1.30 grams of a fumed silica (92.8 wt.-% $SiO_2$) in 50.9 grams of 40% aqueous tetra-n-propylammonium hydroxide solution (TPAOH). The composition of the reaction mixture was:

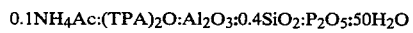

0.1$NH_4Ac$:(TPA)$_2$O:Al$_2$O$_3$:0.4SiO$_2$:P$_2$O$_5$:50H$_2$O

After digestion and crystallization in a sealed reactor at 200° C. for 24 hours, a SAPO-40-containing product was recovered, as determined by the X-ray powder diffraction pattern.

SAPO-42

SAPO-42, as referred to herein, comprises a silicoaluminophosphate having a microporous crystalline framework structure of [$PO_2$], [$AlO_2$] and [$SiO_2$] tetrahedral units and whose unit empirical formula on an anhydrous basis is:

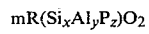

$mR(Si_xAl_yP_z)O_2$ wherein R represents at least one organic templating agent present in the intracrystalline pore system, "m" has a value of from zero to 0.3, preferably from 0.02 to 0.03, "x", "y" and "z" represent, respectively, the mole fraction of silicon, aluminum and phosphorus, the value of x, y and z being within the compositional area bounded by points A, B, C, D and E on the ternary diagram which is FIG. 1, or preferably within the area bounded by points a, b, c, d and e on the ternary diagram which is FIG. 2., said silicoaluminophosphate having a characteristic X-ray powder diffraction pattern (as-synthesized and calcined) which contains at least the d-spacings set forth below in Table XXIV:

TABLE XXIV

| 2θ | d | Relative Intensity |
|---|---|---|
| 7.15–7.4 | 12.36–11.95 | m–vs |
| 12.5–12.7 | 7.08–6.97 | m–s |
| 21.75–21.9 | 4.086–4.058 | m–s |
| 24.1–24.25 | 3.69–3.67 | vs |
| 27.25–27.4 | 3.273–3.255 | s |
| 30.05–30.25 | 2.974–2.955 | m–s |

All of the as-synthesized SAPO-42 compositions for which X-ray powder diffraction data have presently been obtained have patterns which are within the generalized pattern of Table XXV, below:

TABLE XXV

| 2θ | d | 100 × I/I₀ |
|---|---|---|
| 6.75–6.85 | 13.09–12.90 | sh–13 |
| 7.15–7.4 | 12.36–11.95 | 51–100 |
| 10.2–10.4 | 8.67–8.51 | 42–65 |
| 12.5–12.7 | 7.08–6.97 | 48–74 |
| 13.65–13.9 | 6.49–6.37 | 5–10 |
| 16.2–16.35 | 5.47–5.42 | 31–37 |
| 17.7–17.9 | 5.01–4.96 | 11–17 |
| 20.5 | 4.33 | 0–3 |
| 21.5–21.6 | 4.13–4.11 | sh–12 |
| 21.75–21.9 | 4.086–4.058 | 53–72 |
| 22.95–23.1 | 3.875–3.850 | 13–20 |
| 24.1–24.25 | 3.693–3.670 | 91–100 |
| 26.2–26.4 | 3.401–3.376 | 19–29 |
| 27.25–27.4 | 3.273–3.255 | 73–87 |
| 27.7 | 3.220 | 0–6 |
| 30.05–30.25 | 2.974–2.955 | 64–80 |
| 31.0–31.1 | 2.885–2.876 | 10–16 |
| 32.65–32.9 | 2.743–2.722 | 16–21 |
| 33.55–33.7 | 2.671–2.660 | 6–10 |
| 34.35–34.45 | 2.612–2.603 | 32–39 |
| 35.9–36.05 | 2.501–2.491 | 13–19 |
| 36.75–36.9 | 2.445–4.436 | 3–8 |
| 38.14–38.25 | 2.359–2.347 | 5–8 |
| 40.35–40.5 | 2.235–2.227 | 7–11 |
| 41.7–41.95 | 2.166–2.154 | 8–13 |
| 42.35–42.55 | 2.134–2.125 | 5–13 |
| 43.15–43.4 | 2.096–2.085 | 0–3 |
| 43.8–43.85 | 2.067–2.065 | 0–2 |
| 44.45–44.55 | 2.038–2.034 | 6–9 |
| 47.55–47.7 | 1.912–1.907 | 8–10 |
| 48.2–48.3 | 1.888–1.884 | 3–6 |
| 48.85–49.0 | 1.864–1.859 | 0–7 |
| 49.05–49.5 | 1.857–1.841 | 5–7 |
| 50.01–50.05 | 1.824–1.822 | 0–5 |
| 52.3–52.4 | 1.749–1.746 | 0–3 |
| 52.9–53.0 | 1.731–1.728 | 11–16 |
| 53.6 | 1.710 | 0–2 |
| 54.6–54.7 | 1.681–1.678 | 8–16 |
| 55.1–55.2 | 1.667–1.664 | 0–3 |

EXAMPLE 21 (SAPO-42)

(a) SAPO-42, which appears to be structurally similar to the aluminosilicate zeolite A, is found to be produced by the extended aging at lower temperatures of a gel composition which otherwise yields SAPO-20, a silicoaluminophosphate which has structural similarity to the aluminosilicate sodalite. A composition was prepared having the following molar oxide ratios of:

1.2Na$_2$O:1.1(TMA)$_2$O:4.0SiO$_2$:1.66Al$_2$O$_3$:0.66-P$_2$O$_5$:95H$_2$O

Part of the reaction mixture was placed in a sealed inert plastic container and heated in an oven at 100° C. at autogenous pressure for 480 hours. The solid reaction product was recovered by centrifugation, washed with water, and dried in air at 100° C. The above product had an X-ray powder diffraction pattern characterized by the following data:

TABLE U

| 2θ | d | 100 × I/I$_o$ |
|---|---|---|
| 7.4 | 11.9 | 71 |
| 10.4 | 8.51 | 55 |
| 12.7 | 6.97 | 61 |
| 13.9 | 6.37 | 7 |
| 16.35 | 5.42 | 31 |
| 17.9 | 4.96 | 13 |
| 21.6 (sh) | 4.13 | 68 |
| 21.9 | 4.06 | |
| 23.1 | 3.85 | 17 |
| 24.25 | 3.67 | 100 |
| 26.4 | 3.376 | 29 |
| 27.4 | 3.255 | 83 |
| 30.25 | 2.955 | 75 |
| 31.1 | 2.876 | 15 |
| 32.9 | 2.722 | 19 |
| 33.7 | 2.660 | 9 |
| 34.45 | 2.603 | 37 |
| 36.05 | 2.491 | 19 |
| 36.9 | 2.436 | 5 |
| 38.35 | 2.347 | 5 |
| 40.5 | 2.227 | 7 |
| 41.85 | 2.158 | 11 |
| 42.55 | 2.125 | 6 |
| 43.15 | 2.096 | 3 |
| 43.85 | 2.065 | 1 |
| 44.5 | 2.036 | 9 |
| 47.7 | 1.907 | 8 |
| 48.3 | 1.884 | 4 |
| 49.0 | 1.859 | 1 |
| 49.5 | 1.841 | 6 |
| 50.05 | 1.822 | 4 |
| 52.4 | 2.746 | 3 |
| 53.0 | 1.728 | 16 |
| 53.6 | 1.710 | 2 |
| 54.65 | 1.679 | 16 |
| 55.2 | 1.664 | 2 |

By chemical analysis, the composition of the crystalline product was found to be 11.3 wt.% Na$_2$O, 38.3 wt.% SiO$_2$; 25.6 wt.% Al$_2$O$_3$; 1.6 wt.-% C; 0.43 wt-% N; 4.4 wt.% P$_2$O$_5$; and 19.9 wt.% LOI; which gave a product composition in molar oxide ratios of:

0.07(TMA)$_2$O:2.5SiO$_2$:0.7Na$_2$O:Al$_2$O$_3$:0.1P$_2$O$_5$:3.7-H$_2$O which corresponds in turn to the formula (anhydrous basis):

0.03(TMA):(Si$_{0.53}$Al$_{0.42}$P$_{0.04}$)O$_2$ (b) A portion of the SAPO-42 of part (a) was calcined in air at 550° C. for 2 hours. Adsorption capacities were measured on this calcined sample using a standard McBain-Bakr gravimetric adsorption apparatus. The following data were obtained on a sample activated at 350° C.

| | Kinetic Diameter, A | Pressure, Torr | Temp., °C. | Wt. % Adsorbed |
|---|---|---|---|---|
| O$_2$ | 3.46 | 98.5 | −183 | 12.6 |
| O$_2$ | 3.46 | 740. | −183 | 17.0 |
| n-Hexane | 4.3 | 53.5 | 24 | 7.4 |
| Isobutane | 5.0 | 751. | 24 | 1.0 |
| H$_2$O | 2.65 | 4.6 | 23 | 15.5 |
| H$_2$O | 2.65 | 19.4 | 24 | 21.0 |

The pore size of the calcined product was determined to be greater than about 4.3 A, as shown by the adsorption of n-hexane and less than about 5.0 A, as shown by the negligible adsorption of isobutane.

SAPO-44

SAPO-44, as referred to herein, comprises a silicoaluminophosphate material having a three-dimensional microporous crystal framework of [PO$_2$], [AlO$_2$] and [SiO$_2$] tetrahedral units whose unit empirical formula on an anhydrous basis is:

mR:(Si$_x$Al$_y$P$_z$)O$_2$ wherein "R" represents at least one organic templating agent present in the intracrystalline pore system; "m" represents the moles of "R" present per mole of (Si$_x$Al$_y$P$_z$)O$_2$ and has a value of from zero to 0.3; "x", "y" and "z" represent respectively, the mole fractions of silicon, aluminum and phosphorus, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern (as-synthesized and calcined) which contains at least the d-spacings set forth below in Table XXVI. When SAPO-44 is in the as-synthesized form "m" preferably has a value of from 0.02 to 0.3.

TABLE XXVI

| 2θ | d | Relative Intensity |
|---|---|---|
| 9.4–9.55 | 9.41–9.26 | vs |
| 13.0–13.1 | 6.81–6.76 | w–m |
| 16.1–16.2 | 5.50–5.47 | w–m |
| 20.75–20.85 | 4.28–4.26 | s–vs |
| 30.85–30.95 | 2.898–2.889 | m–s |

All of the as-synthesized SAPO-44 compositions for which X-ray powder diffraction data have presently been obtained have patterns which are within the generalized pattern of Table XXVII, below:

TABLE XXVII

| 2θ | d | 100 × I/I$_o$ |
|---|---|---|
| 9.4–9.5 | 9.41–9.26 | 97–100 |
| 10.95 | 8.08 | 4–12 |
| 13.0–13.1 | 6.81–6.76 | 15–31 |
| 13.3–13.4 | 6.66–6.61 | 1–6 |
| 13.75–13.8 | 6.44–6.42 | 3 |
| 16.1–16.2 | 5.50–5.47 | 31–55 |
| 17.35–17.4 | 5.11–5.10 | 9–16 |

TABLE XXVII-continued

| 2θ | | d | 100 × I/I₀ |
|---|---|---|---|
| 19.0 | | 4.67 | 6 |
| 20.75–20.85 | | 4.28–4.26 | 68–100 |
| 21.0–21.1 | (sh) | 4.23–4.21 | |
| 21.8–21.9 | | 4.08–4.06 | 25 |
| 22.6–22.7 | | 3.93–3.92 | 3–7 |
| 23.1 | | 3.85 | 7–12 |
| 24.45–24.55 | | 3.641–3.626 | 55–74 |
| 26.15–26.2 | | 3.408–3.401 | 16–22 |
| 26.9 | | 3.314 | 1–2 |
| 27.8–27.9 | | 3.209–3.198 | 7–10 |
| 28.5 | | 3.132 | 2–7 |
| 29.7 | | 3.008 | 3–4 |
| 30.2 | | 2.959 | 18–20 |
| 30.85–30.95 | | 2.898–2.889 | 45–50 |
| 31.6–31.65 | | 2.831–2.827 | 1 |
| 32.15–32.2 | | 2.784–2.780 | 2–7 |
| 32.55–32.6 | | 2.751–2.747 | 1–3 |
| 33.0 | | 2.714 | 5 |
| 34.8 | | 2.578 | 1–3 |
| 35.6 | | 2.522 | 8–11 |
| 38.5–38.6 | | 2.338–2.332 | 1 |
| 39.2 | | 2.298 | 1 |
| 39.9–40.0 | | 2.259–2.254 | 1–2 |
| 42.2–42.3 | | 2.141–2.137 | 4 |
| 42.6 | (sh) | 2.122 | |
| 42.9 | (sh) | 2.108 | 4 |
| 43.6–43.7 | | 2.076–2.071 | 2–3 |
| 44.3–44.4 | | 2.045–2.040 | 1 |
| 45.1–45.2 | | 2.010–2.006 | 1 |
| 46.1–46.2 | | 1.969–1.965 | 1 |
| 47.2–47.3 | | 1.926–1.922 | 2 |
| 48.15–48.2 | | 1.890–1.888 | 6–7 |
| 48.7–48.8 | | 1.870–1.866 | 5 |
| 50.4–50.5 | | 1.811–1.807 | 7–9 |
| 51.2–51.3 | | 1.784–1.781 | 1 |
| 52.1–52.2 | | 1.755–1.752 | 2 |
| 53.9–54.0 | | 1.701–1.698 | 6–8 |

EXAMPLE 22 (SAPO-44)

SAPO-44 was prepared by mixing 23.1 grams of 85 wt.% orthophosphoric acid ($H_3PO_4$) and 57.8 grams of water with 40.9 grams of aluminum isopropoxide ($Al(i-OC_3H_7)_3$) and 5.0 grams of water and the mixture stirred until homogeneous. To this mixture were added 12.0 grams of an aqueous sol of 30 wt.% $SiO_2$ and 5.0 grams of water and the mixture stirred until homogenous. To this mixture were added 9.9 grams of cyclohexylamine ($C_6H_{11}NH_2$) and 5.0 grams of water, and the mixture stirred until homogenous. The composition of the final reaction mixture in molar oxide ratios was:

$C_6H_{11}NH_2:0.6SiO_2:Al_2O_3:P_2O_5:50H_2O$

Part of the reaction mixture was placed in a stainless steel pressure vessel lined with an inert plastic material and heated in an oven at 200° C. at autogenous pressure for 52 hours. The solid reaction product was recovered by centrifugation, washed with water, and dried in air at 100° C. The above product was impure but the major product (SAPO-44) had an X-ray powder diffraction pattern characterized by the following data:

TABLE W

| 2θ | d | 100 × I/I₀ |
|---|---|---|
| 7.5* | 11.8 | 2 |
| 9.5 | 9.31 | 100 |
| 10.95 | 8.08 | 4 |
| 13.0 | 6.81 | 31 |
| 13.3 | 6.66 | 1 |
| 13.75 | 6.44 | 3 |
| 14.9* | 5.95 | 1 |
| 16.15 | 5.49 | 51 |
| 17.4 | 5.10 | 9 |
| 19.0 | 4.67 | 6 |
| 19.7* | 4.51 | 1 |
| 20.85 | 4.26 | 98 |
| 21.1 (sh)* | 4.21 | |
| 21.9 | 4.06 | 25 |
| 22.5 (sh)* | 3.95 | 7 |
| 22.7 | 3.92 | |
| 23.1 | 3.85 | 12 |
| 24.55 | 3.626 | 55 |
| 25.9 (sh)* | 3.440 | 22 |
| 26.2 | 3.401 | |
| 26.9 | 3.314 | 1 |
| 27.9 | 3.198 | 10 |
| 28.5 | 3.132 | 2 |
| 29.0* | 3.079 | 1 |
| 29.7 | 3.008 | 4 |
| 30.2* | 2.959 | 18 |
| 30.9 | 2.894 | 80 |
| 31.6 | 2.831 | 1 |
| 32.15 | 2.784 | 2 |
| 32.55 | 2.751 | 3 |
| 33.0 | 2.714 | 5 |
| 33.6* | 2.667 | 1 |
| 34.8* | 2.578 | 3 |
| 35.6 | 2.522 | 11 |
| 38.5 | 2.338 | 1 |
| 39.2 | 2.298 | 1 |
| 39.9 | 2.259 | 2 |
| 42.3 | 2.137 | 4 |
| 42.6 (sh) | 2.122 | |
| 43.7 | 2.071 | 3 |
| 44.4 | 2.040 | 1 |
| 45.2 | 2.006 | 1 |
| 46.2 | 1.965 | 1 |
| 47.3 | 1.922 | 2 |
| 48.2* | 1.888 | 6 |
| 48.8 | 1.866 | 5 |
| 50.5 | 1.807 | 9 |
| 51.2 | 1.784 | 1 |
| 52.2 | 1.752 | 2 |
| 54.0 | 1.698 | 8 |

*Possibly contains peak of another composition

Chemical analysis indicated the composition of the product (SAPO-44) to be:

$0.59(C_6H_{11}NH_2):0.47SiO_2:Al_2O_3:0.85P_2O_5:0.64H_2O$.

This corresponds to a unit empirical formula (anhydrous basis) of:

$0.14(C_6H_{11}NH_2):(Si_{0.11}Al_{0.48}P_{0.41})O_2$ (b) A portion of the solids crystalline product obtained by heating a portion of the above reaction mixture at 200° C. for 168 hours exhibited an X-ray powder diffraction pattern characteristic of SAPO-44 and was then calcined in air at about 550° C. for 2 hours. The calcined product had an X-ray powder diffraction pattern characterized by the following data:

TABLE Y

| 2θ | d | 100 × I/I₀ |
|---|---|---|
| 7.4* | 11.9 | 1 |
| 9.5 | 9.3 | 100 |
| 10.9 | 8.12 | 3 |
| 12.95 | 6.84 | 46 |

TABLE Y-continued

| 2θ | d | 100 × I/I₀ |
|---|---|---|
| 13.4 | 6.61 | 3 |
| 13.9 | 6.37 | 3 |
| 16.1 | 5.50 | 22 |
| 17.8 | 4.98 | 22 |
| 19.1 | 4.65 | 3 |
| 20.75 | 4.28 | 54 |
| 22.1 | 4.02 | 5 |
| 22.65 | 3.925 | 1 |
| 23.2 | 3.834 | 11 |
| 24.9 | 3.576 | 23 |
| 26.1 | 3.414 | 18 |
| 27.2 | 3.278 | 1 |
| 27.8 | 3.209 | 3 |
| 28.2 | 3.164 | 7 |
| 29.2 | 3.058 | 1 |
| 29.75 | 3.003 | 3 |
| 30.8 | 2.903 | 40 |
| 31.2 | 2.867 | 16 |
| 31.8 | 2.814 | 1 |
| 32.5 | 2.755 | 2 |
| 33.6* | 2.667 | 3 |
| 34.8* | 2.578 | 5 |
| 35.2 | 2.550 | 1 |
| 36.2 | 2.481 | 3 |
| 43.0 | 2.103 | 1 |
| 48.2* | 1.888 | 1 |
| 49.2 | 1.852 | 2 |
| 51.1 | 1.787 | 2 |
| 53.8 | 1.704 | 1 |
| 54.6 | 1.681 | 1 |

*possibly contains peak from another composition (c) Adsorption capacities were measured on the calcined product of (b) using a standard McBain-Bakr gravimetric adsorption apparatus. The following data were obtained on a sample activated at 350° C.:

| | Kinetic Diameter, Å | Pressure Torr | Temp., °C. | Wt % Adsorbed |
|---|---|---|---|---|
| O₂ | 3.46 | 98 | −183 | 25.5 |
| O₂ | 3.46 | 746 | −183 | 32.3 |
| n-hexane | 4.3 | 48 | 23.9 | 3.6 |
| isobutane | 5.0 | 101 | 25.4 | 0 |

The pore size of the calcined product is between about 4.3 Å and about 5.0 Å, as shown by adsorption of n-hexane, kinetic diameter of 4.3 Å and negligible adsorption of isobutane, kinetic diameter of 5.0 Å.

SAPO-31

SAPO-31, as referred to herein, comprises a silicoaluminophosphate having a three-dimensional microporous crystal framework of [PO₂], [AlO₂] and [SiO₂] tetrahedral units whose unit empirical formula on an anhydrous basis is:

wherein R represents at least one organic templating agent present in the intracrystalline pore system; "m" represents the moles of "R" present per mole of (Si$_x$Al$_y$P$_z$)O₂ and has a value of from zero to 0.3; "x", "y" and "z" represent respectively, the mole fractions of silicon, aluminum and phosphorus, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern (as-synthesized and calcined) which contains at least the d-spacings set forth below in Table XXVIII. When SAPO-31 is in the as-synthesized form "m" preferably has a value of from 0.02 to 0.3.

TABLE XXVIII

| 2θ | d | Relative Intensity |
|---|---|---|
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

All of the as-synthesized SAPO-31 compositions for which X-ray powder diffraction data have presently been obtained have patterns which are within the generalized pattern of Table XXIX below.

TABLE XXIX

| 2θ | d | 100 × I/I₀ |
|---|---|---|
| 6.1 | 14.5 | 0–1 |
| 8.5–8.6* | 10.40–10.28 | 60–72 |
| 9.5* | 9.31 | 7–14 |
| 13.2–13.3* | 6.71–6.66 | 1–4 |
| 14.7–14.8 | 6.03–5.99 | 1–2 |
| 15.7–15.8* | 5.64–5.61 | 1–8 |
| 17.05–17.1 | 5.20–5.19 | 2–4 |
| 18.3–18.4 | 4.85–4.82 | 2–3 |
| 20.2–20.3 | 4.40–4.37 | 44–55 |
| 21.1–21.2* | 4.21–4.19 | 6–28 |
| 21.9–22.1* | 4.06–4.02 | 32–38 |
| 22.6–22.7* | 3.93–3.92 | 100 |
| 23.3–23.35* | 3.818–3.810 | 2–20 |
| 25.1* | 3.548 | 3–4 |
| 25.65–25.75 | 3.473–3.460 | 2–3 |
| 26.5* | 3.363 | 1–4 |
| 27.9–28.0 | 3.198–3.187 | 8–10 |
| 28.7* | 3.110 | 0–2 |
| 29.7 | 3.008 | 4–5 |
| 31.7–31.8 | 2.823–2.814 | 15–18 |
| 32.9–33.0* | 2.722–2.714 | 0–3 |
| 35.1–35.2 | 2.557–2.550 | 5–8 |
| 36.0–36.1 | 2.495–2.488 | 1–2 |
| 37.2 | 2.417 | 1–2 |
| 37.9–38.1* | 2.374–2.362 | 2–4 |
| 39.3 | 2.292 | 2–3 |
| 43.0–43.1* | 2.103–2.100 | 1 |
| 44.8–45.2* | 2.023–2.006 | 1 |
| 46.6 | 1.949 | 1–2 |
| 47.4–47.5 | 1.918 | 1 |
| 48.6–48.7 | 1.873–1.870 | 2 |
| 50.7–50.8 | 1.801–1.797 | 1 |
| 51.6–51.7 | 1.771–1.768 | 2–3 |
| 55.4–55.5 | 1.658–1.656 | 1 |

*Possibly contains peak from a minor impurity

EXAMPLE 23 (SAPO-31)

SAPO-31 was crystallized from a reaction mixture prepared by combining 81.7 grams of aluminum isopropoxide (Al(i—OC₃H₇)₃) with 46.1 grams of 85 wt. % orthophosphoric acid (H₃PO₄) and 85.0 grams of water and stirring until homogeneous. To this mixture were added 24.0 grams of an aqueous sol of 30 wt. % SiO₂ and 42.8 grams of water, and the mixture stirred until homogeneous. To this mixture were added 20.2 grams of di-n-propylamine (Pr₂NH) and 34.0 grams of water, and the mixture stirred until homogeneous. To this mixture was added 5.8 grams of AlPO₄-31 seed crystals and the mixture stirred until homogeneous. The composition of the final reaction mixture in molar oxide ratios was:

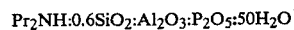

and contained 10 wt. % AlPO₄-31 seed crystals based on the solids content. A portion of this reaction mixture was placed in a stainless steel pressure vessel lined with an inert material and heated in an oven at 200° C. at autogenous pressure for 24 hours. The solid reaction product was recovered by filtration, washed with water, and dried in air at 100° C. The chemical composition of the SAPO-31 product in terms of molar oxide ratios (anhydrous basis) was:

$$0.16(Pr_2NH):Al_2O_3:0.15SiO_2:0.83P_2O_5$$

which corresponds to the unit empirical formula:

$$0.04Pr_2NH:(Si_{0.04}Al_{0.53}P_{0.43})O_2$$

The X-ray powder diffraction pattern of the SAPO-31-containing product was characterized by the following data:

TABLE Z

| $2\theta$ | d | $100 \times I/I_o$ |
|---|---|---|
| 7.25* | 12.193 | (sh) |
| 8.539 | 10.355 | 72 |
| 9.530* | 9.280 | 14 |
| 13.279* | 6.668 | 4 |
| 15.774* | 5.618 | 8 |
| 17.104 | 5.184 | 6 |
| 18.380 | 4.827 | 3 |
| 20.280 | 4.379 | 43 |
| 20.5* | 4.332 | (sh) |
| 21.153* | 4.200 | 22 |
| 22.033 | 4.034 | 28 |
| 22.662* | 3.924 | 100 |
| 23.316 | 3.815 | 14 |
| 25.145 | 3.542 | 3 |
| 25.718 | 3.464 | 3 |
| 26.566* | 3.355 | 3 |
| 26.701 | 3.339 | 4 |
| 27.976 | 3.189 | 9 |
| 28.810* | 3.099 | 4 |
| 29.797 | 2.998 | 6 |
| 31.760 | 2.817 | 16 |
| 33.016 | 2.713 | 3 |
| 34.367* | 2.609 | 2 |
| 35.215 | 2.549 | 8 |
| 36.090 | 2.489 | 2 |
| 37.777* | 2.381 | 3 |
| 37.938* | 2.372 | 3 |
| 38.113 | 2.361 | 3 |
| 39.402 | 2.287 | 3 |
| 39.641 | 2.274 | 2 |
| 40.195 | 2.244 | 2 |
| 44.891* | 2.019 | 2 |
| 45.345 | 2.000 | 2 |
| 46.708 | 1.945 | 2 |
| 51.670 | 1.769 | 3 |

*contains impurity peak

The X-ray powder diffraction pattern of the SAPO-31-containing product after calcination in air for 7 hours at 550° C. was characterized by the following data:

TABLE AA

| $2\theta$ | d | $100 \times I/I_o$ |
|---|---|---|
| 7.7 | 11.5 | (sh) |
| 8.5 | 10.4 | 100 |
| 8.9 | 9.94 | (sh) |
| 9.6 | 9.21 | (sh) |
| 9.8 | 9.03 | 3 |
| 12.85 | 6.89 | 1 |
| 14.7 | 6.03 | 7 |
| 16.1 | 5.50 | 3 |
| 17.05 | 5.20 | 10 |
| 18.45 | 4.81 | 2 |
| 20.3 | 4.37 | 34 |
| 21.4 | 4.15 | (sh) |
| 22.05 | 4.03 | 37 |
| 22.6 | 3.93 | 81 |
| 23.35 | 3.81 | 3 |
| 25.1 | 3.548 | 3 |
| 25.7 | 3.466 | 4 |
| 27.9 | 3.198 | 11 |
| 29.7 | 3.008 | 8 |
| 31.0 | 2.885 | 1 |
| 31.7 | 2.823 | 18 |
| 32.4 | 2.763 | 1 |
| 35.1 | 2.557 | 7 |
| 36.2 | 2.481 | 2 |
| 37.2 | 2.417 | 2 |
| 37.6 | 2.392 | 2 |
| 38.3 | 2.350 | 2 |
| 39.3 | 2.292 | 3 |
| 39.6 | 2.276 | 1 |
| 40.3 | 2.238 | 3 |
| 43.2 | 2.094 | 1 |
| 44.0 | 2.058 | 1 |
| 45.0 | 2.014 | 2 |
| 47.1 | 1.929 | 3 |
| 47.6 | 1.910 | 2 |
| 48.6 | 1.873 | 2 |
| 49.2 | 1.852 | 1 |
| 50.8 | 1.797 | 1 |
| 51.6 | 1.771 | 4 |
| 55.6 | 1.653 | 1 |

(b) Adsorption capacities were measured on the product of (a) and the following data were obtained on a sample activated at 350° C. in vacuum.

| | Kinetic Diameter, A | Pressure Torr | Temp., °C. | Wt. % Adsorbed |
|---|---|---|---|---|
| O₂ | 3.46 | 99 | −183 | 8.8 |
| O₂ | 3.46 | 740 | −183 | 15.4 |
| H₂O | 2.65 | 4.6 | 23 | 6.9 |
| H₂O | 2.65 | 19.4 | 24 | 21.1 |
| Cyclohexane | 6.0 | 49 | 25 | 7.2 |
| Neopentane | 6.2 | 400 | 24 | 5.9 |

It is apparent from these data that the pore size of SAPO-31 is greater than 6.2 A.

SAPO-41

SAPO-41, as referred to herein, comprises a silicoaluminophosphate having a three-dimensional microporous crystal framework structure of [PO₂], [AlO₂] and [SiO₂] tetrahedral units, and whose unit empirical formula on an anhydrous basis is:

$$mR:(Si_xAl_yP_z)O_2$$

wherein R represents at least one organic templating agent present in the intracrystalline pore system; "m" represents the moles of "R" present per mole of $(Si_xAl_yP_z)O_2$ and has a value of from zero to 0.3; "x", "y" and "z" represent respectively, the mole fractions of silicon, aluminum and phosphorus, said mole fractions being within the compositional area bounded by points A, B, C, D and E on the ternary diagram which is FIG. 1, or preferably within the area bounded by points a, b, c, d and e on the ternary diagram which is FIG. 2, said silicoaluminophosphate having a characteristic X-ray powder diffraction pattern (as-synthesized and calcined) which contains at least the d-spacings set forth below in Table XXX. When SAPO-41 is in the as-synthesized form "m" preferably has a value of from 0.02 to 0.3.

TABLE XXX

| 2θ | d | Relative Intensity |
|---|---|---|
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.44 | w–m |

All of the as-synthesized SAPO-41 compositions for which X-ray powder diffraction data have presently been obtained have patterns which are within the generalized pattern of Table XXXI, below.

TABLE XXXI

| 2θ | d | 100 × I/I$_o$ |
|---|---|---|
| 6.7–6.8 | 13.19–12.99 | 15–24 |
| 9.6–9.7 | 9.21–9.11 | 12–25 |
| 13.6–13.8 | 6.51–6.42 | 10–28 |
| 18.2–18.3 | 4.87–4.85 | 8–10 |
| 20.5–20.6 | 4.33–4.31 | 10–32 |
| 21.1–21.3 | 4.21–4.17 | 100 |
| 22.1–22.3 | 4.02–3.99 | 45–82 |
| 22.8–23.0 | 3.90–3.87 | 43–58 |
| 23.1–23.4 | 3.82–3.80 | 20–30 |
| 25.2–25.5 | 3.53–3.49 | 8–20 |
| 25.5–25.9 | 3.493–3.44 | 12–28 |
| 29.3–29.5 | 3.048–3.028 | 17–23 |
| 31.4–31.6 | 2.849–2.831 | 5–10 |
| 33.1–33.3 | 2.706–2.690 | 5–7 |
| 37.6–37.9 | 2.392–2.374 | 10–15 |
| 38.1–38.3 | 2.362–2.350 | 7–10 |
| 39.6–39.8 | 2.276–2.265 | 2–5 |
| 42.8–43.0 | 2.113–2.103 | 5–8 |
| 49.0–49.3 | 1.856–1.848 | 1–8 |
| 51.5 | 1.774 | 0–8 |

EXAMPLE 24 (SAPO-41)

(a) SAPO-41 was prepared by combining 9.22 grams of 85 wt. % orthophosphoric acid ($H_3PO_4$) and 5.78 grams of water, to which was added 5.52 grams of hydrated aluminum oxide, (a pseudo-boehmite phase, 74.2 wt. % $Al_2O_3$, 25.8 wt. % $H_2O$) and stirred until homogeneous. To this mixture was added a mixture of 1.04 grams of a fume silica (92.8 wt. % $SiO_2$, 7.2 wt. % $H_2O$) in 41.67 grams of an aqueous solution of 25.9 wt. % tetra-n-butylammonium hydroxide (TBAOH). This mixture was stirred until homogeneous and then another 41.67 grams of TBAOH was slowly added with stirring until a homogeneous mixture was obtained. The composition of the final reaction mixture in molar oxide ratios was:

$(TBA)_2O:Al_2O_3:P_2O_5:0.4SiO_2:98.7H_2O$

A portion of the reaction mixture was sealed in a stainless steel pressure vessel lined with an inert material and heated in an oven at 200° C. at autogenous pressure for 144 hours. The solid reaction product was recovered by centrifuging and washing with water, and dried in air at room temperature. The product had an X-ray powder diffraction pattern characterized by the following data:

TABLE BB

| 2θ | d | 100 × I/I$_o$ |
|---|---|---|
| 6.7 | 13.19 | 24 |
| 9.6 | 9.21 | 25 |
| 13.6 | 6.51 | 28 |
| 18.2 | 4.87 | 10 |
| 20.5 | 4.33 | 10 |
| 21.1 | 4.21 | 100 |
| 22.1 | 4.02 | 82 |
| 22.8 | 3.90 | 43 |
| 23.1 | 3.85 | 30 |
| 25.3 | 3.52 | 20 |
| 25.7 | 3.47 | 28 |
| 29.3 | 3.048 | 23 |
| 31.4 | 2.848 | 10 |
| 33.1 | 2.706 | 7 |
| 37.6 | 2.392 | 15 |
| 38.1 | 2.362 | 7 |
| 39.6 | 2.276 | 5 |
| 43.0 | 2.103 | 8 |
| 49.1 | 1.855 | 8 |
| 51.5 | 1.774 | 8 |

By chemical analysis the composition of the SAPO-41 was found to be 5.2 wt. % C; 38.1 wt. % $Al_2O_3$; 41.1 wt. % $P_2O_5$; 7.1 wt. % $SiO_2$; and by difference, LOI was 13.7 wt. %; which gave a product composition in terms of molar oxide ratios of:

$0.036(TBA)_2O:1.0Al_2O_3:0.77P_2O_5:0.32SiO_2:1.0H_2O$ which corresponds to the unit empirical formula:

$0.02TBA:(Si_{0.08}Al_{0.52}P_{0.40})O_2$ (b) A portion of the product of (a) was calcined in air at 600° C. for 2 hours and then at 700° C. for 1 hour. The calcined product had an X-ray powder diffraction pattern characterized by the following data:

TABLE CC

| 2θ | d | 100 × I/I$_o$ |
|---|---|---|
| 6.7 | 13.19 | 17 |
| 9.7 | 9.12 | 33 |
| 13.6 | 6.51 | 27 |
| 18.4 | 4.82 | 10 |
| 20.5 | 4.33 | 6 |
| 21.3 | 4.17 | 100 |
| 22.3 | 3.99 | 62 |
| 22.8 | 3.90 | 38 |
| 23.0 | 3.87 | 36 |
| 25.4 | 3.52 | 25 |
| 25.7 | 3.466 | 23 |
| 28.1 | 3.175 | 4 |
| 29.4 | 3.038 | 19 |
| 31.4 | 2.849 | 10 |
| 33.2 | 2.698 | 10 |
| 36.7 | 2.449 | 4 |
| 37.9 | 2.374 | 10 |
| 38.4 | 2.344 | 4 |
| 39.7 | 2.270 | 4 |
| 43.3 | 2.089 | 6 |
| 51.5 | 1.774 | 2 |

(C) Adsorption capacities were measured on the calcined product of part (b) using a standard McBain-Bakr gravimetric adsorption apparatus. The following data were obtained on a sample activated at 350° C.

| | Kinetic Diameter, Å | Pressure Torr | Temp., °C. | Wt. % Adsorbed |
|---|---|---|---|---|
| $O_2$ | 3.46 | 100 | −183 | 9.3 |
| $O_2$ | 3.46 | 750 | −183 | 11.8 |
| Cyclohexane | 6.0 | 60 | 24 | 4.2 |
| Neopentane | 6.2 | 743 | 24 | 1.2 |
| $H_2O$ | 2.65 | 4.6 | 24 | 10.4 |

-continued

| | Kinetic Diameter, A | Pressure Torr | Temp., °C. | Wt. % Adsorbed |
|---|---|---|---|---|
| $H_2O$ | 2.65 | 20.0 | 24 | 21.9 |

The pore size of the calcined product was determined to be between about 6.0 and about 6.2 A as shown by adsorption of cyclohexane, kinetic diameter of 6.0 A and negligible adsorption of neopentane, kinetic diameter of 6.2 A.

(d) EDAX (energy dispersive analysis by X-ray) microprobe analysis, performed in conjunction with SEM (scanning electron microscope) study on crystals having a crystal morphology characteristic of SAPO-41 gave the following analysis based on relative peak heights:

| | Rod | Agglomerate |
|---|---|---|
| Si | 0.09 | 0.11 |
| Al | 1.0 | 1.0 |
| P | 0.87 | 0.74 |

EXPERIMENTAL PROCEDURE (LIGHT OLEFIN PRODUCTION)

The production of light olefins in the examples was carried out by mixing about 0.5 gram of a selected SAPO with 2.5 grams of quartz chips (20–30 U.S. Standard mesh). The resulting mixture was then placed in a ¼ inch (outside diameter) No. 304 stainless steel tubular reactor having a wall thickness of 0.035 inch. The tubular reactor was immersed in a fluidized heated sand bath having electrical resistance heaters provided for maintaining the sand bath and the tubular reactor at the desired temperature. Thermocouples were provided for measurement of the reactor temperature.

A selected feedstock was introduced to the tubular reactor by means of a Model 100 Altex Metering Pump (from Altex Corporation, a subsidiary of the Beckmann Corporation) concurrently with a stream of diluent with nitrogen and water (steam) being employed as diluents (unless otherwise noted in the examples hereinafter). The pressure employed in the examples was the autogenous pressure (about one (1) to about two (2) atmospheres unless otherwise noted. The ratios of these components are reported as weight ratios. When nitrogen was employed as a diluent it was introduced at a flow rate of about 5 cubic centimeters per minute.

The effluent from the tubular reactor (the reaction products) was analyzed. The liquid component of the effluent was collected at room temperature and subsequently analyzed by vapor phase chromatography, whereas the gaseous component of the effluent was sampled and analyzed directly from the effluent stream by vapor phase chromatography.

The analyses of both the liquid and vapor components of the effluent from the tubular reactor were carried out by programmed temperature chromatography having a thermal conductivity detector with a programmed increase in the chromatographic column's temperature over the chromatographic analysis. The analysis of the liquid and vaporous components of the effluent, including the analysis of all standards was carried out using chromatographic techniques by use of the following chromatographic instruments:

| | Phase Analyzed | |
|---|---|---|
| | Liquid | Vapor |
| Chromatograph Column | Varian 3700 20 feet × ⅛ inch (O.D.) stainless steel | Hewlett Packard 11 feet × ⅛ inch (O.D.) stainless steel |
| Packing | 10% Carbowax Chrom T 60/80 mesh | Porapak R |

Unless otherwise noted, the Molar Conversion to total products, based on methanol ethanol, dimethylether, diethylether or mixtures thereof, was 100% with the Molar Efficiency to a particular product being given as a percentage. When a product was not detected (ND) or if only a trace amount was qualitatively detected such is reported as ND or Trace, respectively. Further, although it has been observed that the methane and carbon dioxide formed in the process at temperatures of about 400° C. and higher are primarily derived from contact of the feedstock with the walls of the reactor these values are included since they do affect the efficiency of the overall process although their formation may be minimized by changes in the reactor design. The following examples are provided to exemplify the invention and are not meant to be limiting in any way. The SAPO's employed in the examples hereinafter were the calcined SAPO's as described in the referred to preparative example.

PRODUCTION OF LIGHT OLEFINS: EXAMPLES

Example 25

The SAPO of Example 7 molecular sieve referred to above as SAPO-17 was employed in the instant process for the conversion of a feedstock comprising water and methanol to hydrocarbon products such including light olefin products. The conversion was carried out under four different sets of process conditions at the autogeneous pressure, all of which resulted in the formation of over 50 molar percent of hydrocarbon phase as light olefin products. The formation of dimethyl ether was not detected under these process conditions and an ethylene to propylene molar ratio of about 0.8 or greater was observed in each case. The results are set forth in Table XXXII.

TABLE XXXII

| | 375° C.[1,3] | | | 425° C.[2,3] | | | 450° C.[3,4] | | | 500° C.[3,5] | |
|---|---|---|---|---|---|---|---|---|---|---|---|
| Ethylene | 30.6 | 37.3 | 36.5 | 47.4 | 53.3 | 52.5 | 49.2 | 53.5 | 53.3 | 38.6 | 41.6 |
| Ethane | 0.3 | 0.5 | 0.5 | 0.8 | 0.5 | 0.5 | 0.4 | 0.5 | 0.4 | 0.3 | 0.4 |
| Propylene | 37.4 | 34.8 | 29.3 | 29.5 | 26.0 | 26.4 | 24.8 | 22.8 | 23.3 | 15.3 | 13.6 |
| Propane | 0.2 | Trace | Trace | Trace | ND | ND | Trace | ND | ND | ND | ND |
| Butenes | 15.2 | 13.9 | 12.2 | 8.8 | 9.2 | 7.7 | 7.0 | 6.3 | 6.5 | 3.3 | 3.4 |
| $C_5$'s | 8.0 | 6.8 | 4.9 | 4.2 | 3.1 | 2.5 | 2.5 | 1.9 | 2.2 | 1.2 | 0.9 |
| $C_6$'s | 3.7 | 2.9 | 2.0 | 1.2 | 0.8 | 0.6 | Trace | 0.6 | 0.7 | ND | ND |
| Methane | 4.2 | 3.6 | 2.9 | 4.4 | 4.1 | 4.2 | 6.3 | 6.5 | 6.7 | 15.2 | 18.6 |

TABLE XXXII-continued

|  | 375° C.[1,3] | | | 425° C.[2,3] | | | 450° C.[3,4] | | | 500° C.[3,5] | |
|---|---|---|---|---|---|---|---|---|---|---|---|
| Carbon Dioxide | 0.4 | 0.3 | 0.2 | 4.1 | 2.9 | 2.9 | 9.8 | 8.0 | 6.9 | 26.8 | 21.5 |
| Hours on Stream | 1 | 2.5 | 4.7 | 2.5 | 5.5 | 8.5 | 2.5 | 5.6 | 8.6 | 2.5 | 4.0 |

[1]WHSV (Methanol) = 0.86
WHSV (H$_2$O) = 2.00
[2]WHSV (Methanol) = 0.87
WHSV (H$_2$O) = 2.04
[3]The feed was a mixture of water and methanol having a weight ratio of 70/30.
[4]WHSV (Methanol) = 0.86 hr$^{-1}$
WHSV (H$_2$O) = 2.01 hr$^{-1}$
[5]WHSV (Methanol) = 0.85 hr$^{-1}$
WHSV (H O) = 1.99 hr$^{-1}$

EXAMPLE 26

The SAPO referred to above in Example 12 as SAPO-34 was employed for the conversion of methanol to light olefin products at a temperature of 375° C., atmospheric pressure (i.e., about 15 psia), and at a WHSV (methanol) of 1.17 hr$^{-1}$ and a WHSV (H$_2$O) of 2.73 hr$^{-1}$. The results are set forth in Table XXXIII.

TABLE XXXIII

| Ethylene | 35.1 | 34.9 | 35.0 |
|---|---|---|---|
| Ethane | Trace | 0.3 | 0.6 |
| Propylene | 41.9 | 43.4 | 43.0 |
| Propane | 0.5 | 0.2 | 0.4 |
| Butenes | 16.8 | 16.5 | 15.8 |
| Butane | Trace | Trace | Trace |
| C$_5$'s | 3.3 | 3.3 | 3.6 |
| C$_6$'s | 0.7 | Trace | Trace |
| Methane | 1.2 | 1.2 | 1.5 |
| Carbon Dioxide | 0.7 | 0.2 | 0.2 |
| Hours on Stream | 1.8 | 3.3 | 6.3 |

EXAMPLE 27

The SAPO referred to above in Example 5 as SAPO-16 was employed according to the Experimental Procedure for the conversion of methanol to light olefin products at temperatures of 375° C. and 425° C. The results are set forth in Table XXXIV.

TABLE XXXIV[1]

|  | 375° | 425° C. |
|---|---|---|
| Ethylene | 0.5 | 3.0 |
| Ethane | trace | 0.3 |
| Propylene | 0.6 | 2.3 |
| Propane | trace | trace |
| Butanes | trace | trace |
| C$_5$'s | ND | ND |
| Dimethyl Ether | 98.9 | 94.7 |
| WHSV (Methanol), hr$^{-1}$ | 0.87 | 0.82 |
| WHSV (Water), hr$^{-1}$ | 2.03 | 1.91 |
| Conversion | 53 | 51 |
| Hours on Stream | 2 | 1 |

[1]Methane and carbon dioxide are not included in the calculation of molar efficiency.

EXAMPLE 28

The SAPO referred to above in Example 10 as a SAPO-34 was employed in the instant process for conversion of a feedstock comprising methanol to light olefin products at 375° C. and atmospheric pressure using a methanol to water feedstock having a weight ratio of water to methanol of 70 to 30 (WHSV (Methanol)=0.84 hr$^{-1}$ and WHSV (Water)=1.96 hr$^{-1}$). The results are set forth in Table XXXV.

TABLE XXXV

| Ethylene | 33.7 | 41.3 |
|---|---|---|
| Ethane | 0.8 | 0.8 |
| Propylene | 42.0 | 42.8 |

TABLE XXXV-continued

| Propane | 0.8 | 0.6 |
|---|---|---|
| Butane | Trace | ND |
| Butenes | 18.2 | 11.2 |
| C$_5$'s | 1.9 | 1.3 |
| C$_6$'s | Trace | ND |
| Methane | 2.2 | 1.3 |
| Carbon Dioxide | 0.6 | 0.7 |
| Hours on Stream | 1.1 | 3.3 |

EXAMPLE 29

The SAPO referred to above in Example 17 as SAPO-35 was employed to produce a hydrocarbon mixture containing ethylene and propylene according to the above described Experimental Procedure. The results at a process temperature of 350° C. and 370° C. and at the autogenous pressure are set forth in Table XXXVI.

TABLE XXXVI[1]

|  | 350° C. | 375° C. |
|---|---|---|
| Ethylene | 43.9 | 42.8 |
| Ethane | ND | 0.4 |
| Propylene | 23.7 | 31.2 |
| Propane | 0.5 | 1.3 |
| Butenes | 4.1[2] | 8.0 |
| Butane | ND | Trace |
| C$_5$'s | 2.1 | 2.9 |
| C$_6$'s | Trace | 1.4 |
| Methane | 12.9 | 11.5 |
| Carbon Dioxide | 4.5 | 0.6 |
| Dimethyl Ether | 8.5 | ND |
| Conversion | 64 | 100 |
| Hours on stream | 0.25 | 1 |

[1]WHSV (at 350° C.): Methanol = 1.11 hr$^{-1}$
Water = 2.60 hr.$^{-1}$
WHSV (at 375° C.): Methanol = 2.60 hr$^{-1}$
Water = 2.43 hr.$^{-1}$
[2]Approximate value due to methanol interference on the gas chromatographic analysis.

EXAMPLE 30

The SAPO referred to above in Example 22 as SAPO-44 was employed to convert a feedstock, comprising methanol and water according to the above described Experimental Procedure. The temperature was 375° C. the pressure was the autogenous pressure and the process was carried out for a period of 1 hour. The WHSV for methanol and water were respectively 0.85 and 1.99 with the methanol conversion being 45 molar percent. The results are set forth in Table XXXVII.

TABLE XXXVII

| Ethylene | 17.7 |
|---|---|
| Ethane | 6.3 |
| Propylene | 13.3 |
| Propane | 9.5 |
| C$_4$'s[1] | 7.5 |

TABLE XXXVII-continued

| | |
|---|---|
| $C_5$'s | 1.1 |
| $C_6$'s | ND |
| Methane | 5.5 |
| Carbon Dioxide | 2.8 |
| Dimethyl Ether | 36.4 |

[1] Approximate value due to methanol interference on the gas chromatograph

EXAMPLE 31

The SAPO referred to above in Example 15 as a SAPO-34 was employed in the instant process to convert a molar mixture of water and methanol to light olefin products according to the above discussed Experimental Procedure. Three runs were carried out at varying molar amounts of methanol and both with and without the use of a diluent and with varying amounts of water present. The temperature was 375° C. and the pressure was the autogeneous pressure. The results demonstrate the increase in selectivity to light olefin products (at constant conversion) obtained when diluent is employed in the instant process. The results of the three runs are set forth in Tables XXXVIII, XXXIX, and XXXX.

TABLE XXXVIII[1,2]

| | | |
|---|---|---|
| Ethylene | 39.9 | 41.5 |
| Ethane | 1.0 | 0.8 |
| Propylene | 42.1 | 41.6 |
| Propane | 0.7 | Trace |
| Butenes | 12.3 | 12.0 |
| $C_5$'s | 2.2 | 1.8 |
| $C_6$'s | Trace | Trace |
| Methane | 1.4 | 1.3 |
| Carbon Dioxide | 0.3 | 0.3 |
| Hours on Stream | 4 | 5.5 |

[1] The weight ratio of water to methanol was 70:30. Nitrogen was used as an inert diluent.
[2] WHSV (MEOH): 0.91 hr$^{-1}$
WHSV (H$_2$O): 2.12 hr$^{-1}$

TABLE XXXIX[1,2]

| | | |
|---|---|---|
| Ethylene | 27.8 | 36.8 |
| Ethane | 1.2 | 1.2 |
| Propylene | 44.4 | 48.1 |
| Propane | 0.7 | 0.7 |
| Butenes | 19.2 | 10.2 |
| $C_5$'s | 4.2 | 1.5 |
| $C_6$'s | 0.6 | Trace |
| Methane | 1.9 | 1.4 |
| Carbon dioxide | 0.2 | 0.2 |
| Hours on Stream | 1 | 4.0 |

[1] Weight ratio of water to methanol was 30 to 70 with nitrogen employed as an inert diluent.
[2] WHSV (MeOH): 0.84
WHSV (H$_2$O): 0.36

TABLE XXXX[1,2]

| | | |
|---|---|---|
| Ethylene | 28.4 | 37.5 |
| Ethane | 1.4 | 2.6 |
| Propylene | 44.6 | 42.9 |
| Propane | Trace | Trace |
| Butenes | 16.9[3] | 11.3 |
| $C_5$'s | 3.5 | 1.6 |
| $C_6$'s | 0.9 | 0.4 |
| Methane | 3.0 | 2.7 |
| Carbon Dioxide | 1.4 | 1.1 |
| Hours on Stream | 1 | 4.0 |

[1] Molar ratio of water to methanol was 70:30. No diluent was employed.
[2] WHSV (MeOH): 0.89 hr$^{-1}$
WHSV (H$_2$O): 2.05 hr$^{-1}$
[3] Trace amount of butane observed

EXAMPLE 32

The SAPO referred to above in Example 14 as a SAPO-34 was employed as the catalyst in the instant process for the conversion of methanol to light olefins at four different temperatures. The conversion of methanol to light olefins was carried out under the autogenous pressure at temperatures of 350° C., 375° C., 400° C. and 425° C. The results at these temperatures are set forth in Table XLI.

TABLE XLI

| | 350° C. | 375° C. | 400° C. | 425° C. |
|---|---|---|---|---|
| Ethylene | 37.0 | 42.6 | 46.0 | 48.6 |
| Ethane | 0.4 | 0.8 | 0.6 | 0.6 |
| Propylene | 39.8 | 41.4 | 36.2 | 30.7 |
| Propane | 0.3 | 0.5 | 0.5 | 0.5 |
| Butenes | 16.6 | 10.7 | 11.7 | 8.8 |
| Butane | Trace | ND | ND | ND |
| $C_5$'s | 3.8 | 1.7 | 1.6 | 1.3 |
| $C_6$'s | Trace | Trace | Trace | Trace |
| Methane | 1.7 | 1.3 | 2.0 | 4.1 |
| Carbon Dioxide | 0.5 | 0.9 | 1.5 | 5.5 |
| Hours on Stream | 0.9 | 5.2 | 6.3 | 6.2 |
| WHSV (Methanol) hr$^{-1}$ | 0.85 | 0.83 | 0.87 | 0.83 |
| WHSV (Water) hr$^{-1}$ | 1.99 | 1.93 | 2.04 | 1.95 |

EXAMPLE 33

The SAPO referred to above in Example 14 as a SAPO-34 was employed in the instant process in the comparison of the conversion of two different feedstocks to light olefin products. The two feedstocks were: methanol; and dimethyl ether and water. This example was carried out under the autogenous pressure and at a temperature of 375° C. The results are set forth in Table XLII.

TABLE XLII

| | Methanol[1] | | Dimethyl Ether[2] + Water | |
|---|---|---|---|---|
| Ethylene | 36.9 | 32.7 | 35.9 | 35.8 |
| Ethane | 0.8 | 0.9 | 0.4 | 0.4 |
| Propylene | 38.8 | 31.1 | 39.4 | 36.6 |
| Propane | 0.6 | 0.6 | 0.3 | 0.4 |
| Butenes | 11.9 | 9.5 | 17.8 | 12.3 |
| Butane | Trace | Trace | Trace | Trace |
| $C_5$ | 1.9 | 1.4 | 4.5 | 2.1 |
| $C_6$ | Trace | Trace | Trace | Trace |
| Methane | 5.5 | 4.6 | 1.4 | 0.9 |
| Carbon Dioxide | 3.5 | 2.8 | 0.3 | 0.1 |
| Dimethyl Ether | ND | 16.4 | ND | 11.5 |
| Hours on Stream | 1.8 | 2.5 | 0.3 | 1.0 |

[1] WHSV, hr$^{-1}$: 1.1 hr$^{-1}$ (Methanol)
[2] WHSV, hr$^{-1}$: 1.04 hr$^{-1}$ (Dimethyl Ether)
3.13 hr$^{-1}$ (Water)

EXAMPLE 34

The SAPO referred to above in Example 14 as a SAPO-34 was employed in the instant process for the conversion of methanol to light olefin products at a temperature of 375° C. and at the autogenous pressure. The flow rate (WHSV) was employed at two rates to determine the effect of flow rate on light olefin production with the second flow rate being two and one half (2.5X Flow) times that employed as the first flow rate (1X Flow). The results are set forth in Table XLIII.

TABLE XLIII[1]

| | 1 × Flow | | | 2.5 × Flow | | |
|---|---|---|---|---|---|---|
| Ethylene | 38.2 | 39.4 | 42.6 | 37.3 | 38.6 | 28.7 |
| Ethane | 0.5 | 0.5 | 0.8 | 0.3 | 0.5 | 0.3 |

TABLE XLIII[1]-continued

|  | 1 × Flow |  |  | 2.5 × Flow |  |  |
|---|---|---|---|---|---|---|
| Propylene | 40.2 | 40.5 | 41.4 | 40.7 | 41.9 | 31.0 |
| Propane | 0.4 | 0.4 | 0.5 | 0.2 | ND | ND |
| Butenes | 14.5 | 13.3 | 10.7 | 15.1 | 13.8 | 10.0 |
| Butane | Trace | ND | ND | Trace | Trace | Trace |
| $C_5$'s | 2.2 | 2.7 | 1.7 | 3.5 | 2.8 | 1.3 |
| $C_6$'s | 0.7 | 0.6 | Trace | 0.8 | 0.6 | Trace |
| Methane | 1.4 | 1.4 | 1.3 | 1.5 | 1.2 | 0.9 |
| Carbon Dioxide | 2.1 | 1.3 | 0.9 | 0.6 | 0.4 | 0.2 |
| Dimethyl Ether | ND | ND | ND | ND | ND | 27.5 |
| Hours on Stream | 0.9 | 1.7 | 5.2 | 0.8 | 1.5 | 3.8 |

[1]WHSV, hr$^{-1}$ (1 × Flow):
(Methanol): 0.83
(Water): 1.93
WHSV hr$^{-1}$ (2.5 × Flow):
(Methanol): 1.91
(Water): 4.46

EXAMPLE 35

The SAPO referred to above in Example 15 as a SAPO-34 was employed in the instant process for the conversion of ethanol to light olefins at a temperature of 400° C. under the autogenous pressure and at a WHSV (ethanol) of 1.04 hr$^{-1}$. The results are set forth in Table XLIV.

TABLE XLIV

| Ethylene | 15.1 | 61.0 | 76.5 |
|---|---|---|---|
| Ethane | 7.6 | 3.3 | 2.2 |
| Propylene | 21.2 | 28.6 | 15.6 |
| Propane | 31.1 | Trace | ND |
| Butenes | 16.5 | 4.5 | 1.9 |
| $C_5$ | 3.2 | 0.6 | 0.4 |
| $C_6$ | 0.8 | 0.3 | 0.3 |
| Methane | 2.3 | 0.9 | 0.5 |
| Carbon Dioxide | 2.1 | 0.8 | 0.7 |
| Acetaldehyde | ND | ND | 1.8 |
| Hours on Stream | 1.0 | 3.3 | 4.0 |

EXAMPLE 36

The SAPO referred to above in Example 15 as a SAPO-34 was employed in the instant process for the conversion of ethanol in the presence of water to light olefin products at a temperature of 400° under the autogeneous pressure. The WHSV (Ethanol) was 0.87 hr$^{-1}$ and the WHSV (Water) was 4.90 hr$^{-1}$. The results are set forth in Table XLV.

TABLE XLV

| Ethylene | 89.2 | 90.3 | 91.2 |
|---|---|---|---|
| Ethane | 1.1 | 1.1 | 1.2 |
| Propylene | 5.5 | 4.4 | 3.7 |
| Propane | ND | ND | ND |
| Butenes | 1.4 | 1.2 | 1.0 |
| $C_5$'s | 0.6 | 0.4 | 0.3 |
| $C_6$'s | ND | ND | ND |
| Methane | 0.1 | 0.1 | 0.1 |
| Carbon Dioxide | 0.5 | 0.4 | 0.3 |
| Acetaldehyde | 1.5 | 2.2 | 2.2 |
| Hours on Stream | 2.5 | 5.5 | 8.5 |

EXAMPLE 37

A phosphate substituted zeolite was prepared according to the following procedure as derived from example 4 of Canadian Pat. No. 911,417, issued Oct. 3, 1972.

The substituted zeolite was prepared by mixing 24.0 grams of AlCl$_3$.6H$_2$O, 10.4 grams of H$_3$PO$_4$ (85 wt %) and about 200 milliliters of distilled water. The resulting mixture was titrated with a concentrated solution of sodium hydroxide until the mixture had a PH of about 7.5. A precipitate was formed. This precipitate was collected by filtration and washed with about 150 milliliters of distilled water. The wet precipitate was blended with 16.0 grams of Ludox colloidal silica sol, 4.8 grams of sodium hydroxide and then dissolved in 100 milliliters of distilled water. This reaction mixture was then placed in an autoclave with an inert plastic liner and crystallized at about 150° C. at the autogenous pressure for a period of about 118 hours. The reaction mixture had the following composition, expressed in oxide-molar ratios:

1.2Na$_2$O:Al$_2$O$_3$:1.6SiO$_2$:0.9P$_2$O$_5$:110H$_2$O

The resulting product was recovered by filtration, washed with distilled water and air dried at 110° C. The air dried product was ion-exchanged with potassium, analyzed by X-ray and the following X-ray powder diffraction pattern observed:

| d | 100 × I/I$_o$ |
|---|---|
| 9.46 | 100 |
| 6.97 | 21 |
| 5.61 | 17 |
| 5.10 | 21 |
| 4.72 | 10 |
| 4.53 | 5 |
| 4.36 | 74 |
| 4.15 | 7 |
| 4.02 | 9 |
| 3.90 | 43 |
| 3.62 | 28 |
| 3.48 | 16 |
| 3.14 | 10 |
| 2.95 | 95 |
| 2.92 | 53 |
| 2.71 | 9 |
| 2.64 | 19 |
| 2.54 | 14 |
| 2.33 | 9 |
| 2.11 | 7 |
| 2.08 | 3 |

The as-synthesized product was analyzed and found to contain: 13.6 wt. % P$_2$O$_5$; 13.3 wt. % Na$_2$O; 27.7 wt. % Al$_2$O$_3$; 26.5 wt. % SiO$_2$; and 19.2 wt. % H$_2$O; This corresponds to a composition in oxide molar ratios of:

0.79Na$_2$O:Al$_2$O$_3$:1.62SiO$_2$:0.35P$_2$O$_5$:3.92H$_2$O

The as-synthesized product was tested for adsorption capacities using a standard McBain-Bakr gravimetric adsorption apparatus. The following data were obtained on a sample activated at about 350° C. in vacuum.

|  | Kinetic Diameter, A | Pressure, Torr | Temp., °C. | Wt. % Adsorbed |
|---|---|---|---|---|
| O$_2$ | 3.46 | 760 | −183 | 1.6 |
| N$_2$ | 3.64 | 760 | −196 | — |
| CO$_2$ | 3.3 | 760 | 25 | — |
| N—butane | 4.3 | 760 | 25 | 0.2 |
| H$_2$O | 2.65 | 20 | 25 | 20.9 |

A portion (2.0 grams) of the as-synthesized product was then refluxed for 1 hr. with 20 grams of 10 wt. percent NH$_4$Cl, filtered and dried for a short period at 100° C.

This composition was then employed according to the Experimental Procedure for the conversion of a feedstock containing methanol and water (WHSV (MeOH)=0.89 hr$^{-1}$ and WHSV (H$_2$O)=1.08 hr$^{-1}$). The temperature employed was 375° C., the pressure was the autogenous pressure. The time for the conversion was 1.8 hours. The molar efficiency (given as a percentage) is given in the following Table The molar conversion of methanol to products was only 18.4 percent. The Molar Efficiency to ethylene based on total methanol converted to hydrocarbon products was 0.7 molar percent. The results are reported in Table XLVI.

TABLE XLVI

| | |
|---|---|
| Ethylene | 1.3 |
| Ethane | — |
| Propylene | 2.5 |
| Propane | — |
| C$_4$'s | — |
| C$_5$'s | — |
| C$_6$'s | — |
| Methane | 0.6 |
| Carbon Dioxide | 2.1 |
| Dimethyl Ether | 93.5 |

What is claimed is:

1. The process of making light olefins containing 2 to 4 carbon atoms which comprises contacting a feedstock comprising one or more of methanol, ethanol, dimethyl ether, diethyl ether and mixtures thereof with a silicoaluminophosphate molecular sieve wherein the silicoaluminophosphate molecular sieve comprises a microporous crystalline silicoaluminophosphate whose unit empirical formula in the as-synthesized and anhydrous form is

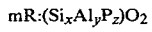

mR:(Si$_x$Al$_y$P$_z$)O$_2$ wherein "R" represents at least one organic templating agent present in the intracrystalline pore system; "m" has a value of from 0.02 to 0.3; "m" represents the moles of "R" present per mole of (Si$_x$Al$_y$P$_z$)O$_2$; "x", "y" and "z" represent the mole fractions of silicon, aluminum and phosphorus respectively, present as tetrahedral units, said mole fractions being such that they are within the pentagonal compositional area defined by points A, B, C, D and E of the ternary diagram which is FIG. 1 of the drawings.

2. The process of making light olefins containing 2 to 4 carbon atoms which comprises contacting a feedstock comprising one or more of methanol, ethanol, dimethyl ether, diethyl ether and mixtures thereof with a silicoaluminophosphate molecular sieve wherein the silicoaluminophosphate molecular sieve comprises a microporous crystalline silicoaluminophosphate whose unit empirical formula in the as-synthesized and anhydrous form is

mR:(Si$_x$Al$_y$P$_z$)O$_2$ wherein "R" represents at least one organic templating agent present in the intracrystalline pore system; "m" has a value of from zero to 0.3; "m" represents the moles of "R" present per mole of (Si$_x$Al$_y$P$_z$)O$_2$; "x", "y" and "z" represent the mole fractions of silicon, aluminum and phosphorus, respectively, present as tetrahedral units, said mole fractions being such that they are within the pentagonal compositional area defined by points A, B, C, D and E of the ternary diagram which is FIG. 1 of the drawings, said silicoaluminophosphate having a characteristic X-ray powder diffraction pattern which contains at least the d-spacings set forth in any one of Tables I, III, V, VIII, X, XIII, XVII, XX, XXII, XXIV, XXVI, XXVIII or XXX.

3. The process of claim 1 wherein the silicoaluminophosphate is characterized by adsorption of oxygen and negligible adsorption of isobutane.

4. The process of claim 1 wherein the silicoaluminophosphate is characterized by adsorption of Xenon and negligible adsorption of isobutane.

5. The process of claim 1 wherein the silicoaluminophosphate is characterized by adsorption of n-hexane and negligible adsorption of isobutane.

6. The process of claim 1 wherein the silicoaluminophosphate has mole fractions of silicon, aluminum and phosphorus within the pentagonal compositional area defined by points a, b, c, d and e of the ternary diagram which is FIG. 2 of the drawings.

7. The process of claims 1 or 6 wherein the silicoaluminophosphate has the characteristic X-ray powder diffraction pattern which contains at least the d-spacings set forth in Table I.

8. The process of claims 1 or 6 wherein the silicoaluminophosphate has the characteristic X-ray powder diffraction pattern which contains at least the d-spacings set forth in Table III.

9. The process of claims 1 or 6 wherein the silicoaluminophosphate has the characteristic X-ray powder diffraction pattern which contains at least the d-spacings set forth in Table V.

10. The process of claims 1 or 6 wherein the silicoaluminophosphate has the characteristic X-ray powder diffraction pattern which contains at least the d-spacings set forth in Table VIII.

11. The process of claims 1 or 6 wherein the silicoaluminophosphate has the characteristic X-ray powder diffraction pattern which contains at least the d-spacings set forth in Table X.

12. The process of claims 1 or 6 wherein the silicoaluminophosphate has the characteristic X-ray powder diffraction pattern which contains at least the d-spacings set forth in Table XIII.

13. The process of claims 1 or 6 wherein the silicoaluminophosphate has the characteristic X-ray powder diffraction pattern which contains at least the d-spacings set forth in Table XVII.

14. The process of claims 1 or 6 wherein the silicoaluminophosphate has the characteristic X-ray powder diffraction pattern which contains at least the d-spacings set forth in Table XX.

15. The process of claims 1 or 6 wherein the silicoaluminophosphate has the characteristic X-ray powder diffraction pattern which contains at least the d-spacings set forth in Table XXII.

16. The process of claims 1 or 6 wherein the silicoaluminophosphate has the characteristic X-ray powder diffraction pattern which contains at least the d-spacings set forth in Table XXIV.

17. The process of claims 1 or 6 wherein the silicoaluminophosphate has the characteristic X-ray powder diffraction pattern which contains at least the d-spacings set forth in Table XXVI.

18. The process of claims 1 or 6 wherein the silicoaluminophosphate has the characteristic X-ray powder diffraction pattern which contains at least the d-spacings set forth in Table XXVIII.

19. The process of claims 1 or 6 wherein the silicoaluminophosphate has the characteristic X-ray powder diffraction pattern which contains at least the d-spacings set forth in Table XXX.

20. The process of claim 1 or 6 wherein in the unit empirical formula

"m" has a value of zero and the silicoaluminophosphate has an X-ray powder diffraction pattern as set forth in any one of Tables C, E, K, M, O, P, R, T, Y, AA and CC.

21. The process of claim 1 or 2 wherein said feedstock contains diluent.

22. The process of claim 21 wherein said diluent is water and comprises between about 1 and about 99 molar percent water.

23. The process of claim 1 or 2 wherein the feedstock is contacted with said silicoaluminophosphate at a temperature between about 200° and about 700° C.

24. The process of claim 23 wherein the feedstock is contacted with said silicoaluminophosphate at a temperature between about 250° and about 600° C.

25. The process of claim 1 or 2 wherein the process is conducted at a pressure between about 0.1 atmosphere and about 1000 atmospheres.

26. The process of claim 25 wherein the process is conducted at a pressure between about 0.1 atmosphere and about 100 atmospheres.

27. The process of claim 1 or 2 wherein said process is carried out in the vapor phase.

28. The process of claim 1 or 2 wherein said process is carried out in the liquid phase.

29. The process of claim 1 or 2 wherein the WHSV is between about 0.01 hr$^{-1}$ and about 100 hr$^{-1}$.

30. The process of claim 29 wherein the WHSV is between about 0.1 hr$^{-1}$ and about 40 hr$^{-1}$.

31. The process of claim 1 or 2 wherein the feedstock comprises methanol.

32. The process of claim 1 or 2 wherein the feedstock comprises methanol and dimethyl ether.

33. The process of claim 1 or 2 wherein the feedstock comprises ethanol.

34. The process of claim 1 or 2 wherein the feedstock comprises ethanol and diethyl ether.

35. The process of claim 1 or 2 wherein the feedstock consists essentially of methanol, dimethyl ether and water.

36. The process of claim 1 or 2 wherein the feedstock consists essentially of methanol and water.

37. The process of claim 1 or 2 wherein the feedstock consists essentially of ethanol and water.

38. The process of claim 1 or 2 wherein the feedstock consists essentially of dimethyl ether and water.

39. The process of claim 21 wherein the diluent is nitrogen.

40. The process of claim 21 wherein the diluent is a paraffin.

41. The process of claim 21 wherein the diluent is helium.

42. The process of claim 21 wherein the diluent is an aromatic compound.

43. The process of claim 1 wherein light olefins constitute at least about 25 molar percent of the hydrocarbon products.

44. The process of claim 43 wherein light olefin products constitute in excess of 50 molar percent of the hydrocarbon products.

45. The process of claim 2 wherein the silicoaluminophsphate has mole fractions of silicon, aluminum and phosphorus within the pentagonal compositional area defined by points a, b, c, d and e of the ternary diagram which is FIG. 2 of the drawings.

46. The process of claims 2 or 45 wherein the silicoaluminophosphate has the characteristic X-ray powder diffraction pattern which contains at least the d-spacings set forth in Table I.

47. The process of claims 2 or 45 wherein the silicoaluminophosphate has the characteristic X-ray powder diffraction pattern which contains at least the d-spacings set forth in Table III.

48. The process of claims 2 or 45 wherein the silicoaluminophosphate has the characteristic X-ray powder diffraction pattern which contains at least the d-spacings set forth in Table V.

49. The process of claims 2 or 45 wherein the silicoaluminophosphate has the characteristic X-ray powder diffraction pattern which contains at least the d-spacings set forth in Table VIII.

50. The process of claims 2 or 45 wherein the silicoaluminophosphate has the characteristic X-ray powder diffraction pattern which contains at least the d-spacings set forth in Table X.

51. The process of claims 2 or 45 wherein the silicoaluminophosphate has the characteristic X-ray powder diffraction pattern which contains at least the d-spacings set forth in Table XIII.

52. The process of claims 2 or 45 wherein the silicoaluminophosphate has the characteristic X-ray powder diffraction pattern which contains at least the d-spacings set forth in Table XVII.

53. The process of claims 2 or 45 wherein the silicoaluminophosphate has the characteristic X-ray powder diffraction pattern which contains at least the d-spacings set forth in Table XX.

54. The process of claims 2 or 45 wherein the silicoaluminophosphate has the characteristic X-ray powder diffraction pattern which contains at least the d-spacings set forth in Table XXII.

55. The process of claims 2 or 45 wherein the silicoaluminophosphate has the characteristic X-ray powder diffraction pattern which contains at least the d-spacings set forth in Table XXIV.

56. The process of claims 2 or 45 wherein the silicoaluminophosphate has the characteristic X-ray powder diffraction pattern which contains at least the d-spacings set forth in Table XXVI.

57. The process of claims 2 or 45 wherein the silicoaluminophosphate has the characteristic X-ray powder diffraction pattern which contains at least the d-spacings set forth in Table XXVIII.

58. The process of claims 2 or 45 wherein the silicoaluminophosphate has the characteristic X-ray powder diffraction pattern which contains at least the d-spacings set forth in Table XXX.

* * * * *

UNITED STATES PATENT AND TRADEMARK OFFICE
CERTIFICATE OF CORRECTION

PATENT NO. : 4,499,327
DATED : February 12, 1985
INVENTOR(S) : Steven W. Kaiser

It is certified that error appears in the above-identified patent and that said Letters Patent is hereby corrected as shown below:

Column 3, line 19, change "phosphorous" to -- phosphorus --.

Column 4, line 40, change "aluminium" to -- aluminum --.

Column 4, line 49, change "(0.5-1.1)$Na_2O_3$" to -- (0.5-1.1)$Na_2O$ --.

Column 5, lines 24 to 26, change "copending application U. S. Ser. No. 400,438, filed July 26, 1982" to -- U. S. Patent No. 4,440,871, issued April 3, 1984 --.

Column 6, line 13, change "perferably" to -- preferably --.

Column 10, lines 24 and 25, change "in copending U. S. Ser. No. 400,438, filed July 26, 1982" to -- U. S. Patent No. 4,440,871 --.

Column 10, line 44, change "$(Si_xAl_yP)O_2$" to -- $(Si_xAl_yP_z)O_2$ --.

Column 10, line 49, change "copending U. S. Ser. No. 400,438" to -- U. S. Patent No. 4,440,871 --.

Column 13, line 53, change "alklaryl" to -- alkylaryl --.

Column 25, line 11, change "of" to -- by --.

UNITED STATES PATENT AND TRADEMARK OFFICE
CERTIFICATE OF CORRECTION

PATENT NO. : 4,499,327

DATED : February 12, 1985

INVENTOR(S) : Steven Kaiser

It is certified that error appears in the above-identified patent and that said Letters Patent is hereby corrected as shown below:

Column 26, line 6, change "phosphorous" to -- phosphorus --.

Column 26, line 12, change "ad" to -- and --.

Column 29, line 34, change "supra" to -- _supra_ --.

Column 29, line 49, change "neglible" to -- negligible --.

Column 30, line 43, change "(TMAOH.5H$_2$O)" to -- (TMAOH:5H$_2$O) --.

Column 34, line 10, change "0.17(TEA)$_2$O:0.33SiO$_2$:Al$_2$O$_3$:0.82P$_2$O$_5$0 40H$_2$O," to -- 0.17(TEA)$_2$O:0.33SiO$_2$:Al$_2$O$_3$:0.82P$_2$O$_5$:0.40H$_2$O, --.

Column 34, line 14, change "0.09(TEA) : (Si$_{0.08}$Al$_{0.51}$P$_{0.41}$)O$_2$." to -- 0.09(TEA):(Si$_{0.08}$Al$_{0.51}$P$_{0.41}$)O$_2$. --.

Column 35, line 17, change "autogeneous" to -- autogenous) --.

Column 35, line 54, after "until" insert -- a --.

Column 36, line 36, change "wt" to -- wt. --.

Column 36, line 49, change "mogenous" to -- mogeneous --.

Column 41, line 11, change "(TMAOH 5.H$_2$O)" to -- (TMAOH:5H$_2$O) --.

Column 43, line 7, after "present" insert -- , --.

UNITED STATES PATENT AND TRADEMARK OFFICE
CERTIFICATE OF CORRECTION

PATENT NO. : 4,499,327
DATED : February 12, 1985
INVENTOR(S) : Steven W. Kaiser

It is certified that error appears in the above-identified patent and that said Letters Patent is hereby corrected as shown below:

Column 43, line 36, change "8.0-8.1" to -- 8.0-8.11 --.

Column 44, line 42-43, change "0.3-4SiO$_2$" to -- 0.34 SiO$_2$ --.

Column 46, line 53, change "38.14-38.25" to -- 38.15-38.25 --.

Column 49, line 46, change "genous" to -- geneous --.

Column 49, line 48, change "homogenous" to -- homogeneous --.

Column 50, line 56, change "solids" to -- solid --.

Column 55, ine 34, change "1.856-1.848" to -- 1.859-1.848 --.

Column 55, line 44, change "fume" to -- fumed --.

Column 56, line 29, change "0.02 TBA:(Si$_{0.08}$Al$_{.0.52}$P$_{0.40}$)O$_2$" to -- 0.02TBA:(Si$_{0.08}$Al$_{0.52}$P$_{0.40}$)O$_2$ --.

Column 57, line 47, after "noted" insert -- ) --.

Column 58, line 24, after "methanol" insert -- , --.

Column 58, line 51, change "autogene" to -- autogen --.

Column 59, line 13, in footnote 5 of Table XXXII change "WHSV(HO)" to -- WHSV(H$_2$O) --.

Column 60, line 29, change "370°C." to -- 375°C. --.

UNITED STATES PATENT AND TRADEMARK OFFICE
CERTIFICATE OF CORRECTION

PATENT NO. : 4,499,327
DATED : February 12, 1985
INVENTOR(S) : Steven W. Kaiser

It is certified that error appears in the above-identified patent and that said Letters Patent is hereby corrected as shown below:

Column 60, line 57 after "375°C." insert --,--.

Column 61, line 19, change "autogeneous" to -- autogenous --.

Column 63, line 46, change "geneous" to -- genous --.

Column 65, line 6, insert after "Table"a -- . --.

Column 68, line 8, change "nophsphate" to -- nophosphate --.

Signed and Sealed this

Fourteenth Day of January 1986

[SEAL]

Attest:

Attesting Officer

DONALD J. QUIGG

Commissioner of Patents and Trademarks